United States Patent
Rock

(10) Patent No.: US 9,619,849 B2
(45) Date of Patent: Apr. 11, 2017

(54) HEALTHCARE DELIVERY SYSTEM AND METHOD

(71) Applicant: Eric Lee Rock, Plano, TX (US)

(72) Inventor: Eric Lee Rock, Plano, TX (US)

(*) Notice: Subject to any disclaimer, the term of this patent is extended or adjusted under 35 U.S.C. 154(b) by 0 days.

(21) Appl. No.: 14/223,537

(22) Filed: Mar. 24, 2014

(65) Prior Publication Data

US 2014/0297301 A1 Oct. 2, 2014

Related U.S. Application Data

(60) Provisional application No. 61/805,355, filed on Mar. 26, 2013.

(51) Int. Cl.
*G06Q 50/22* (2012.01)
*G06Q 10/10* (2012.01)

(52) U.S. Cl.
CPC .......... *G06Q 50/22* (2013.01); *G06Q 10/103* (2013.01)

(58) Field of Classification Search
CPC . A61N 1/3702; G06F 19/3418; G06F 19/322; G06F 19/325
USPC ............................ 705/2–4; 600/300; 607/5
See application file for complete search history.

(56) References Cited

U.S. PATENT DOCUMENTS

| | | | |
|---|---|---|---|
| 5,940,801 A | | 8/1999 | Brown |
| 7,593,952 B2* | | 9/2009 | Soll et al. |
| 7,739,126 B1* | | 6/2010 | Cave et al. ...................... 705/2 |
| 8,183,998 B2* | | 5/2012 | Rao et al. ................ 340/539.12 |
| 8,239,903 B1 | | 8/2012 | Campagna et al. |
| 8,301,233 B2* | | 10/2012 | Zhang et al. .................. 600/515 |
| 8,321,808 B2* | | 11/2012 | Goetz ................ A61N 1/37247 607/46 |

(Continued)

FOREIGN PATENT DOCUMENTS

WO    WO 2013033655 A1    3/2013

OTHER PUBLICATIONS

Doukas, et. al., "Mobile Healthcare Information management Utilizing Cloud Computing and Android OS"; 32nd Annual International Conference of the IEEE EMBS Buenos Aires, Argentina, Aug. 31-Sep. 4, 2010.

*Primary Examiner* — Victoria P Shumate
*Assistant Examiner* — Teresa Williams
(74) *Attorney, Agent, or Firm* — David W. Carstens; Krista Y. Chan; Carstens & Cahooh, LLP

(57) ABSTRACT

A system and method integrating healthcare delivery to patients using data bridges that connect healthcare providers, patients, patient medical education, and patient monitoring devices is disclosed. The system incorporates a mobile user interface device (MUD) allowing user inputs or detected events from a variety of medical instrumentation devices (MID) to be controlled by a healthcare web server computer (HWS) over a computer communication network (CCN). Information retrieved from the MID and transmitted by the MUD to the HWS is then used by a patient healthcare monitor (PHM) process to populate a medical records database (MRD). MRD contents are then matched to patient healthcare plan (PHP) event/time triggers (ETT) that drive information from a provider content database (PCD) to the MUD through the HWS over the CCN. Healthcare provider update/control of the PHP/ETT/PCD allow integration of patient educational materials with patient health status monitoring.

27 Claims, 64 Drawing Sheets

(56) References Cited

U.S. PATENT DOCUMENTS

| | | | |
|---|---|---|---|
| 8,326,651 B2* | 12/2012 | McLaren | G06F 19/322 600/300 |
| 8,396,804 B1* | 3/2013 | Dala et al. | 705/52 |
| 2002/0184055 A1* | 12/2002 | Naghavi et al. | 705/2 |
| 2003/0022141 A1* | 1/2003 | Packard | 434/262 |
| 2004/0039254 A1 | 2/2004 | Stivoric et al. | |
| 2004/0102931 A1* | 5/2004 | Ellis | A61B 5/1038 702/188 |
| 2005/0102160 A1* | 5/2005 | Brown | 705/2 |
| 2005/0283385 A1* | 12/2005 | Hunkeler et al. | 705/2 |
| 2006/0030890 A1* | 2/2006 | Cosentino | A61B 5/00 607/5 |
| 2006/0122469 A1 | 6/2006 | Martel | |
| 2006/0234202 A1 | 10/2006 | Brown | |
| 2007/0006322 A1 | 1/2007 | Karimzadeh et al. | |
| 2007/0015974 A1* | 1/2007 | Higgins | A61B 5/0002 600/300 |
| 2007/0191070 A1* | 8/2007 | Rao | 455/566 |
| 2007/0255345 A1* | 11/2007 | Krause | 607/59 |
| 2008/0077436 A1* | 3/2008 | Muradia | 705/2 |
| 2008/0242947 A1 | 10/2008 | Jung et al. | |
| 2008/0275317 A1* | 11/2008 | Cho | A61B 5/0059 600/310 |
| 2008/0281633 A1 | 11/2008 | Burdea et al. | |
| 2009/0150416 A1 | 6/2009 | Baker et al. | |
| 2011/0029327 A1 | 2/2011 | Dunlop | |
| 2011/0166884 A1 | 7/2011 | Lesselroth et al. | |
| 2011/0234409 A1* | 9/2011 | Soliman | 340/573.1 |
| 2011/0238435 A1 | 9/2011 | Rapaport et al. | |
| 2011/0295621 A1* | 12/2011 | Farooq et al. | 705/3 |
| 2012/0041771 A1 | 2/2012 | Cosentino et al. | |
| 2012/0183941 A1 | 7/2012 | Steinmetz | |
| 2012/0203573 A1 | 8/2012 | Mayer et al. | |
| 2013/0035955 A1* | 2/2013 | Torres | 705/3 |
| 2013/0262155 A1* | 10/2013 | Hinkamp | G06Q 40/08 705/4 |
| 2013/0329058 A1 | 12/2013 | Brossette et al. | |
| 2013/0339060 A1* | 12/2013 | Delaney et al. | 705/3 |
| 2016/0006946 A1 | 1/2016 | Cohen et al. | |

* cited by examiner

Survey History

From Date: 12/7/2013    To Date: 3/7/2014    Get Survey    Export

| Date/Time | Alert | Group | Question | Answer |
|---|---|---|---|---|
| 12/20/2013 12:24 | | Congestive Heart Failure | What is the inside of an artery called? | Lumen |
| 12/20/2013 12:24 | | Congestive Heart Failure | Please watch - inside an Artery | Now |
| 12/20/2013 12:24 | | Congestive Heart Failure | Did you take all of your medicines yesterday? | Yes |
| 12/20/2013 12:24 | | Congestive Heart Failure | Did you notice an increase in swelling in hands, feet or ankles? | No |
| 12/20/2013 12:24 | | Congestive Heart Failure | Did you sleep in a chair or propped up on extra pillows last night? | No |
| 12/20/2013 12:24 | Medium | Congestive Heart Failure | While performing activities, how is your breathing? | Short of breath |
| 12/20/2013 12:24 | | Congestive Heart Failure | While at rest, how is your breathing? | A little short of breath. |

Page size: 15    7 items in 1 page(s)

Profile History

| Date | History | Caregiver |
|---|---|---|
| 01/22/2014 11:13 | Patient Monitoring Status updated to "Deleted". Reason: done | Robin Hill |
| 12/20/2013 12:29 | kit "DEMO011" unassigned | Robin Hill |

| | COPD | Depression | Diabetes | Heart Failure | Hyperlipidemia | Hypertension | Ischemic Heart Disease | Osteoporosis | Stroke |
|---|---|---|---|---|---|---|---|---|---|
| | No | No | | No | No | No | No | No | No |
| | Yes | Yes | | Yes | Yes | Yes | Yes | Yes | Yes |

| Depression | | Rarely | Sometimes | Often | Most of the time |
|---|---|---|---|---|---|
| I experience feelings of sadness or the blues. | | | ■ | | |
| I have feelings of helplessness about the future. | | | | ■ | |
| I have little interest or pleasure in doing things. | | | ■ | | |
| I have trouble sleeping many nights. | | | | | ■ |

| | Never / Almost Never | Occasionally | Often | Very Often | Always / Almost Always |
|---|---|---|---|---|---|
| Stress Management | | | | | |
| I feel my level of stress is manageable for me. | | | | | ▓ |
| When I feel stressed, lonely, angry, or in need of help I have someone I can call. | | | | ▓ | |
| In general, I feel satisfied with my life, i.e. home life, work life, social life, etc. | | ▓ | | | |
| Values, Spirituality and Beliefs | | | | | |
| I feel that my life has a purpose. | | | | ▓ | |
| I am able to discuss my values and beliefs with my family and friends in a reasonable manner. | ▓ | | | | |
| My actions are guided by my own beliefs rather than the beliefs of others. | | | | ▓ | |
| I spend a portion of every day in personal reflection. | | ▓ | | | |

FIG. 62

| 6200 | Never / Almost Never | Occasionally | Often | Very Often | Always / Almost Always |
|---|---|---|---|---|---|
| Medications | | | | | |
| I understand all of my medications and the importance of taking each one. | | | ■ | | |
| I clearly understand the possible side effects of each of my medications. | | | | | ■ |
| Understanding of Care | | | | | |
| I agree with my health goals and how I can reach each goal. | ■ | | | | |
| My preferences were taken into account when deciding my health care needs. | | | | ■ | |
| I am confident about managing my health care needs. | ■ | | | | |

Save Form

FIG. 63

| Patient Questions | Strongly Disagree | Disagree | Agree | Strongly Agree | Don't know or N/A |
|---|---|---|---|---|---|
| I'm too busy with other activities, i.e. work, family or friends, to care for myself. | | | | ■ | |
| I would rather spend any free time I have doing things I really enjoy rather than exercising. | | ■ | | | |
| Caring for others is a higher priority to me than focusing on my own health care needs. | | | | ■ | |
| It's not always easy for me to get to the pharmacy to fill or refill my medications. | ■ | | | | |
| I could take better care of myself if it didn't cost so much. | | | | | ■ |
| I prefer to spend my time relaxing, whether with friends or not, instead of spending time exercising or preparing healthy meals. | ■ | | | | |

Completed on 02/27/2014 by Kevin Klughart

- I'm set in my ways, and I don't like to change my habits even when I know they aren't good for my health.
- It's hard to eat healthy or exercise when others I live with aren't doing the same.
- I know I'm buying the right foods when I buy things that are labeled "healthy" or "low fat."
- I don't think I need to be on as much medication as my doctor has prescribed.
- I can't exercise because I have physical limitations.
- Where I live makes it really hard to live healthy.
- I already do everything I can to live healthy.
- There isn't anything I can do differently to help my health.
- I have trouble remembering when to take my medications.

HEALTHCARE DELIVERY SYSTEM AND METHOD

CROSS REFERENCE TO RELATED APPLICATIONS

U.S. Provisional Patent Applications

This application claims benefit under 35 U.S.C. §119 and incorporates by reference United States Provisional Patent Application for HEALTHCARE MANAGEMENT SYSTEM AND METHOD by inventor Eric Rock, filed electronically with the USPTO on Mar. 26, 2013, with Ser. No. 61/805,355, EFS ID 15358332, confirmation number 6386.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for integrating healthcare delivery to patients via computerized systems and methods that allow multiple healthcare providers to interact with remote patients and healthcare monitoring equipment to provide unified healthcare services to the patient.

Without limiting the scope of the present invention, the general field of invention scope may fall into one or more U.S. patent classifications including: 705/3; 705/2; and 600/300.

PRIOR ART AND BACKGROUND OF THE INVENTION

Prior Art System Context (0100)

As depicted in FIG. 1 (0100), a conventional healthcare delivery system model may incorporate a hospital (0110) or other healthcare facility that includes a care management team (0111) comprising a number of healthcare providers (doctors, nurses, physician assistants, etc.) (0112, 0113). This care management team interacts via a user interface (0114) with a hospital information system (HIS) (0115) computer system running software read from a computer readable medium (0116) to populate patient data in an electronic medical record (EMR) database (0117). Interaction with patients (0120) may initially occur on an in-patient basis (0121) and progress to an out-patient basis (0122) once the patient is discharged from the medical facility (0110). Prior to discharge, billing analysis may provide information on patient risk stratification as it relates to the potential for the patient to be readmitted due to declining health status post-discharge. After discharge, the patient may interact with a healthcare provider (0130) comprising a caregiver (nurse, aid, etc.) (0131) to receive a variety of out-patient services. This caregiver (0131) may interact with a computer interface (0132) to log patient information, but this additional information is invariably relayed to the care management team (0111) via the use of telephone, fax, or some other communication mechanism that is incompatible with the HIS (0115) system and the EMR (0117) database.

Within this healthcare delivery context, a significant problem exists in that while the patient (0120) may be fully monitored while being treated by the care management team (0111), once the patient (0120) progresses from in-patient (0121) to out-patient (0122) status, healthcare delivery is often reduced in quality because it is impossible to adequately monitor the patient (0120) once the patient (0120) transitions from in-patient (0121) to out-patient (0122) and leaves the confines of the hospital (0110) or other healthcare provider. Furthermore, the healthcare provider (0130) may comprise a number of unrelated healthcare professionals such as doctors and specialists that may not communicate with each other (or the hospital (0110)). This disconnected nature of healthcare delivery often results in patients (0120) regressing in health after leaving the hospital (0110) and requiring readmission to the hospital (0110) for follow-up treatment. This follow-up treatment is typically much more expensive than monitored or preventative care delivered by a healthcare provider (0130).

An additional issue with this model of healthcare delivery is the fact that risk stratification analytics (0119) relating to the delivery of healthcare to the patient (0120) are determined AFTER the patient has progressed from in-patient (0121) to out-patient (0122) status. This is typically accomplished by inspecting billing records for the patient (0120) while in the in-patient (0121) state and determining the risk of patient relapse or readmission to the hospital (0110) based on predefined coded diagnoses (International Classification of Diseases (ICD) or Diagnosis-Related Group (DRG)) assigned to the patient. This ICD/DRG information may statically be applied to a risk stratification algorithm to determine a service priority for the patient to minimize the risk of readmission for the patient as well as minimizing the hospital cost for the patient readmission. However, once the patient (0120) leaves (0122) the hospital (0110) confines the patient health state may change radically and it is not possible for this information to be incorporated into the HIS (0115) for use by the care management team (0111) to determine what if any additional healthcare should be directed towards the discharged patient (0122). Furthermore, it is impossible once the patient (0120) leaves (0122) the hospital (0110) for patient healthcare given by healthcare providers (0130) to be integrated into risk stratification methodologies incorporated into the HIS (0115) and used by the care management team (0111) to direct healthcare to the patient (0120). In summary, once the patient leaves the confines of the hospital environment the healthcare given to the patient is uncontrolled and for the most part unmonitored.

Prior Art Methodology (0200)

The prior art system context as depicted in FIG. 1 (0100) is typically associated with a prior art methodology as depicted in FIG. 2 (0200) and involves the following steps:

(1) The patient is processed into the hospital or medical facility via an in-patient visit (0201);

(2) Patient information is entered into a hospital information system (HIS) as an electronic medical record (EMR) database (0202);
(3) The patient is treated by healthcare professionals who log ICD/DRG diagnosis/treatment codes into the EMR as the patient is treated (0203);
(4) The patient is discharged from the hospital and a billing record is generated (0204);
(5) A significant time delay occurs between patient discharge and the analysis of the patient with respect to risk stratification that determines the patient risk for re-admission to the hospital (0205);
(6) Patient billing records are processed using a risk stratification methodology to determine (based on ICD/DRG codes and patient demographics) which patients pose a risk for readmission to the hospital (0206);
(7) The patient care management team (CMT) is informed of potential at-risk patients who may require readmission to the hospital if not properly monitored after discharge (0207); and
(8) The patient CMT coordinates with outside healthcare providers via telephone/fax to interact with the patient in an attempt to minimize the risk of patient re-admission to the hospital (0208).

While a number of different variations on this methodology may exist in various healthcare environments, the basic problem with this methodology is that it statically determines the at-risk patients based on an analysis of ICD/DRG codes and other information as part of the billing cycle. Note that this billing cycle is typically performed at or after discharge of the patient from the hospital and does not occur while the patient is being treated at the hospital. As such, there is no methodology in this process flow to account for changes in patient risk stratification while the patient is being treated at the hospital.

Additionally, information concerning at-risk patients once statically determined is never updated based on changing patient status after discharge from the hospital. Finally, it is not possible to economically deploy healthcare professionals in the field to perform the necessary patient monitoring required to update patient at-risk status once discharge from the hospital has occurred. As a result, many patients experience a decline in health status after leaving the hospital because there is little or no medical feedback to the CMT or other healthcare providers as to the actual condition of the patient.

Deficiencies in the Prior Art

The prior art as detailed above suffers from the following deficiencies:
Prior art healthcare delivery systems and methods do not perform patient risk stratification while the patient is being treated at the hospital or medical facility.
Prior art healthcare delivery systems and methods do not dynamically collect patient information for risk stratification while the patient is in the hospital environment.
Prior art healthcare delivery systems and methods do not dynamically determine patient risk stratification.
Prior art healthcare delivery systems and methods do not accurately determine at-risk patients once these patients leave the hospital environment.
Prior art healthcare delivery systems and methods do not coordinate patient data between outside healthcare providers and the hospital HIS/EMR systems.
Prior art healthcare delivery systems and methods are generally unaware of changes in patient vital statistics after the patient has left the hospital environment.
Prior art healthcare delivery systems and methods lack interaction with the patient for the purposes of determining changes in patient status or behavior.
Prior art healthcare delivery systems and methods lack any mechanisms to link patient care with patient education.

While some of the prior art may teach some solutions to several of these problems, the core issue of integrating healthcare remotely among various healthcare providers in an effort to reduce patient re-admissions has not been solved by the prior art.

OBJECTIVES OF THE INVENTION

Accordingly, the objectives of the present invention are (among others) to circumvent the deficiencies in the prior art and affect the following objectives in the context of a healthcare delivery system and method:
(1) Provide for a healthcare delivery system and method that performs patient risk stratification while the patient is being treated at the hospital or medical facility.
(2) Provide for a healthcare delivery system and method that dynamically collects patient information for risk stratification while the patient is in the hospital environment.
(3) Provide for a healthcare delivery system and method that dynamically determines patient risk stratification.
(4) Provide for a healthcare delivery system and method that accurately determines at-risk patients once these patients leave the hospital environment.
(5) Provide for a healthcare delivery system and method that coordinates patient data between outside healthcare providers and the hospital HIS/EMR systems.
(6) Provide for a healthcare delivery system and method that is generally aware of changes in patient vital statistics after the patient has left the hospital environment.
(7) Provide for a healthcare delivery system and method that interact with the patient for the purposes of determining changes in patient status or behavior.
(8) Provide for a healthcare delivery system and method that include mechanisms to link patient care with patient education.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention as embodied in a system and method utilizes a number of interconnected computers to affect the following coordination of patient healthcare:
Mobile user devices (MUD) interact with the patient and collect healthcare information from a variety of wireless patient monitoring medical instrumentation devices (MID).
A centralized healthcare web server computer (HWS) interacts with the MUD over a computer communications network (CCN) and interfaces with a variety of data bridges to healthcare provider computers (HIS systems) to coordinate patient interaction, MID data collection, and physician treatment of the patient.

Event/time triggers associated with a given patient and/or MID data collection drive presentation of content to the patient and permit collection of additional information that is defined by a patient healthcare plan (PHP) to coordinate patient care.

Web applications to caregivers provide access to patient reports and permit caregivers to trigger predefined PHP events for execution by the MUD.

Background analysis of MID patient data in conjunction with collection of patient information permit risk stratification of patients and trigger reports to healthcare providers and caregivers to allow rapid adjustment of PHP events to affect optimal patient care.

Real-time analysis of HIS information as collected from the patient in a hospital or medical delivery environment is continually analyzed to risk stratify patients and permit patient care management teams to be visually notified via status dashboards of potential at-risk patients.

This system may be combined with a healthcare delivery method used to affect integration of healthcare for a given patient among a variety of caregiver and hospital resources.

BRIEF DESCRIPTION OF THE DRAWINGS

For a fuller understanding of the advantages provided by the invention, reference should be made to the following detailed description together with the accompanying drawings wherein:

FIG. 38 illustrates an exemplary patient survey and profile history web browser screenshot;

FIG. 51 illustrates an exemplary direct patient data entry dialog;

FIG. 52 illustrates an exemplary patient demographic data entry dialog;

FIG. 54 illustrates an exemplary RISK STRATIFICATION data entry dialog interface (part 2/4);

FIG. 57 illustrates an exemplary HEALTH ASSESSMENT data entry dialog interface (part 1/6);

FIG. 61 illustrates an exemplary HEALTH ASSESSMENT data entry dialog interface (part 5/6);

FIG. 62 illustrates an exemplary HEALTH ASSESSMENT data entry dialog interface (part 6/6);

FIG. 63 illustrates an exemplary BARRIERS TO CARE data entry dialog interface (part 1/2); and FIG. 64 illustrates an exemplary BARRIERS TO CARE data entry dialog interface (part 2/2).

DESCRIPTION OF THE PRESENTLY PREFERRED EXEMPLARY EMBODIMENTS

Figure 1:
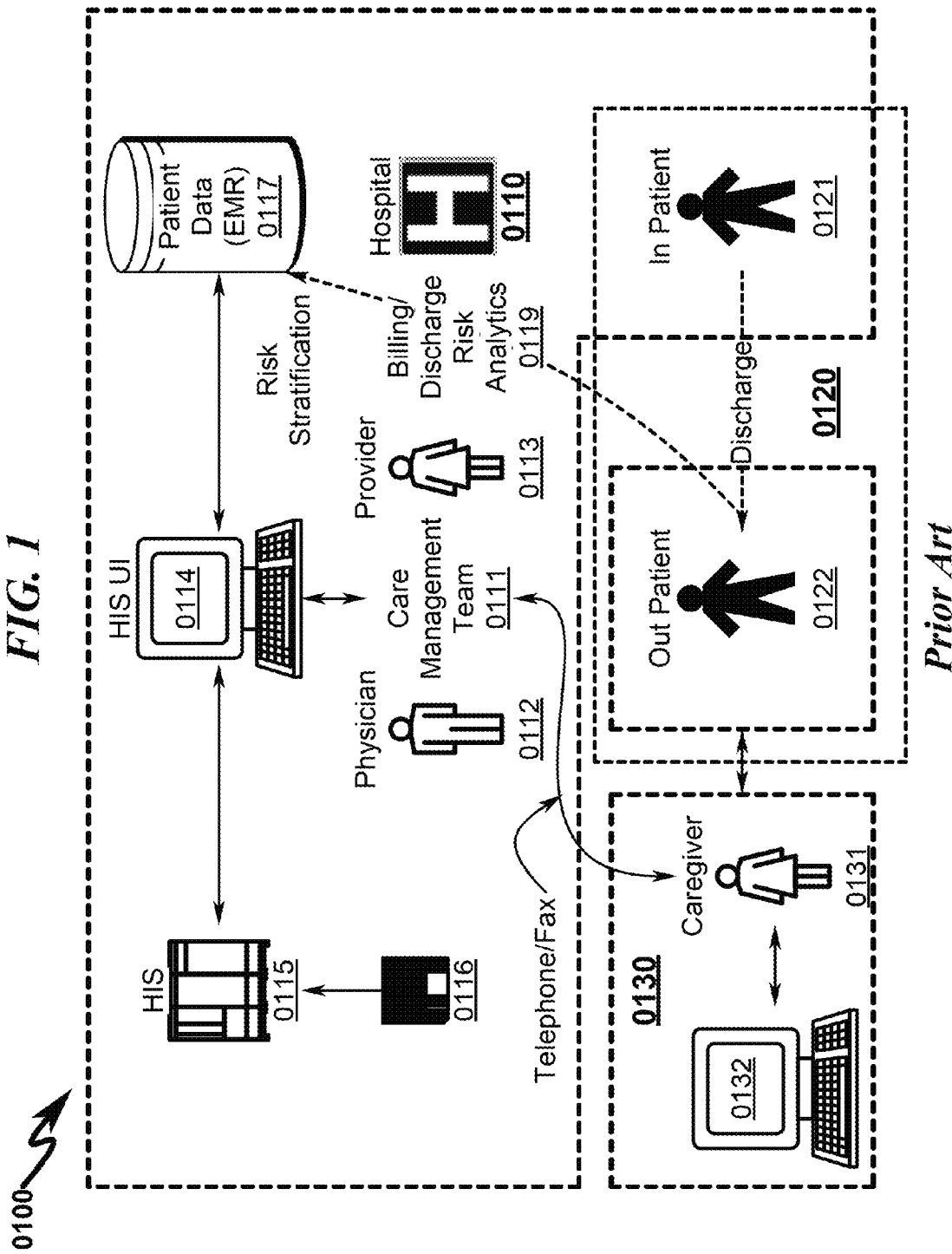
FIG. 1 illustrates an exemplary prior art healthcare delivery system context.
Figure 2:
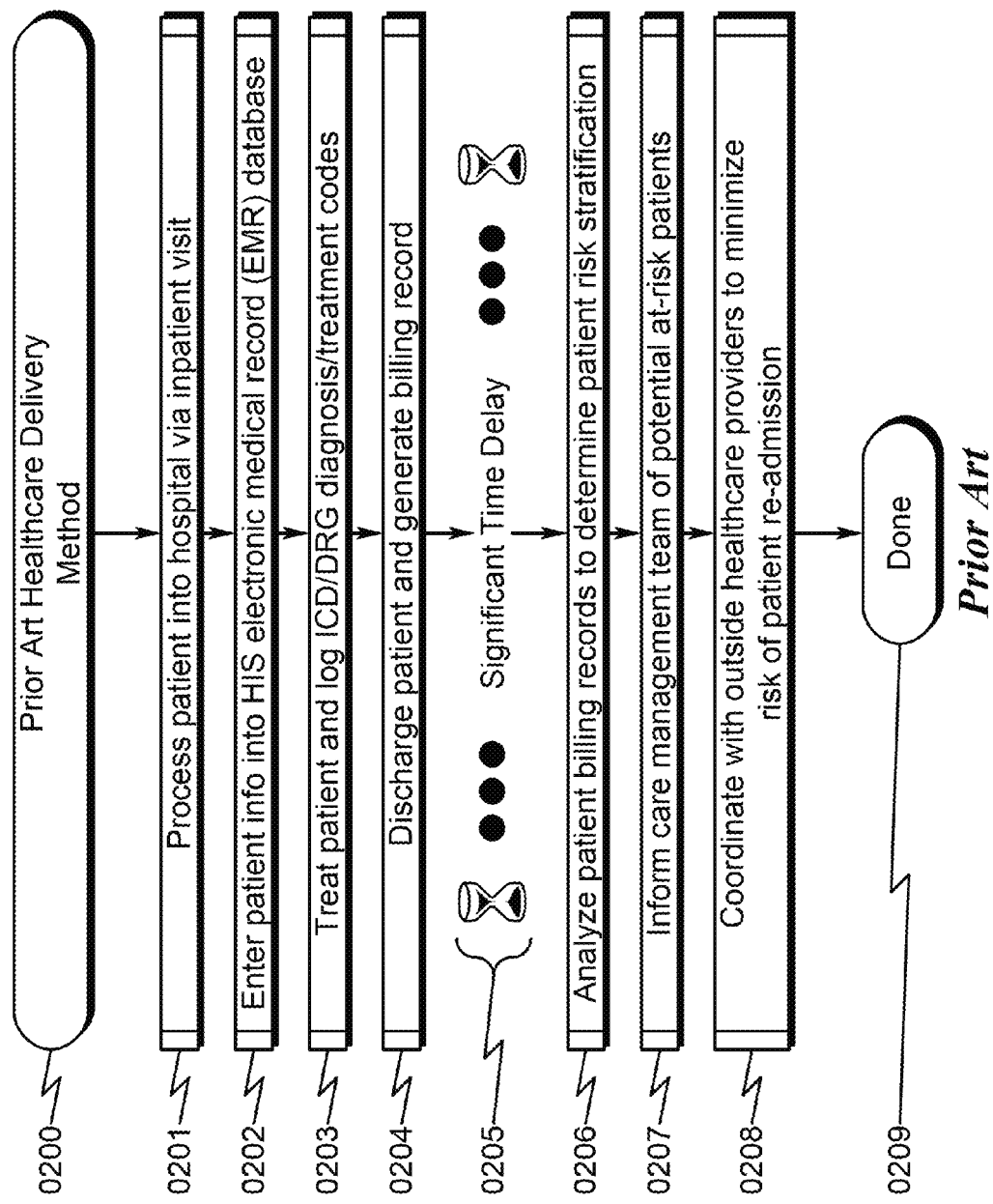
FIG. 2 illustrates an exemplary prior art healthcare delivery method.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a HEALTHCARE DELIVERY SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

System Overview (0300)

Figure 3:
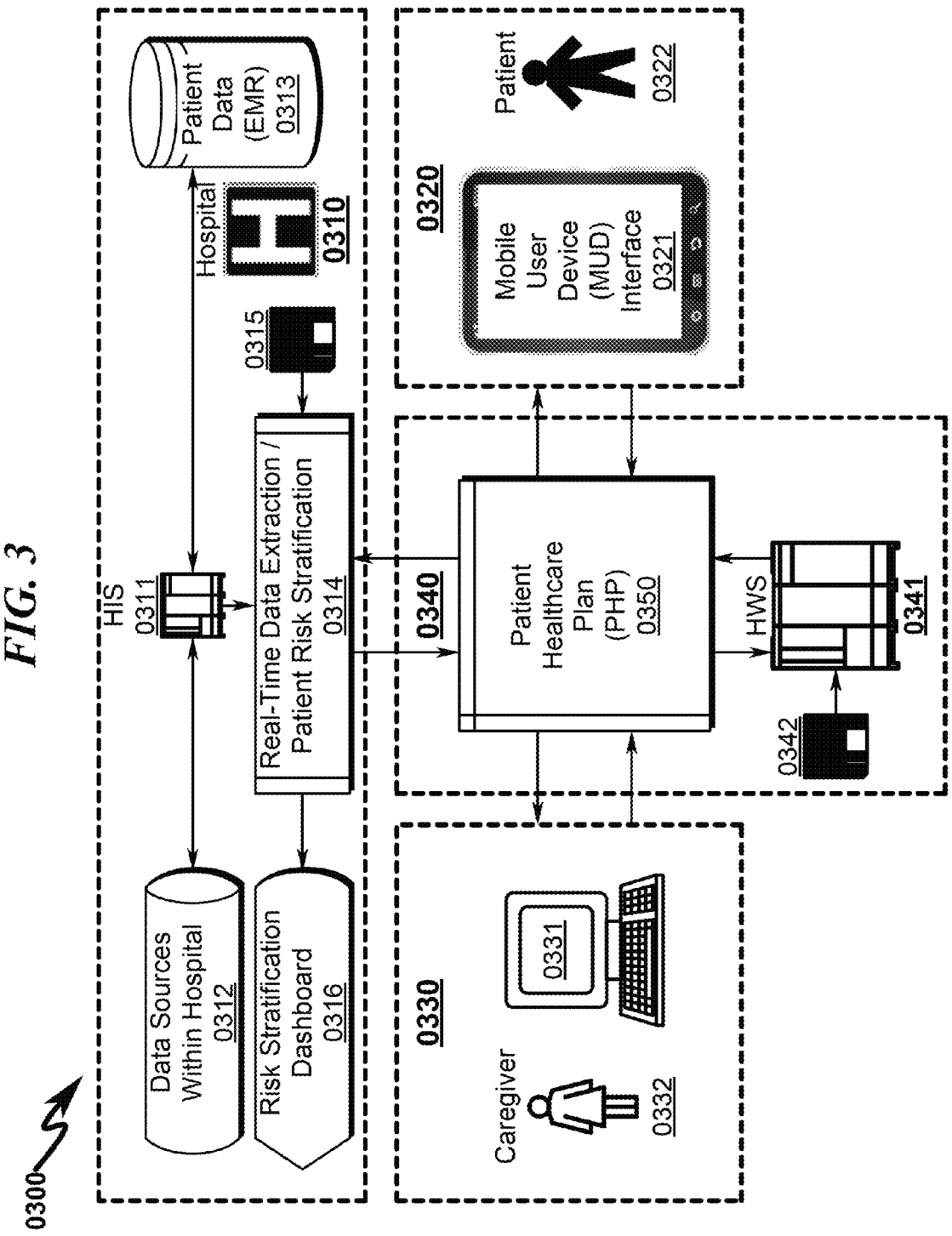
FIG. 3 illustrates a preferred exemplary overview block diagram of a preferred exemplary system embodiment of the present invention.

The present invention may be summarized as depicted in the system block diagram of FIG. 3 (0300), and is comprised of four cooperating computer systems as depicted by the HIS system (0310), patient remote monitoring system (0320), caregiver computer system(s) (0330), and healthcare web server (HWS) (0340). Within this context the system operates to integrate information from the various computer systems (0311, 0321, 0331, 0341) as dictated by an overarching patient healthcare plan (PHP) (0350) executed as machine instructions read from a computer readable medium (0342) that drives information flow between the various computer systems (0311, 0321, 0331, 0341).

A core concept in this architecture is that the PHP (0350) is configurable by healthcare providers from the hospital (0310) or other medical facility care management team members to continually drive real-time healthcare dashboard status information to authorized healthcare provider recipients based on real-time patient information collected from remote monitoring devices (RMD) communicating with mobile user devices (MUD) (0321) as well as information gathered from patient caregiver interfaces (0331) and information collected from real-time data extraction processes (0314) operating within the HIS (0311) environment. Since current healthcare methodologies isolate the HIS (0311) system within the context of a defined hospital (0310) healthcare environment, coordination of information among healthcare professionals after the patient leaves this environment has been problematic. By providing a healthcare web server (HWS) (0340) incorporating web portals accessible by the authorized healthcare providers, the system as depicted permits a unified patient healthcare plan (PHP) (0350) to act as the driver for the delivery of healthcare to the patient as well as the hub for reporting patient status to all interested and authorized healthcare professionals servicing the patient.

Within the context of the hospital setting (0310), data is continually collected by the healthcare information system (HIS) (0311) computer from a wide variety of data sources (0312) such as lab results, patient history information, chart diagnoses, procedures, surgeries, patient vital signs, etc. This information normally flows directly from the data sources (0312) to the HIS (0311) (via manual or automated input) and is collected for deposit within the patient electronic medical record (EMR) database (0313). The present invention inserts a software module (0314) (as executed machine instructions read from a computer readable medium (0315)) in this HIS (0311) context to sniff these data flows and extract information associated with various patients. This real-time patient data is then used as input to the patient healthcare plan (PHP) (0350) to drive patient care and also as input to a real-time process (0314) configured to risk stratify patients before and after they leave the hospital (0310) setting. This permits the care management team or other healthcare providers to have a real-time risk stratification dashboard (0316) that allows at-risk patients to be immediately identified for additional care or modifications to their PHP (0350). This is in contrast to prior art systems that are unable to gather patient data across various physician-care boundaries and integrate this information into a coherent risk stratification analysis.

By integrating in-patient information, out-patient information, and information gathered from various healthcare providers (0332), it is possible to immediately address declines in patient health with proactive measures rather than waiting until these conditions reach a critical stage necessitating readmission of the patient (0322) to the hospital (0310). Additionally, within the hospital (0310) context, the real-time integration of patient care information permits a real-time risk stratification dashboard (0316) to be created that allows hospital and care management staff the ability to allocate their limited resources to patients at the greatest risk of a severe medical event.

It is informative to note that less than 5% of the patient population account for 50% of the cost of patient care. Among this group, annual medical expenses equaled or exceeded USD$11487 per person. In contrast, the 50% of the population with the lowest healthcare expenses accounts for only about 3% of overall U.S. medical spending, with an annual medical spending below USD$664 per person. Thus, those in the top 5% of healthcare utilization spent on average more than 17 times as much per person as those in the bottom 50% of healthcare spenders. From this data it is clear that allocating resources optimally to at-risk patients can have a significant impact on the overall cost of healthcare within the hospital (0310) environment. The present invention permits the hospital (0310) and other healthcare professionals (0332) the ability to maintain a real-time status dashboard of patient medical conditions and within this framework address at-risk patients immediately to minimize their overall cost to the healthcare delivery system.

Method Overview (0400)

Figure 4:
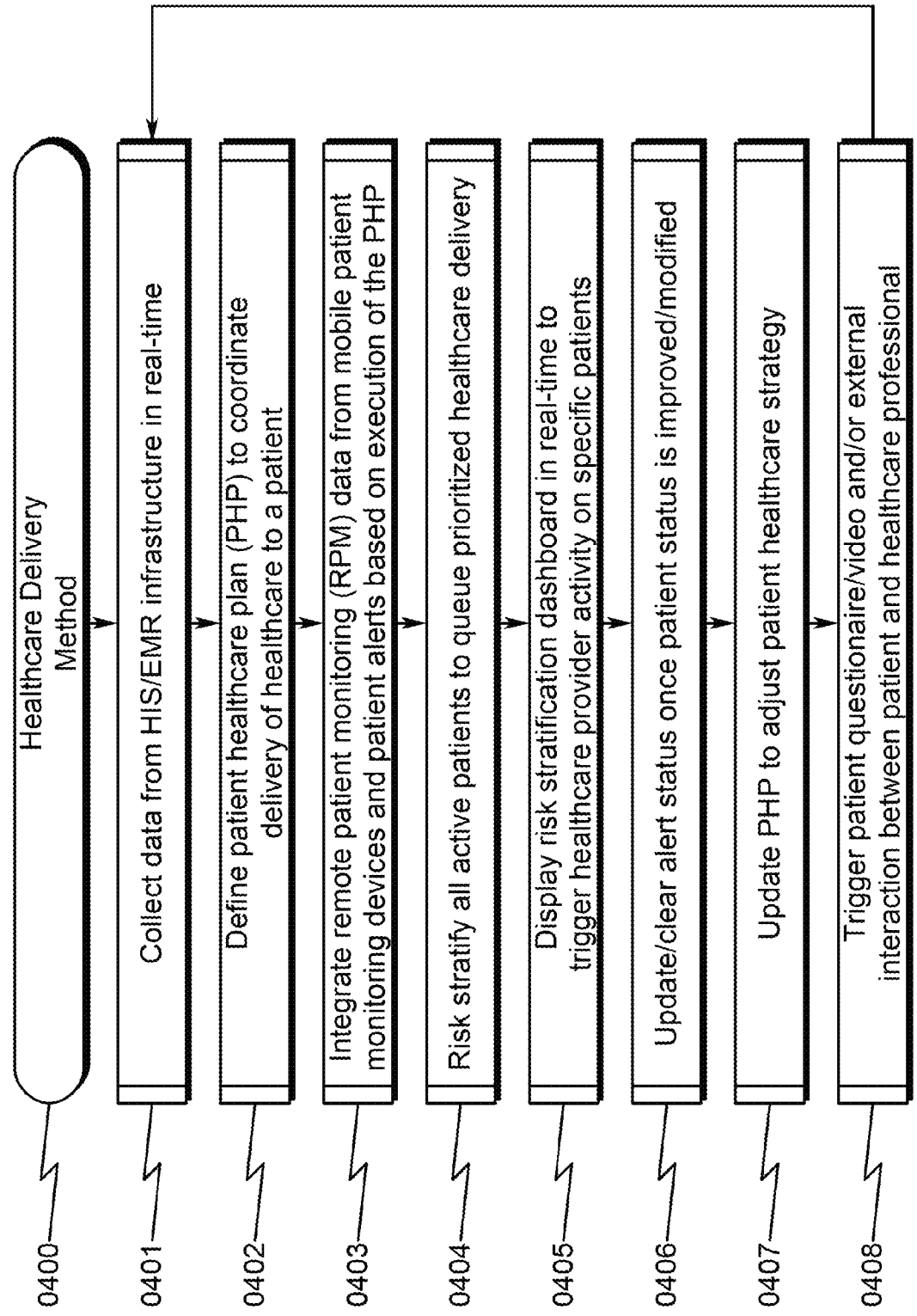
FIG. 4 illustrates a preferred exemplary overview flowchart of a preferred exemplary method embodiment of the present invention.

Associated with the exemplary system overview described in FIG. 3 (0300) is a healthcare delivery method as depicted in FIG. 4 (0400) that comprises the following steps:
(1) Collecting patient data in real-time within a HIS/EMR infrastructure (0401);
(2) Allowing definition of a patient healthcare plan (PHP) that coordinates delivery of healthcare to a patient (0402);
(3) Integrating remote patient monitoring (RPM) data from mobile patient monitoring devices and patient alerts based on execution of the PHP (0403);
(4) Risk stratifying all active patients to queue prioritized healthcare delivery to patients (0404);
(5) Displaying risk stratification dashboards in real-time to trigger healthcare provider activity on specific patients (0405);
(6) Updating/clearing alert status once patient status is improved/modified (0406);
(7) Allowing the PHP be updated to adjust patient healthcare strategy based on patient alerts (0407); and
(8) Triggering patient questionnaires/video and/or external interaction between the patient and healthcare professionals based on alerts generated by the PHP and then proceeding to step (1) (0408).
One skilled in the art will recognize that these method steps may be augmented or rearranged without limiting the teachings of the present invention. This general method summary may be augmented by the various elements described herein to produce a wide variety of invention embodiments consistent with this overall design description.

System Detail Overview (0500)

Figure 5:
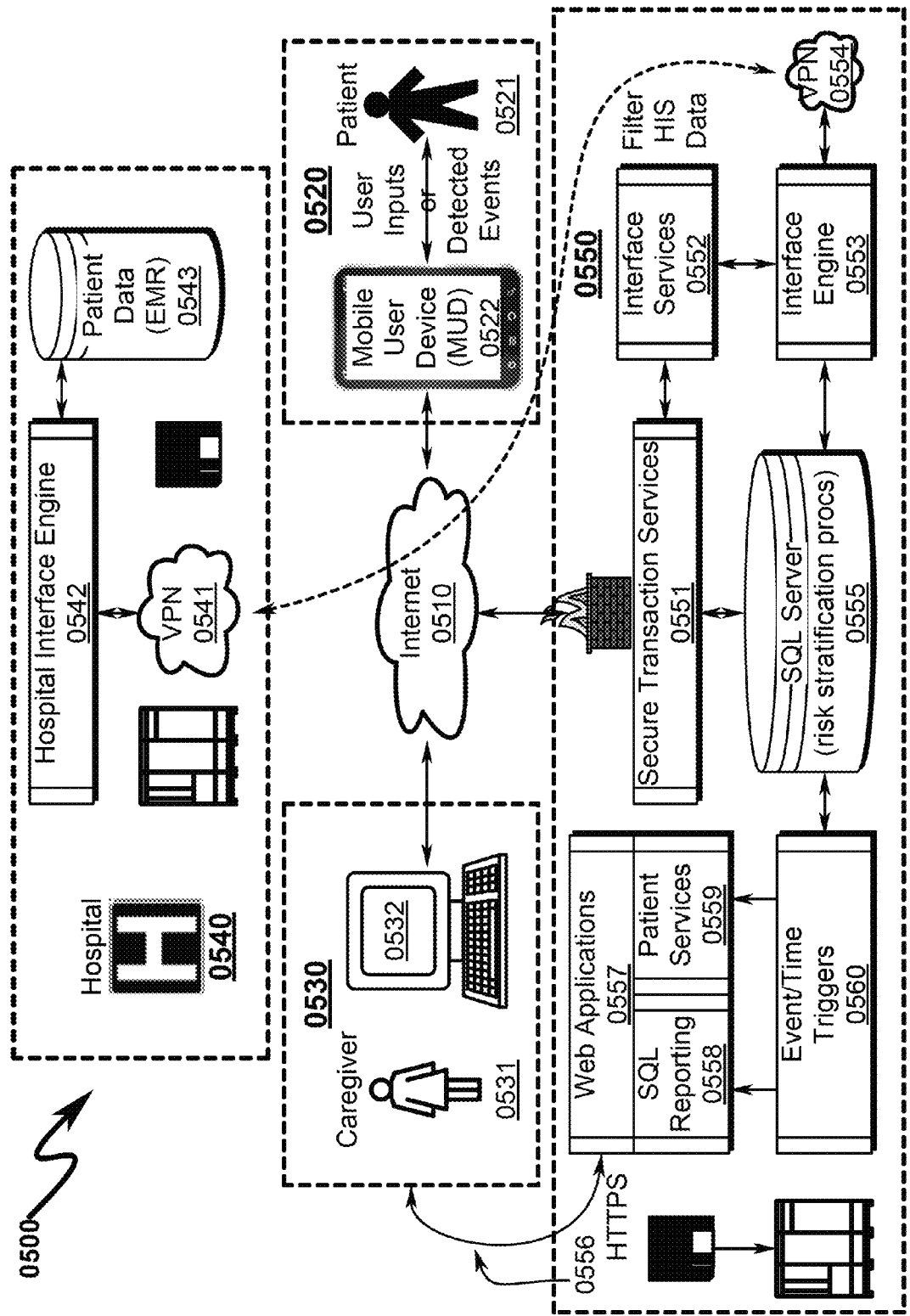
FIG. 5 illustrates a preferred exemplary data flow block diagram of a preferred exemplary system embodiment of the present invention.

The present invention in various embodiments addresses one or more of the above objectives in the following manner as generally depicted in FIG. 5 (0500). This exemplary system embodiment is linked by a computer communications network (CCN) (0510) (typically the Internet) and consists of four separate interconnected computer systems:

Patient Portal (0520). This interface permits a patient (0521) interacting with a mobile user device (MUD) (0522) to collect medical and other information about the patient (0521) for analysis by other system components. The MUD (0522) may also be utilized in various applications to provide educational materials to the patient (0521).

Caregiver Portal(s) (0530). This interface permits a healthcare provider (0531) (healthcare specialist, doctor, nurse, etc.) to interact with a computer system (0532) to obtain current status concerning the patient (0521) and any medical information collected by the MUD (0522). This information also permits a coordinated patient healthcare plan (PHP) to be coordinated among a number of different independently operating healthcare providers (0531).

Hospital Portal (0540). This interface permits an independently operating hospital to interact with the system via a virtual private network (VPN) (0541) to permit a hospital data interface (0542) to allow transparent access to and updating of patient healthcare data (electronic medical records) (EMR) (0543). In this manner, a hospital may integrate their existing EMR systems with healthcare providers (0531) and MUD (0522) instrumentation in a transparent manner.

Healthcare Web Server (HWS) (0550). This coordinating computer interface (also termed a healthcare computing device (HCD)) provides for a protected interface to secure transaction services (STS) (0551) that acts to coordinate data transfers between the various other system components to permit seamless integration of real-time patient medical data (0520) and healthcare plans among the healthcare providers (0530) and hospitals (0540). The STS (0551) process interacts with interface services (0552) that are specific to the various other computer systems. An interface engine (0553) is used to communicate (0554) with the MUD (0522) patient data which is then stored in a database using a SQL server (0555) (and associated data-driven risk stratification procedures). Healthcare providers (0531) interact with the HWS (0550) through a secure communication channel (0556) using one or more web applications (0557) that access SQL reporting processes (0558) or patient interface services (0559). Associated with the SQL reporting (0558) and patient services (0559) are event/time triggers (0560) that may be set by a patient healthcare plan (PHP) defined by the caregiver interface (0530) or hospital (0540). These event/time triggers (0560) are designed to inspect data collected from the patient (0521) in real-time from the MUD (0522) and trigger alerts and real-time medical status displays (0532) to healthcare providers (0531) and/or the hospital (0540) based on monitored patient healthcare data.

All of these systems (0520, 0530, 0540, 0550) are designed to operate in the context of one or more computer systems executing instructions from a computer readable medium. In the case of the HWS (0550), the secure transaction services (0551) interface and communication interfaces (0554, 0556) provide transparent interfaces to the other various computer systems through the CCN (0510). This enables existing infrastructures that deal with patient healthcare information to be updated with new patient data as it is collected from the MUD (0522) and also receive dashboard status displays and alerts from the event/time triggers (0560) concerning various patient related medical conditions. Note also that the event/time triggers (0560) may be activated by patient healthcare plan (PHP) information collected from the healthcare providers (0530) or hospitals (0540) to trigger collection of medical information from the patient, educational materials to be provided to the patient, activity to be requested from the patient, or other events that do not involve activity by the healthcare providers (0530) or hospitals (0540). This allows the PHP to independently direct patient monitoring and other activity without the need for direct healthcare provider/hospital monitoring.

One skilled in the art will recognize that the various embodiments depicted herein may be combined to produce a variety of system configurations consistent with the teachings of the invention.

Method Detail Overview (0600)

Figure 6:
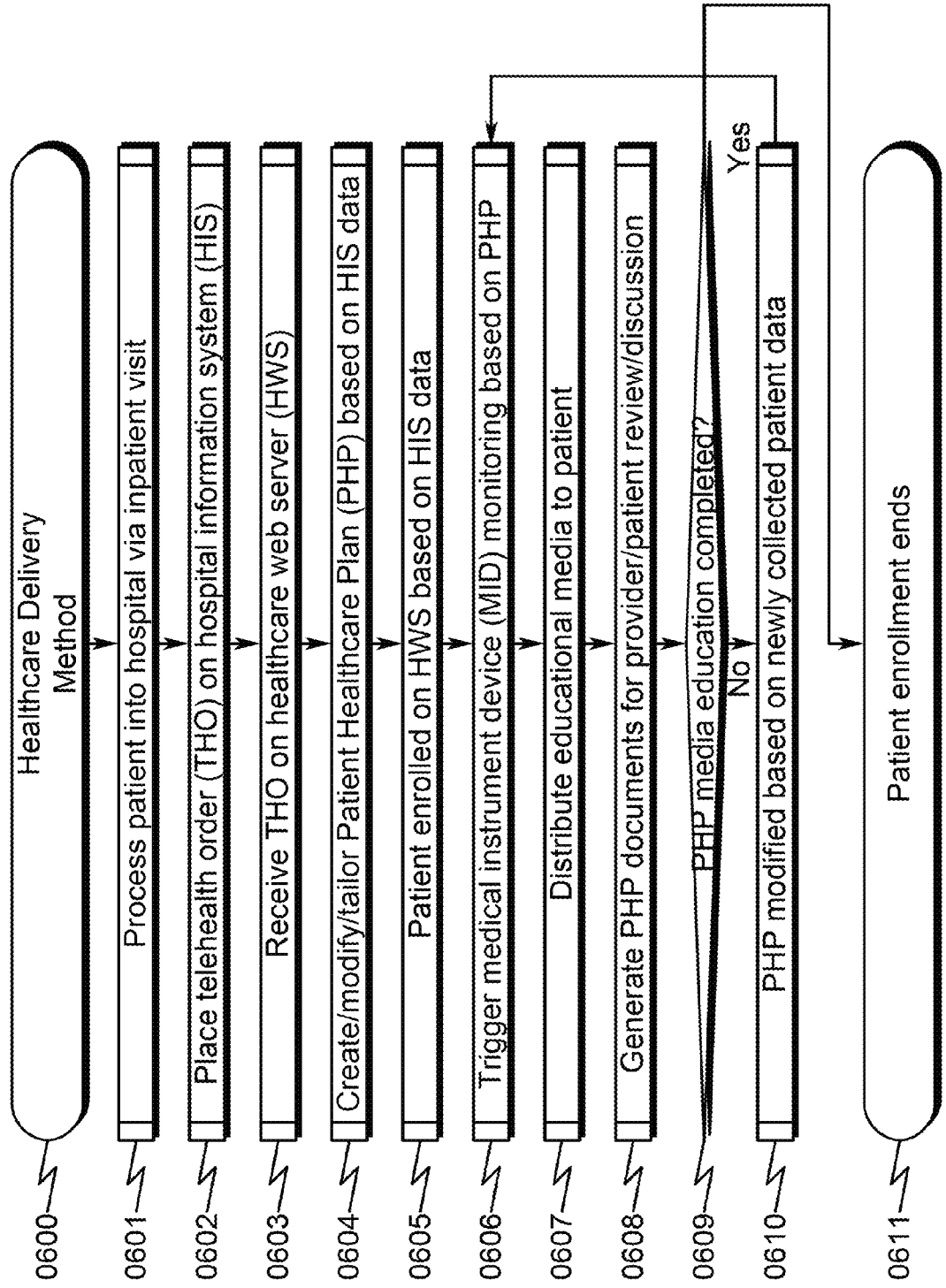
FIG. 6 illustrates a preferred exemplary flowchart of a preferred exemplary method embodiment of the present invention.

Associated with the exemplary system overview described in FIG. 5 (0500) is a healthcare delivery method as depicted in FIG. 6 (0600) that comprises the following steps:

(1) Processing a patient into a hospital or other healthcare service setting via an in-patient visit (0601);
(2) Placing a telehealth order (THO) on the hospital information system (HIS) for the patient (0602);
(3) Receiving the THO on a remote healthcare web server (HWS) (0603);
(4) Creating/modifying/tailoring a patient healthcare plan (PHP) on the HWS based on HIS data received in the THO (0604);
(5) Enrolling the patient on the HWS based on HIS data received (0605);
(6) Triggering medical instrument device (MID) monitoring of the patient based on the PHP (0606);
(7) Distributing medical educational media to the patient based on the PHP via the MUD (0607);
(8) Generating PHP documents for healthcare provider/patient review and discussion (0608);
(9) Determining if PHP media education has been completed, and if so, proceeding to step (11) (0609);
(10) Modifying the PHP based on newly collected patient data and/or alerts then proceeding to step (6) (0610); and
(11) Ending the patient enrollment on the HWS (0611).

One skilled in the art will recognize that these method steps may be augmented or rearranged without limiting the teachings of the present invention. This general method summary may be augmented by the various elements described herein to produce a wide variety of invention embodiments consistent with this overall design description.

Healthcare Delivery Information Flow (0700)

Figure 7:
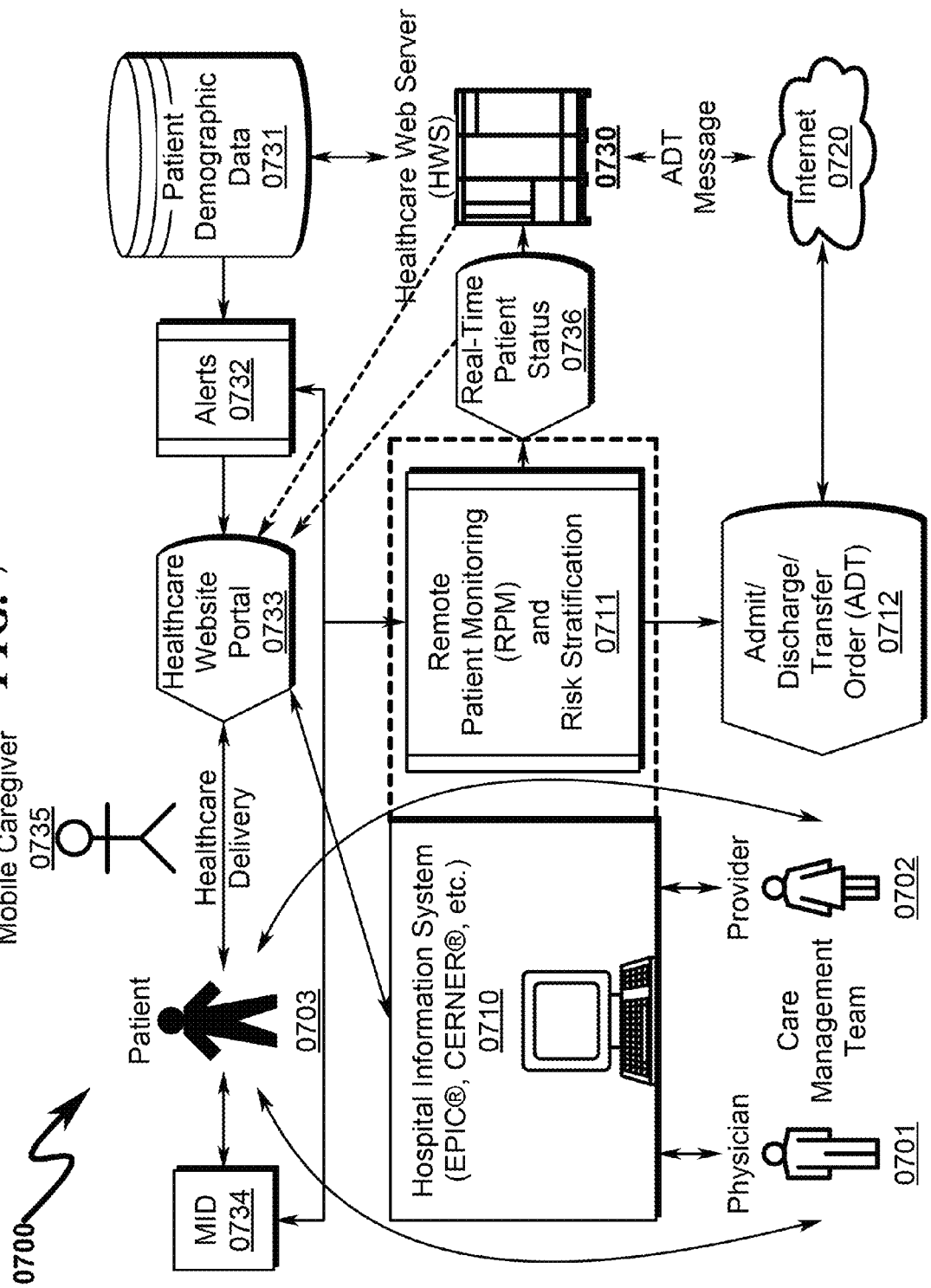
FIG. 7 illustrates a preferred exemplary data flow block diagram of a preferred exemplary system embodiment of the present invention depicting alert message integration with Hospital Information System (HIS) infrastructures.

Within the context of the present invention, a healthcare delivery information flow as depicted in FIG. 7 (0700) permits integration of in-patient/out-patient and patient alerts to be simultaneously processed. In this example, a care management team comprising a physician (0701) and/or healthcare provider (0702) interact with a hospital information system (HIS) (0710) to provide healthcare to a patient (0703). The HIS (0710) is configured with a remote patient monitoring (RPM) and risk stratification process (0711) that interfaces to data flows within the HIS (0710) and thus enable the care management team (0701, 0702) to view on dashboards a real-time status of the medical state of the patient (0703).

The care management team (0701, 0702) may generate an admit/discharge/transfer (ADT) order (0712) within the HIS and this triggers a transfer of patient information over a communication network (0720) to a healthcare web server (0730) responsible for integrating in-patient and out-patient healthcare delivery to the patient (0703). The HWS (0730) stores information related to the ADT (0712) in a patient demographic database (0731) that is then used by an alert process (0732) to generate information on a website portal (0733) regarding potentially important patient medical information, such as that which may be collected from a medical instrument device (MID) (0734).

This website portal (0733) is then accessed by an out-patient healthcare mobile caregiver (0735) to manage the care of the patient (0703) outside the context of the hospital. Note that in this context the care management team (0701, 0702) which typically operates within the context of a hospital or other healthcare facility may have identical patient views as the caregiver (0735). This permits both in-patient care and out-patient care to be coordinated among the various caregivers. Real-time patient status displays (0736) may be provided by both the HIS RPM process (0711) and accessible via the HWS (0730) website portal (0733) to enable all parties (0701, 0702, 0735) associated with the patient (0703) to be kept fully informed as to the current healthcare status of the patient (0703).

Remote Patient Monitoring Delivery Enrollment Method (0800)

Figure 8:
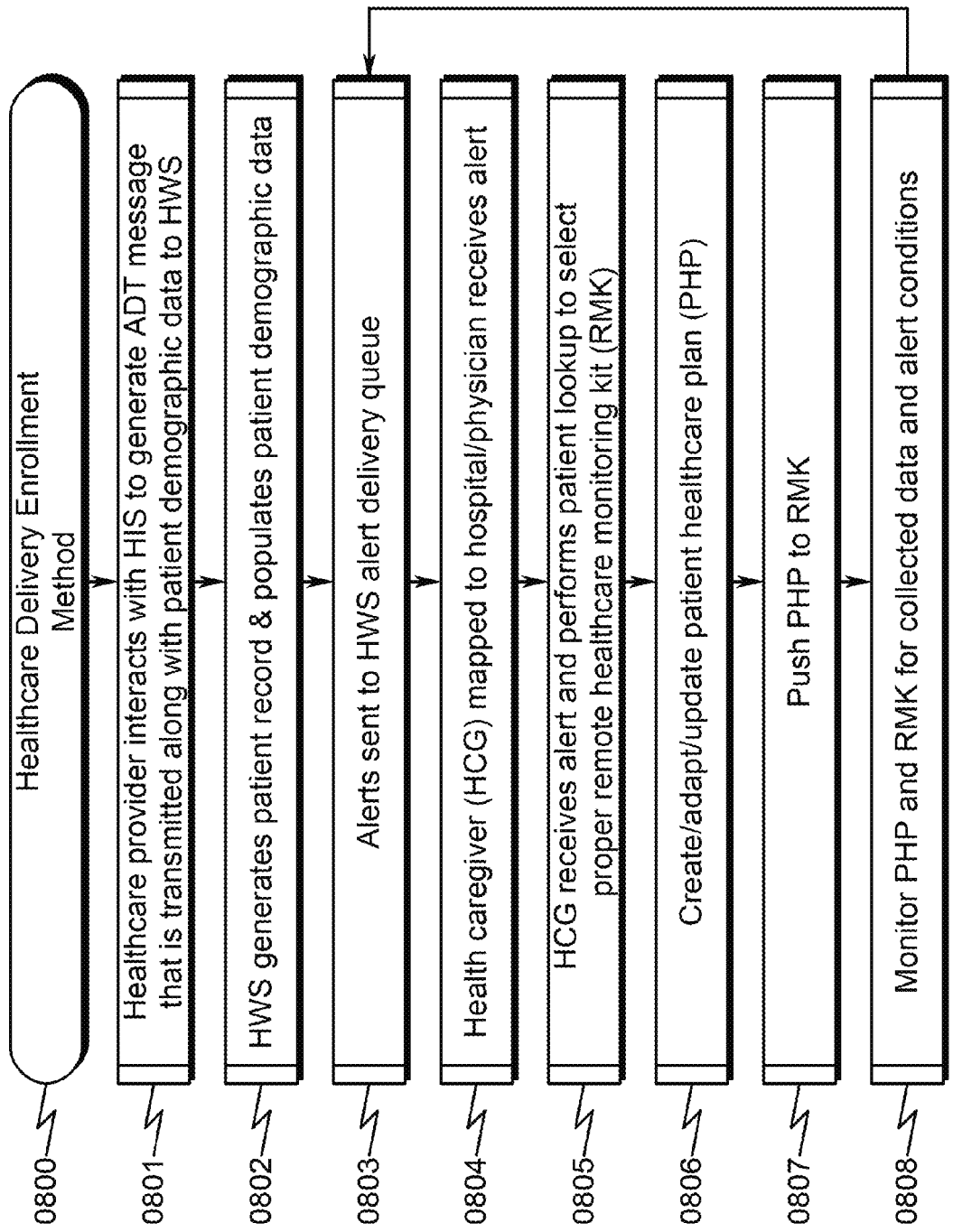
FIG. 8 illustrates a preferred exemplary flowchart of a preferred exemplary healthcare delivery method associated with a patient receiving in-patient and out-patient care.

Associated with the exemplary Healthcare Delivery Information Flow described in FIG. 7 (0700) is a Remote Patient Monitoring Delivery Enrollment Method as depicted in FIG. 8 (0800) that comprises the following steps:

(1) The healthcare provider interacts with the HIS to generate an ADT message that is transmitted along with patient demographic data to the HWS (0801);
(2) The HWS generates a patient record from information received from the HIS and populates this record with patient demographic data (0802);
(3) Alerts are sent to the HWS alert delivery queue (including request for remote patient monitoring (RPM)) (0803);
(4) Health caregiver (HCG) mapped to the hospital/physician receives the alert (0804);
(5) HCG receives the alert and performs patient lookup to select the proper remote healthcare monitoring kit (RMK) (comprising a mobile user device (MUD) and medical instrumentation devices (MID)) (0805);
(6) The HCG creates/adapts/updates a patient healthcare plan (PHP) on the HWS (0806);
(7) The HWS pushes the PHP to the RMK for execution (0807); and
(8) The HWS monitors the PHP and RMK for collected data and alert conditions and queues these alerts for delivery to the HCG and continues processing at step (3) (0808).

One skilled in the art will recognize that these method steps may be augmented or rearranged without limiting the teachings of the present invention. This general method summary describes how the remote patient monitoring (RPM) instrumentation is integrated within the HWS coordinated healthcare plan as defined by the PHP. Note that as the PHP is updated, it is automatically pushed to the RMK (comprising the MUD and MID) and as such the PHP dictates autonomous remote delivery of healthcare to the patient in this context. As alerts are received by the HCG from the HWS, the HCG may respond to the patient alerts in real-time and optionally update the PHP to address changing medical requirements for the patient.

Patient Risk Stratification (0900)

One feature of the present invention that is specifically directed towards improvement of healthcare associated with hospitals and other medical institutions is the ability to perform patient risk stratification automatically to enable the hospital/medical institution to reduce the number of re-admits after a patient discharge. This is accomplished by coupling post-discharge patient educational materials with event/time triggers that force proactive hospital/healthcare provider activity when measured patient healthcare data exceeds predefined limits associated with their specific patient healthcare plan (PHP).

Figure 9:
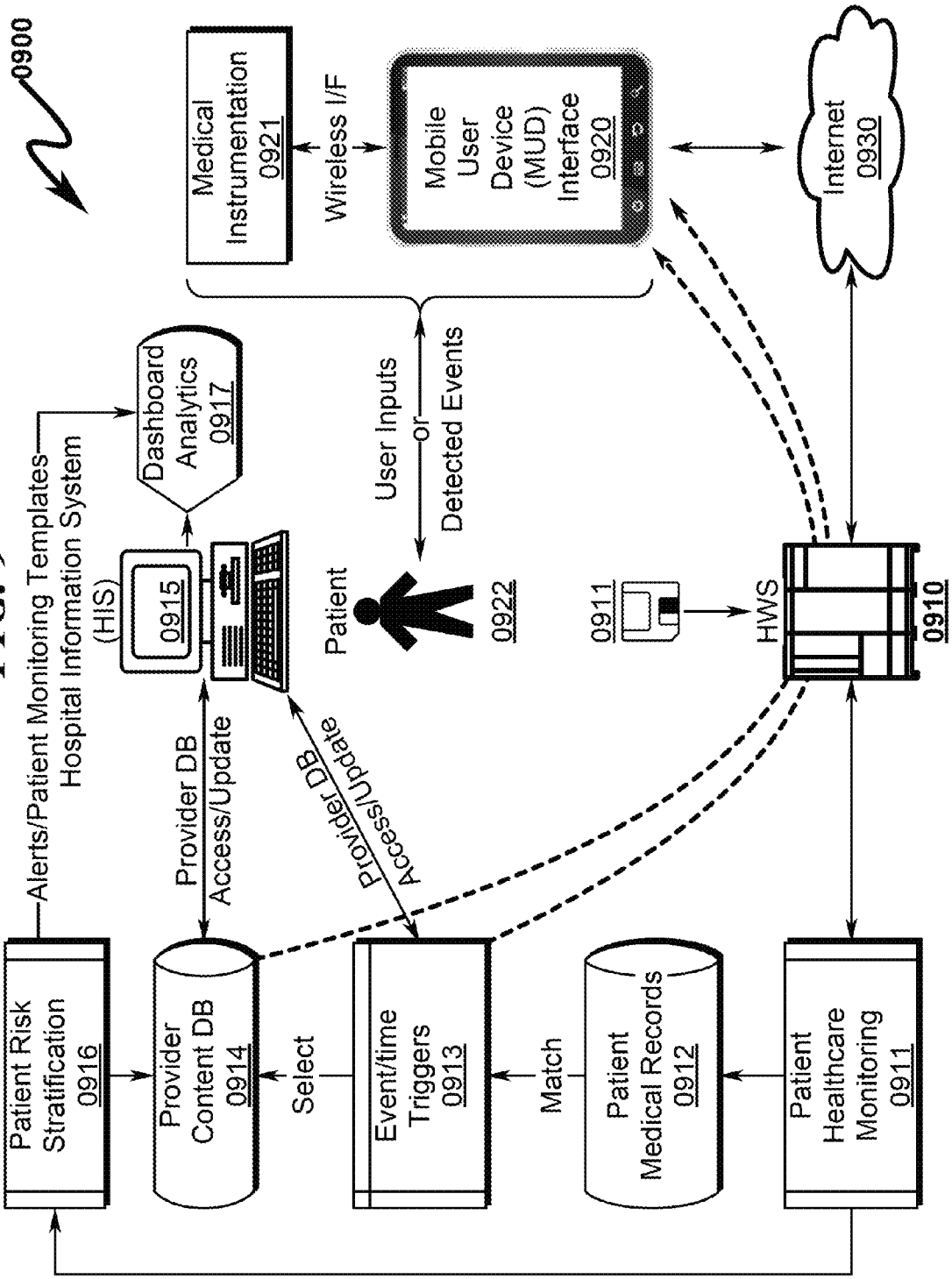
FIG. 9 illustrates an exemplary data flow diagram depicting health caregiver alert delivery integration of patient alerts and real-time patient risk stratification.

This is accomplished according to the system data flow depicted in FIG. 9 (0900). Here the healthcare web server (HWS) (0910) interacts with the mobile user device (0920) to collect medical data (0921) from a patient (0922). This may include information such as patient weight, blood pressure, pulse oximeter data, glucometer data, etc. This data is continuously collected and monitored by the HWS (0910) in a patient healthcare monitoring process (0911) that updates patient medical records (0912) that are distributed to various healthcare providers/hospitals as directed by the patient healthcare plan (PHP). These patient medical records (0912) are then matched to event/time triggers (0913) that indicate various thresholds or alerts associated with collected patient medical data that should trigger a healthcare provider activity. Triggering (0913) of an alert or event based on collected medical data (0912) may force healthcare provider content (0914) to be pushed to the patient (0922) for viewing/educational purposes to modify patient behavior based on collected medical information. For example, readings from a glucose meter may trigger the system to prompt the patient to have a small meal to balance their blood sugar levels.

Associated with these event/time triggers (0913) is a mechanism to stratify the patient risk for readmission into the hospital and report this potential condition to the HIS computer (0915) via an ancillary monitoring risk stratification process (0916) running on the HWS (0910). Dashboard analytics process status monitors (0916) may be continuously updated by this risk stratification process (0916) to provide the HIS (0915) and the associated hospital personnel a real-time status of potentially at-risk patients and permit intervention by hospital personnel to correct any potential patient conditions that might result in a re-admit to the hospital. In many circumstances a detected patient medical event may automatically trigger predefined healthcare provider media content (0914) to be streamed to the MUD (0920) for interaction with the patient (0922) in an attempt to correct the out-of-bounds medical condition detected by the event/time triggers (0913).

Health Caregiver Alert Delivery Method (1000)

Figure 10:
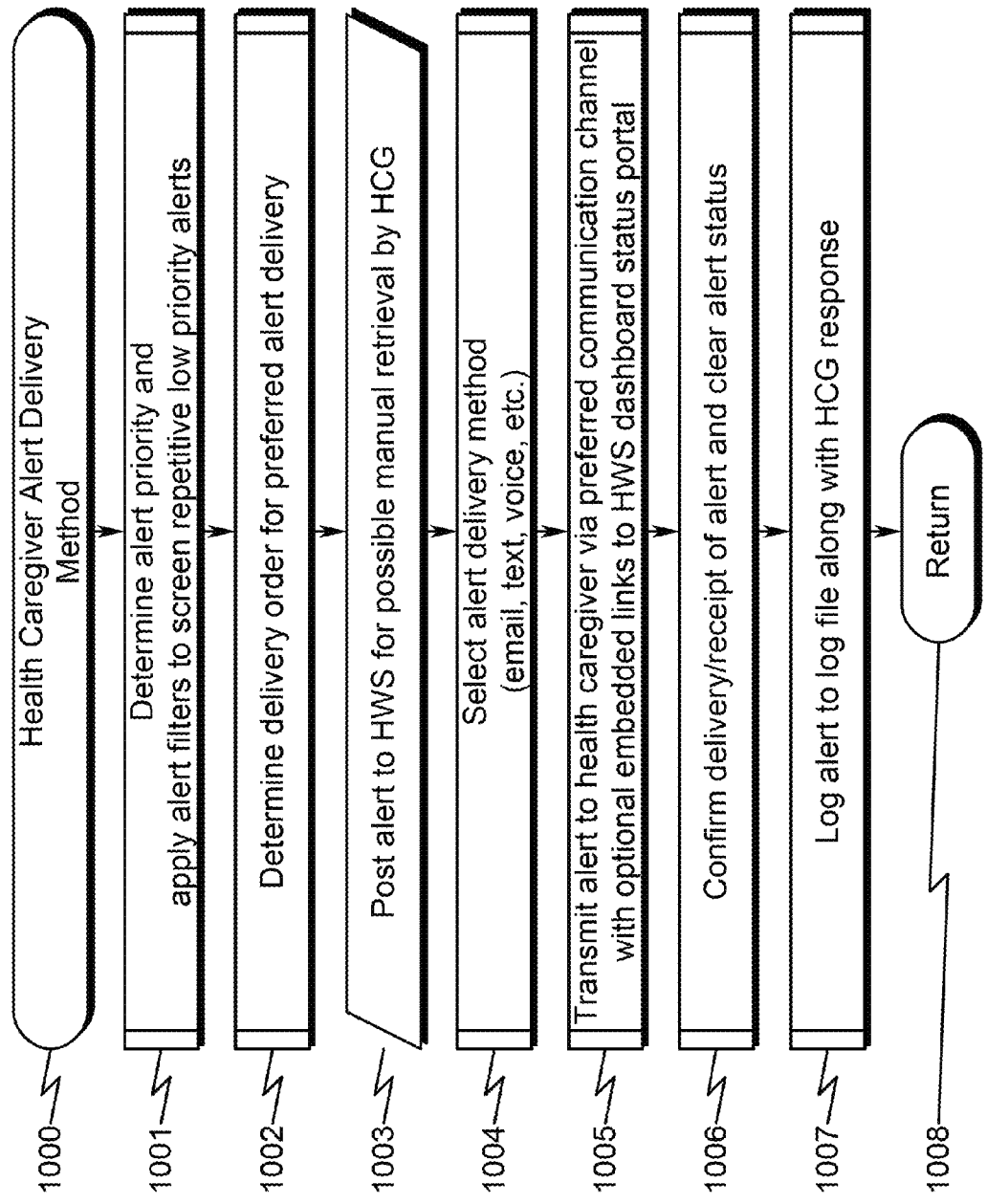
FIG. 10 illustrates an exemplary flowchart depicting a health caregiver alert delivery method.
Figure 11:
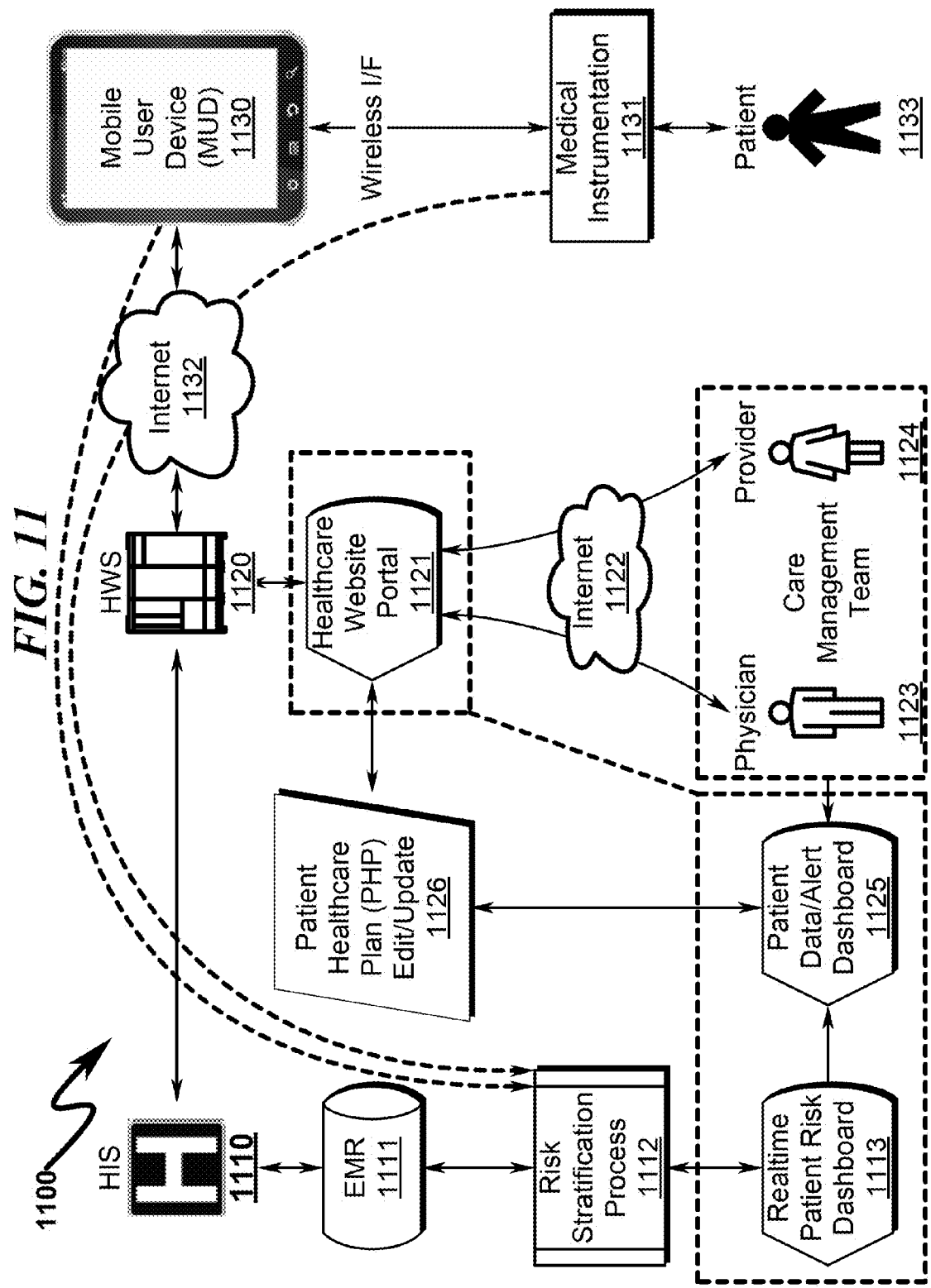
FIG. 11 illustrates an exemplary data flow diagram depicting real-time risk stratification dashboards integrated with dynamic patient healthcare plan (PHP) modification by healthcare providers.

Associated with the exemplary risk stratification system overview described in FIG. 9 (0900) is a health caregiver alert delivery method as depicted in FIG. 10 (1000) that comprises the following steps:
(1) Determining an alert priority and applying alert filters to screen repetitive low priority alerts (1001);
(2) Determining the delivery order for preferred alert delivery (1002);
(3) Posting patient alerts to the HWS for possible manual retrieval by a health caregiver (HCG) (1003);
(4) Selecting the alert delivery method (email, text, voice, etc.) (1004);
(5) Transmitting the alert to a health caregiver via the preferred communication channel with optional embedded hyperlinks to HWS dashboard status portal displays (1005);
(6) Confirming delivery/receipt of the patient alert and clearing the alert status (1006); and
(7) Logging the patient alert to a log file with the HCG response (1007).

One skilled in the art will recognize that these method steps may be augmented or rearranged without limiting the teachings of the present invention. This general method summary may also be augmented with HCG dialogs that allow the patient healthcare plan (PHP) to be updated in response to patient alerts reported by the HWS to the HCG.

Real-Time Analytics Method (1200)

Figure 12:
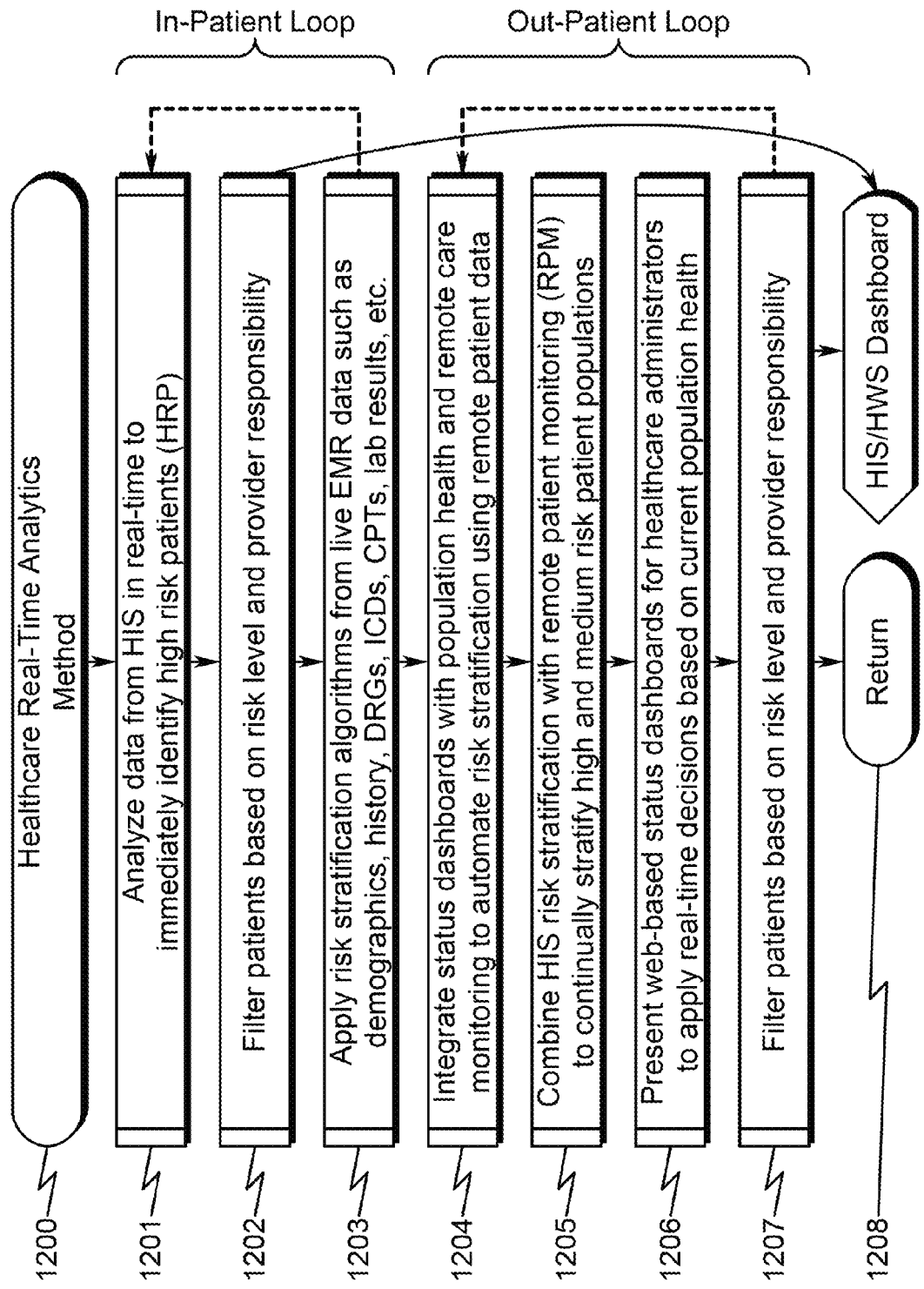
FIG. 12 illustrates an exemplary overview flowchart depicting a healthcare real-time analytics method that permits healthcare providers the ability to risk stratify patients based on real-time data collected from in-patient and out-patient monitoring.

The present invention anticipates incorporation of a real-time analytics method as generally depicted in FIG. 12 (1200) that is designed to permit healthcare providers spanning a number of healthcare facilities the ability to have real-time access to the healthcare status of a patient based on an integration of HIS data as well as information collected from other healthcare providers and remote patient monitoring (RPM) devices. This general healthcare real-time analytics method generally comprises the following steps:
(1) Via execution of a data monitoring process within the HIS infrastructure, analyzing data from the HIS in real-time to immediately identify high risk patients (HRP). This step involves incorporating a data monitoring process within the HIS system to tap data as it flows among the various HIS system components (lab results, chart information, billing codes, etc.) and correlate this information on a per-patient basis to obtain an integrated view of each individual patient so as to be able to compare individual patients against the entire patient population (1201).
(2) Filtering patients based on healthcare provider responsibility or other views. This permits a given group of patients to be associated with an individual healthcare provider (doctor, nurse, etc.) or facility, and limits the scope of access to patient information based on the responsible healthcare provider (1202).
(3) Applying risk stratification algorithms from live electronic medical record (EMR) patient data such as might be obtained from demographics, history, DRGs, ICDs, CPTs, lab results, etc. These algorithms may take a variety of forms, but one preferred method is to stratify a given patient datum in terms of low/medium/high risk (for example low=0, medium=1, high=4) and then sum the risks across all datums for a patient to obtain a real-time index as to the overall patient risk Steps (1)-(3) may be repeated while the patient is treated on an in-patient basis (1203).

(4) Integrating HIS status dashboards with population health and remote care monitoring to automate risk stratification using remote patient data. This step occurs after patient discharge and integrates the risk stratification information from the HIS real-time process with real-time remote patient monitoring (RPM) data obtained after the patient is discharged to re-stratify the risk of the patient once the hospital setting has been exited (1204).

(5) Combining HIS risk stratification information with remote patient monitoring (RPM) to continually stratify high and medium risk patient populations (1205).

(6) Present web-based status dashboards for healthcare administrators to apply real-time decisions based on current patient population health (1206).

(7) Filtering patient based on risk level and provider responsibility to focus the attention of healthcare providers on patients that present the highest risk profile via the use of real-time status dashboards. Steps (4)-(7) may be repeated while the patient is treated on an out-patient basis (1207).

As can be seen from this generalized method flowchart, the present invention differs from that of the prior art in two significant aspects. First, data within the HIS environment is collected in real-time to risk stratify the patients while they are treated on an in-patient basis as compared to making this determination after the patient has been billed or discharged from the facility. This real-time risk stratification occurs within the healthcare facility to ensure that at-risk patients are immediately treated to improve the chances of their overall recovery. Second, data is collected from remote patient monitoring (RPM) devices in conjunction with patient questionnaires after the patient is discharged on an out-patient basis and dynamically integrated with HIS risk stratification data to present patient status dashboards to healthcare professionals that enable them to modify patient treatment after discharge in an attempt to reduce the probability of patient readmission to the healthcare facility. The combination of these two processes is designed to reduce the overall cost of healthcare delivery to at-risk patients and simultaneously provide optimal healthcare to individuals who would most benefit from immediate intervention of a healthcare provider. Since readmission to the hospital or healthcare facility results in increased healthcare costs for the facility, any reduction in readmissions will significantly reduce overall healthcare delivery costs for the institution.

Real-Time Analytics Detail Method (1300)-(1400)

Figure 13:
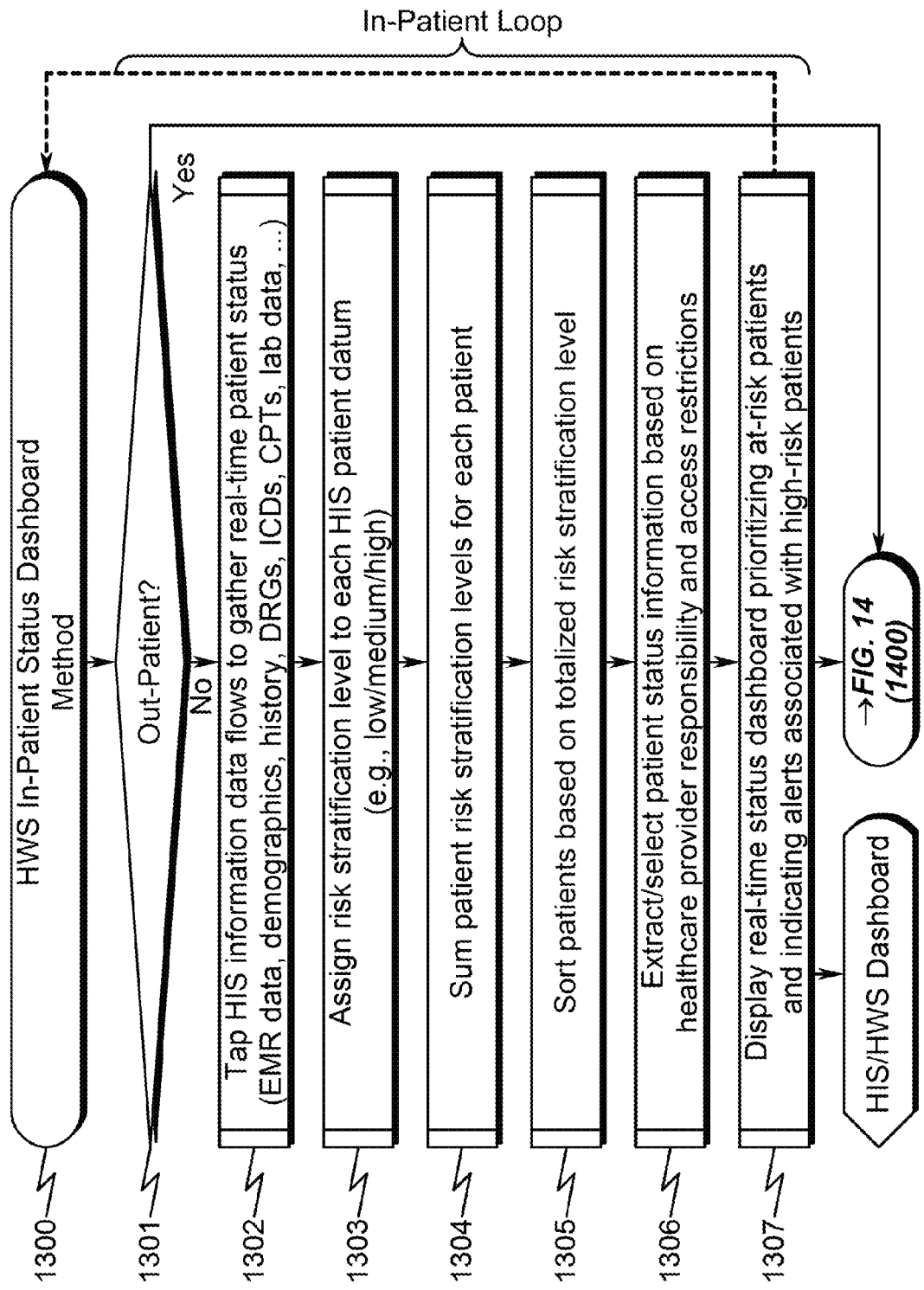
FIG. 13 illustrates an exemplary detail flowchart depicting a HWS/HIS patient status in-patient dashboard method useful in many preferred invention embodiments.
Figure 14:
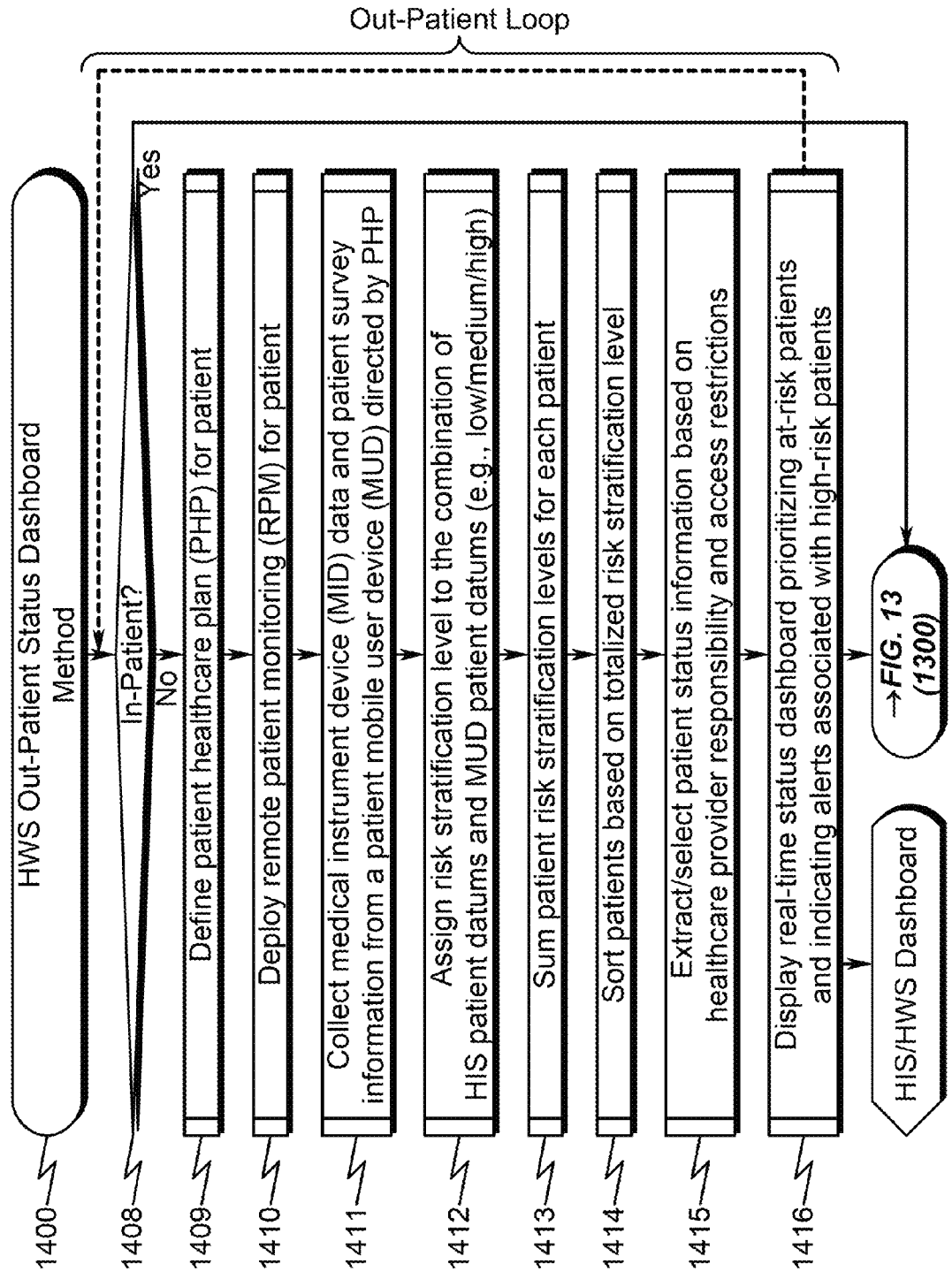
FIG. 14 illustrates an exemplary detail flowchart depicting a HWS/HIS patient status out-patient dashboard method useful in many preferred invention embodiments.
Figure 15:
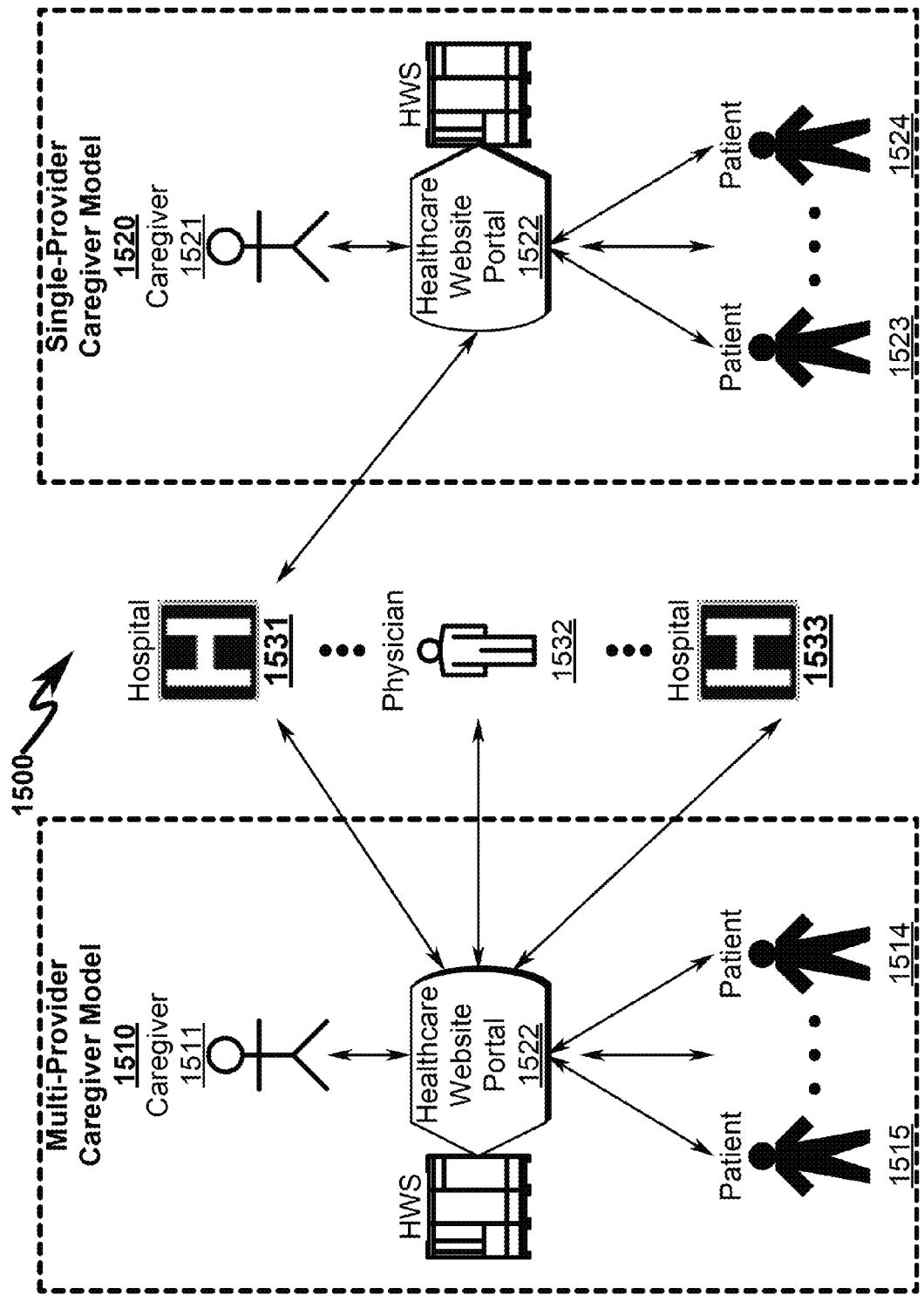
FIG. 15 illustrates an exemplary invention embodiment system configuration depicting multi-provider caregiver models and single-provider caregiver models.
Figure 16:
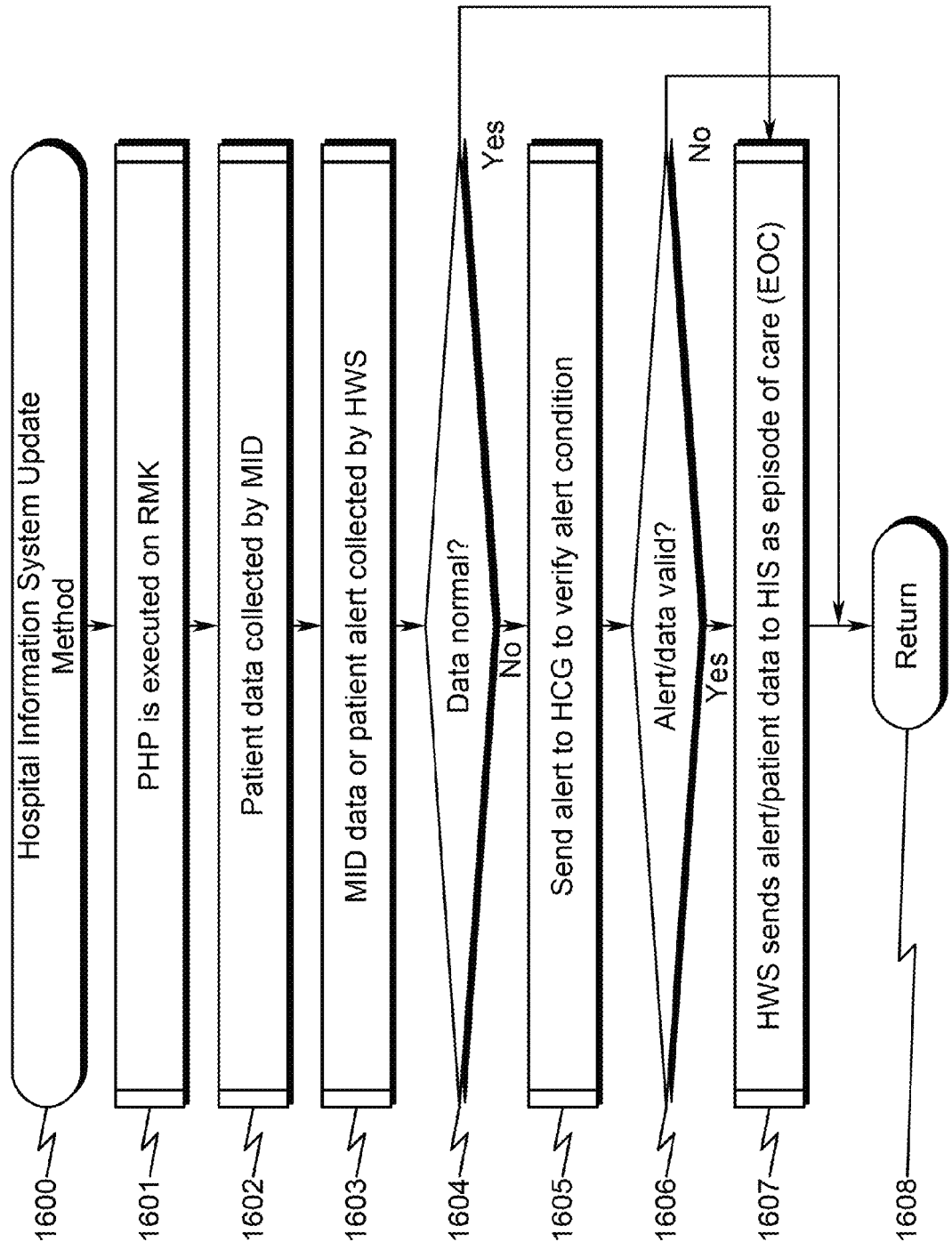
FIG. 16 illustrates an exemplary invention embodiment method flowchart depicting filtered HIS data flows.

A more detailed explanation of the Real-Time Analytics Method depicted in FIG. 12 (1200) is illustrated in the flowcharts of FIG. 13 (1300) and FIG. 14 (1400). These flowcharts generally depict the in-patient (1300) and out-patient (1400) methods by which real-time status dashboards may be presented to healthcare professionals in an attempt to identify at-risk patients for additional treatment by the healthcare professionals. This general healthcare real-time analytics and display method generally comprises the following steps:

(1) Determining if the patient is to be treated on an out-patient basis, and if so, proceeding to step (8) (1301);

(2) Tapping HIS information data flows to gather real-time patient status information such as EMR data, demographics, history, DRGs, ICDs, CPTs, lab results data, clinical notes, etc. (1302);

(3) Assigning risk stratification levels to each HIS patient datum collected (such as low/medium/high) (1303);

(4) Summing the patient risk stratification levels for all datums associated with a given patient (1304);

(5) Sorting patients based on totalized risk stratification level (1305);

(6) Extracting and/or selecting patient status information based on healthcare provider responsibility and patient data access restrictions (1306);

(7) Displaying a real-time status dashboard prioritizing at-risk patients and indicating alerts associated with high-risk patients (this may involve a variety of notification communications to various healthcare professionals via a web interface or other electronic media) and continuing to step (1) while the patient is treated on an in-patient basis (1307);

(8) Determining if the patient is to be treated on an out-patient basis, and if so, proceeding to step (1) (1408);

(9) Defining a patient healthcare plan (PHP) for the patient (1409);

(10) Deploying remote patient monitoring (RPM) to monitor patient healthcare and provide a means for collecting patient questionnaire information (1410);

(11) Collecting medical instrument device (MID) data and patient survey information from a patient mobile user device (MUD) under direction of the PHP (1411);

(12) Assigning risk stratification levels to the combination of HIS patient datums and MUD patient datums (such as low/medium/high) (1412);

(13) Summing patient risk stratification levels for each individual patient (1413);

(14) Sorting patients based on totalized risk stratification levels (1414);

(15) Extracting/selecting patient status information based on healthcare provider responsibility and patient data access restrictions (1415);

(16) Displaying a real-time status dashboard prioritizing at-risk patients and indicating alerts associated with high-risk patients (this may occur in the context of a HIS dashboard display, a web page presented using a conventional web browser, and/or other electronic communication methodologies) (1416).

As depicted in this flowchart, the method integrates the risk stratification information from the HIS computers as well as information collected from remote patient monitoring (RPM) and patient surveys presented to the patient via the MUD. It should be noted in these detail flowcharts that a simplified risk stratification algorithm has been depicted that only uses a three-level risk assessment (low/medium/high) in conjunction with a simple summing algorithm to generate an overall risk assessment for the patient. This risk stratification algorithm can have many forms, including those with more than three gradations of risk assessment, conditional risk assessment metrics (e.g., high blood pressure AND previous stroke=high risk), and/or non-linear risk assessment algorithms (e.g., add to risk=weight*previous stroke (to increase risk assessment for overweight patients previously experiencing a stroke)). All of these risk stratification methodologies may be incorporated within the PHP which drives patient care on an out-patient basis.

PHP/MUD Synchronization (1700)

Figure 17:
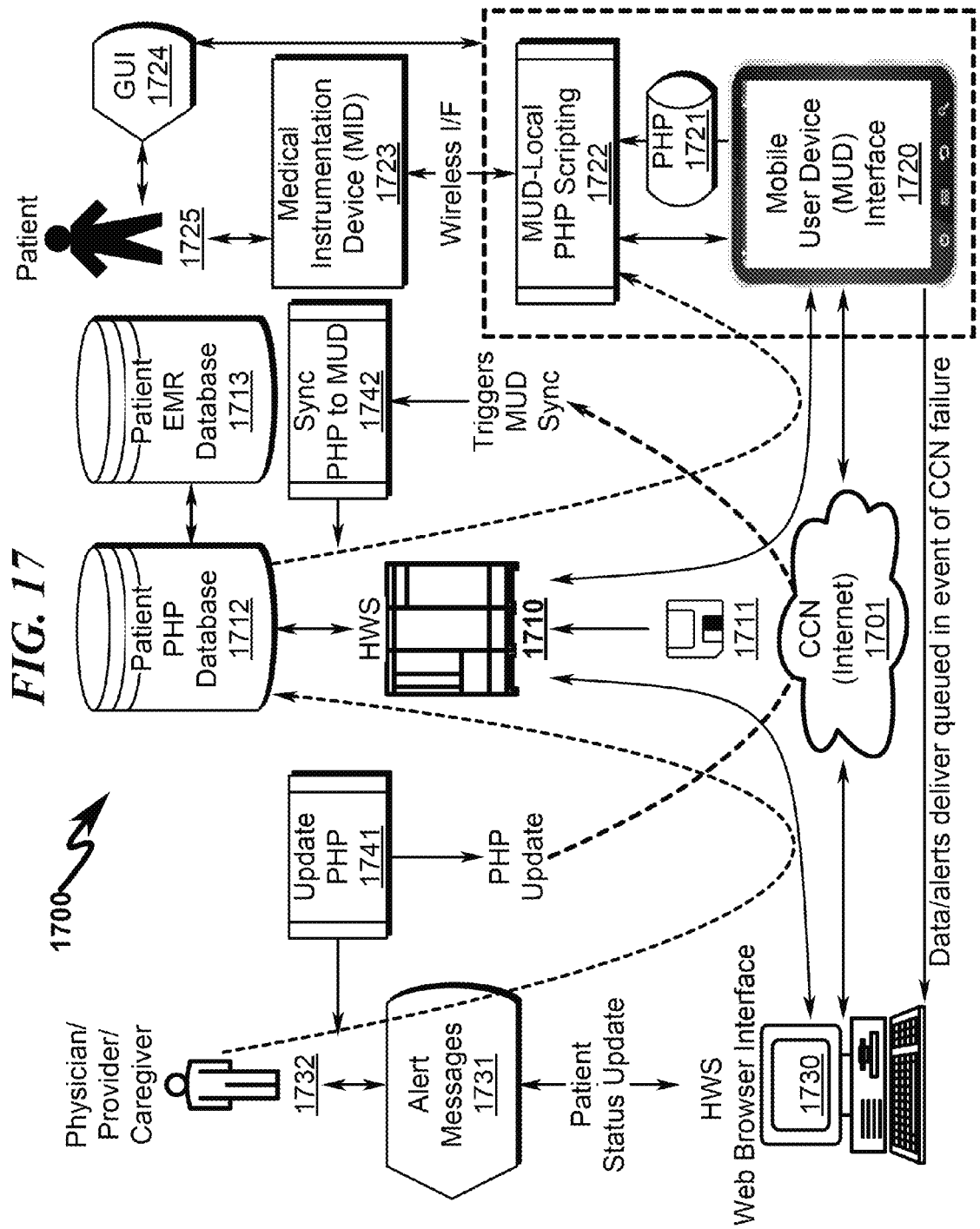
FIG. 17 illustrates an exemplary system diagram illustrating data flows associated with synchronization of the healthcare web server (HWS) patient healthcare plan (PHP) database between healthcare providers and the patient mobile user device (MUD)

The present invention utilizes a patient healthcare plan (PHP) to coordinate the delivery of patient healthcare. As depicted in FIG. 17 (1700), the healthcare web server (1710) operating under control of machine instructions read from a computer readable medium (1711) maintains a patient PHP database in which healthcare plans for a variety of patients are maintained. The PHP for an individual patient is extracted from this database and communicated via computer communications network (CCN) (1701) to a mobile user device (MUD) (1720) for local storage (1721) and execution by a MUD-local PHP scripting engine (1722). The PHP scripting engine (1722) is responsible for interpreting the information in the patient-specific PHP and executing it within the context of the MUD (1720) environment even if communication with the HWS (1710) via the CCN (1701) is disrupted. The PHP scripting engine (1722) interacts with medical instrumentation devices (MID) (1723) and user query/responses (1724) that are associated with the patient (1725). Thus, the MUD-local PHP (1721) may operate independently of external systems and permit collection of patient data in situations where direct communication with healthcare providers is not possible.

Within this context the HWS (1710) may permit authorized access to individual patent healthcare plans within the PHP database (1712) via the CCN (1701) using a web browser interface (1730). This web browser interface (1730) as described herein may permit patient alert messages to be displayed (1731) to physician/provider/caregiver (1732) having authorized access to the specific patient medical records. These alert messages (1731) may necessitate an update of the PHP for the patient (using an update PHP process (1741) operating within the context of the HWS (1710)), in which case the web browser interface (1730) is used to communicate with the HWS (1710) to update the PHP database (1712) which is automatically queued for synchronized transmission (using PHP synchronization process (1742) operating within the context of the HWS (1710)) to the MUD (1720) for local storage (1721) and execution (1722) within the context of the remote patient monitoring (RPM) system.

This synchronized distribution of the PHP provides several benefits, including but not limited to the following:

- The HWS (1710) permits a plethora of HWS web browser interfaces (1730) to have access to the PHP database (1712) and thus monitor the patient status in real-time and dynamically control the delivery of healthcare to the patient by making changes in the PHP for individual patients.
- The MUD (1720) need not be actively tethered to the HWS (1710) for the system to deliver a healthcare plan to the patient (1725), as the local storage (1721) of the PHP ensures that the system can operate in situations where the CCN (1701) is compromised.
- In the context of healthcare delivered to the patient (1725) via a wide variety of sources (1732) such as hospitals, clinics, outside physicians, specialists, physician assistants, nurses, caregivers, aids, etc. the system as depicted permits each caregiver a more global view of the patient status in that the patient electronic medical record (EMR) (1713) is available in conjunction with patient alerts (1731) that permits a more coordinated and timely response to patient medical needs.
- The system as depicted permits automated interaction with the patient (1725) with respect to presentation of patient queries and collection of patient responses using the MUD (1720) GUI (1724). This activity in conjunction with the collection of MID (1723) data (either automatically or in conjunction with prompted patient (1725) inputs to the GUI (1724)) standardizes and automates much of the healthcare provider interaction with the patient that is prone to acts of error and omission by the healthcare provider.
- The delivered PHP content (1721) executed (1722) within the context of the MUD (1720) may incorporate audio/video training for the patient (1725) in an attempt to automate instruction that would routinely be provided by the physician/provider/caregiver (1732). In situations where the physician/provider/caregiver (1732) is unavailable or occupied, this PHP-driven immediate patient feedback can provide information necessary for the patient to stabilize a potentially serious medical condition prior to the intervention of the physician/provider/caregiver (1732).

Thus, the system as depicted permits a degree of healthcare delivery automation to the patient (1725) while still permitting the PHP to be updated by the physicians/providers/caregivers (1732) associated with the patient (1725). Furthermore, the use of the HWS (1710) web browser interface (1730) permits physicians/providers/caregivers (1732) from widely disparate spatial locales to coordinate patient (1725) treatment with each physician/provider/caregiver (1732) having a full view of the PHP (1712), the patient EMR data (1713), and alert messages (1731) generated by MID data (1723) or patient interaction (1724) with the MUD (1720).

HWS Healthcare Delivery Method (1800)

Figure 18:
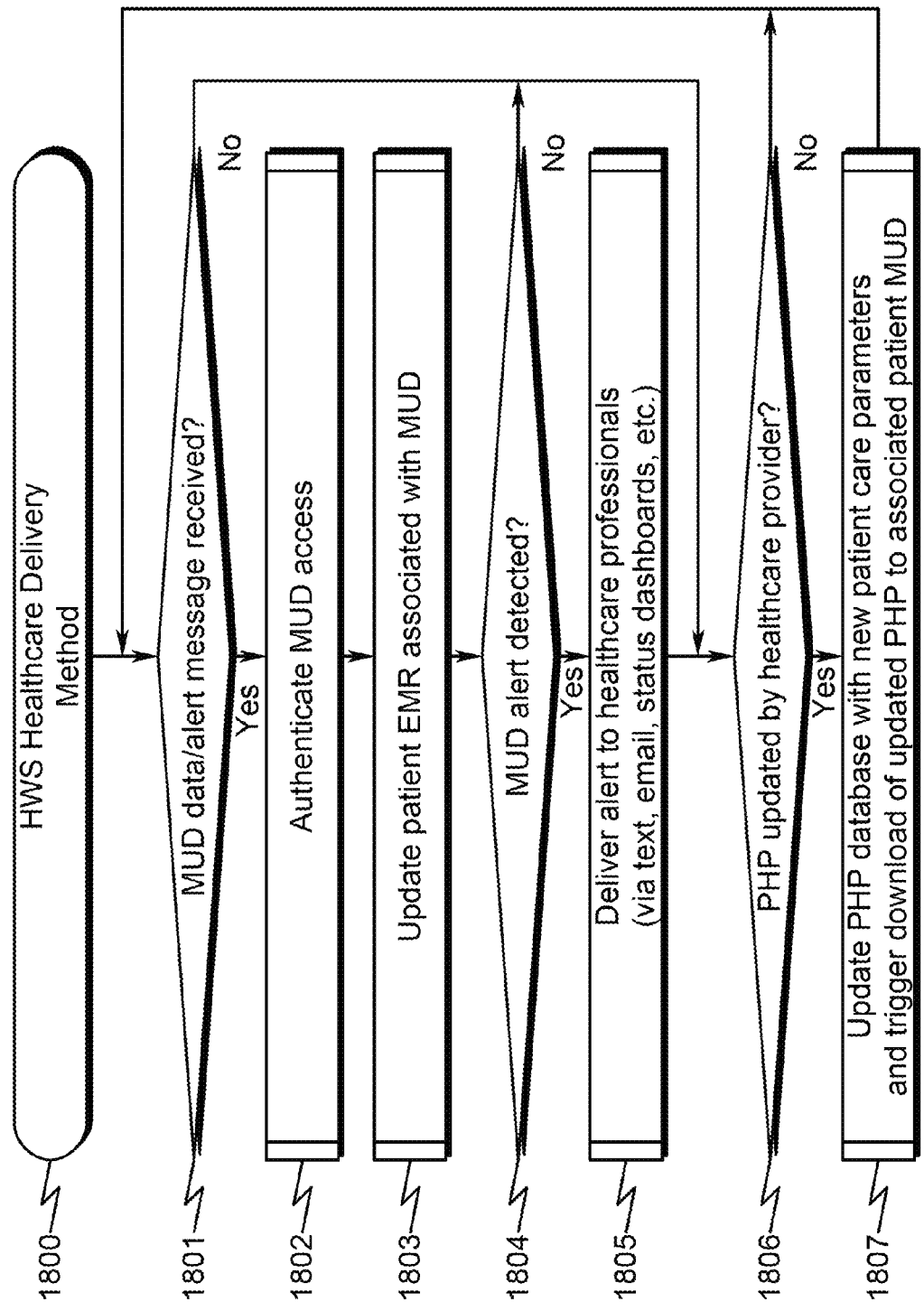
FIG. 18 illustrates a flowchart depicting a preferred exemplary HWS healthcare delivery method.

The PHP/MUD Synchronization data flow depicted in FIG. 17 (1700) may be accompanied by a HWS healthcare delivery method as depicted in FIG. 18 (1800) that defines the interaction between the HWS, the MUD, and the healthcare providers. This method may operate continuously on the HWS or be triggered by interactions between the HWS and the MUD or the HWS and a web browser interface interacting with a healthcare provider. This method generally involves the following steps:

(1) Determining if a data or alert message has been received from a MUD, and if not, proceeding to step (6) (1801);
(2) Authenticating the MUD message to determine its origin and associated patient (1802);
(3) Updating patient EMR data associated with the patient being serviced by the MUD (1803);
(4) Determining if a MUD patient alert has been triggered, and if not, proceeding to step (6) (1804);
(5) Delivering the alert to authorized healthcare professionals via text, email, web browser status dashboards, HIS status screens, or other electronic means (1805);
(6) Determining if the PHP has been updated by a healthcare provider, and if not, proceeding to step (1) (1806); and
(7) Updating the patient PHP database with new patient care parameters and triggering a download of the updated patient PHP data to the associated patient MUD (1807).

Note that this HWS process provides for both reception and delivery of MUD data/alert messages to the healthcare provider as well as mechanisms for the healthcare provider to update the individual patient care plan (PHP) and have this updated PHP immediately transmitted to the associated patient MUD for execution to automatically collect patient medical information and perform a variety of automated patient interactions. This delivery of PHP to the patient MUD also permits the PHP to be executed on the MUD autonomously without further direction by the HWS.

MUD Healthcare Delivery Foreground Method (1900)

Figure 19:
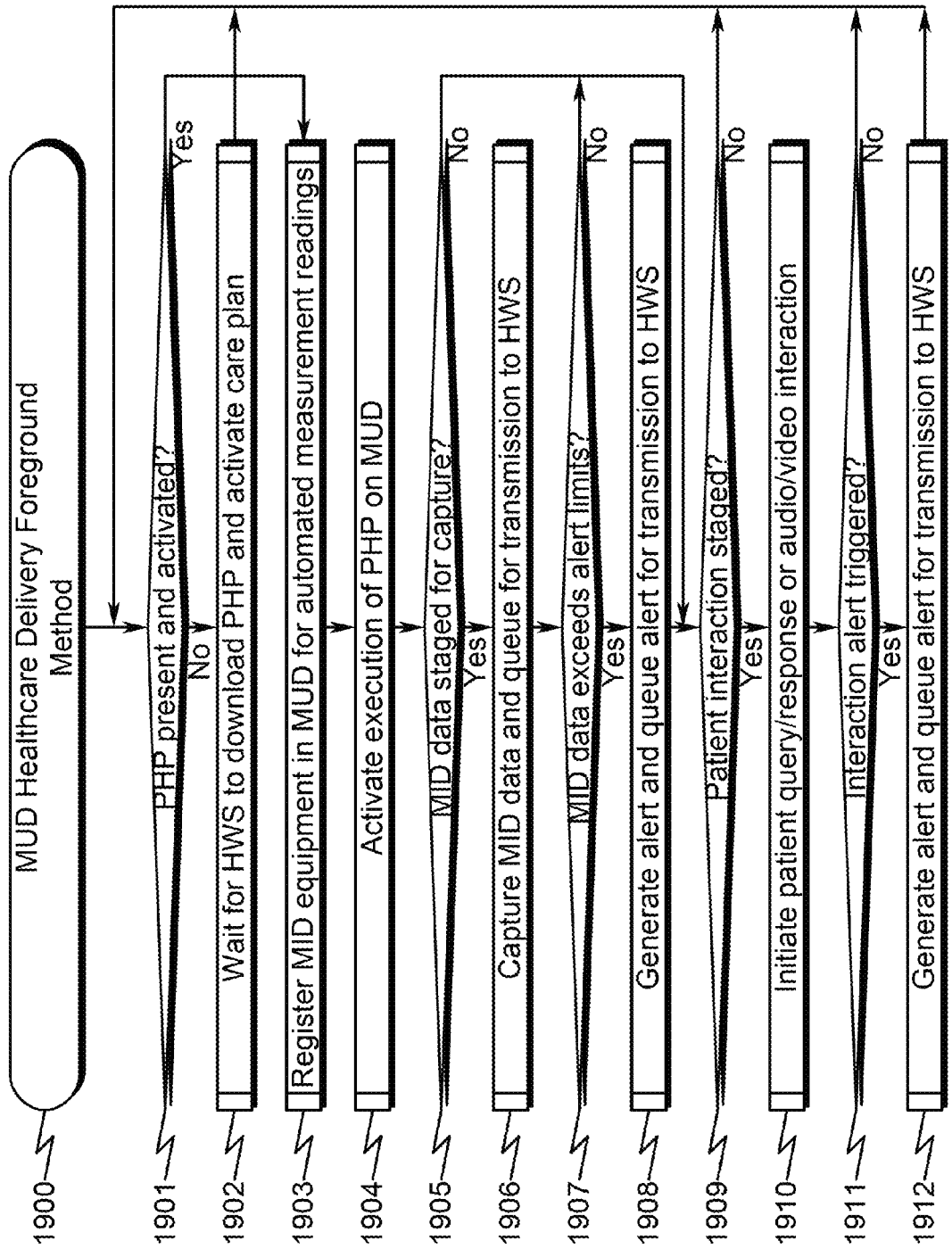
FIG. 19 illustrates a flowchart depicting a preferred exemplary MUD healthcare delivery foreground method.

Associated with the HWS healthcare delivery method depicted in FIG. 18 (1800) is a MUD healthcare delivery foreground method as depicted in FIG. 19 (1900) that services data and alert transfers to the HWS from the medical instrument devices (MID) communicating with the MUD as well as information regarding alerts and other information associated with MUD-patient interactions. This method may operate continuously on the MUD or be triggered by interactions between the HWS and the MUD or the HWS and a web browser interface interacting with a healthcare provider. This method generally involves the following steps:

(1) Determining if a PHP is present on the MUD and currently activated, and if so, proceeding to step (3) (1901);
(2) Waiting for the HWS to download a PHP to the MUD and activate the PHP for MUD execution and then proceeding to step (1) (1902);
(3) Registering MID equipment associated with the patient to permit automated healthcare measurement readings to be obtained for the patient (1903);
(4) Activating execution of the PHP on the MUD (1904);
(5) Determining if MID data is staged for capture by the PHP, and if not, proceeding to step (9) (1905);
(6) Capturing MID data and queuing the MID data for transmission to the HWS (1906);
(7) Determining if MID data exceeds alert limits, and if not, proceeding to step (9) (1907);
(8) Generating an alert and queuing the alert for transmission to the HWS (1908);
(9) Determining if a patient interaction (query/response, audio/video tutorial, etc.) is staged for execution by the PHP, and if not, proceeding to step (1) (1909);
(10) Initiating a patient query/response or audio/video interaction using the MUD as the patient GUI (1910);
(11) Determining if a patient interaction alert has been triggered by the patient interaction, and if not, proceeding to step (1) (1911); and
(12) Generating a patient interaction alert and queuing the alert for transmission to the HWS, then proceeding to step (1) (1912).

Note that this MUD process provides for both capture and delivery of MUD data/alert messages to the HWS as well as mechanisms for the healthcare provider to stage a variety of patient interactions (query/responses, audio/video presentations, etc.) to the patient that may also have data/alerts associated with the patient interaction. As a foreground task running on the MUD, this process permits a wide variety of time/event synchronized activities to be triggered on the MUD that may independently queue patient data and/or alerts to the HWS for real-time inspection by healthcare providers via website browsers accessing the HWS via the CCN. Note that this foreground process may fully interact with the MID equipment and/or patient without having any connectivity to the HWS. Alerts and/or data are queued for transmission to the HWS in this foreground task and processed for transmission to the HWS by the background task depicted in FIG. 20 (2000) and discussed below.

MUD Healthcare Delivery Background Method (2000)

Figure 20:
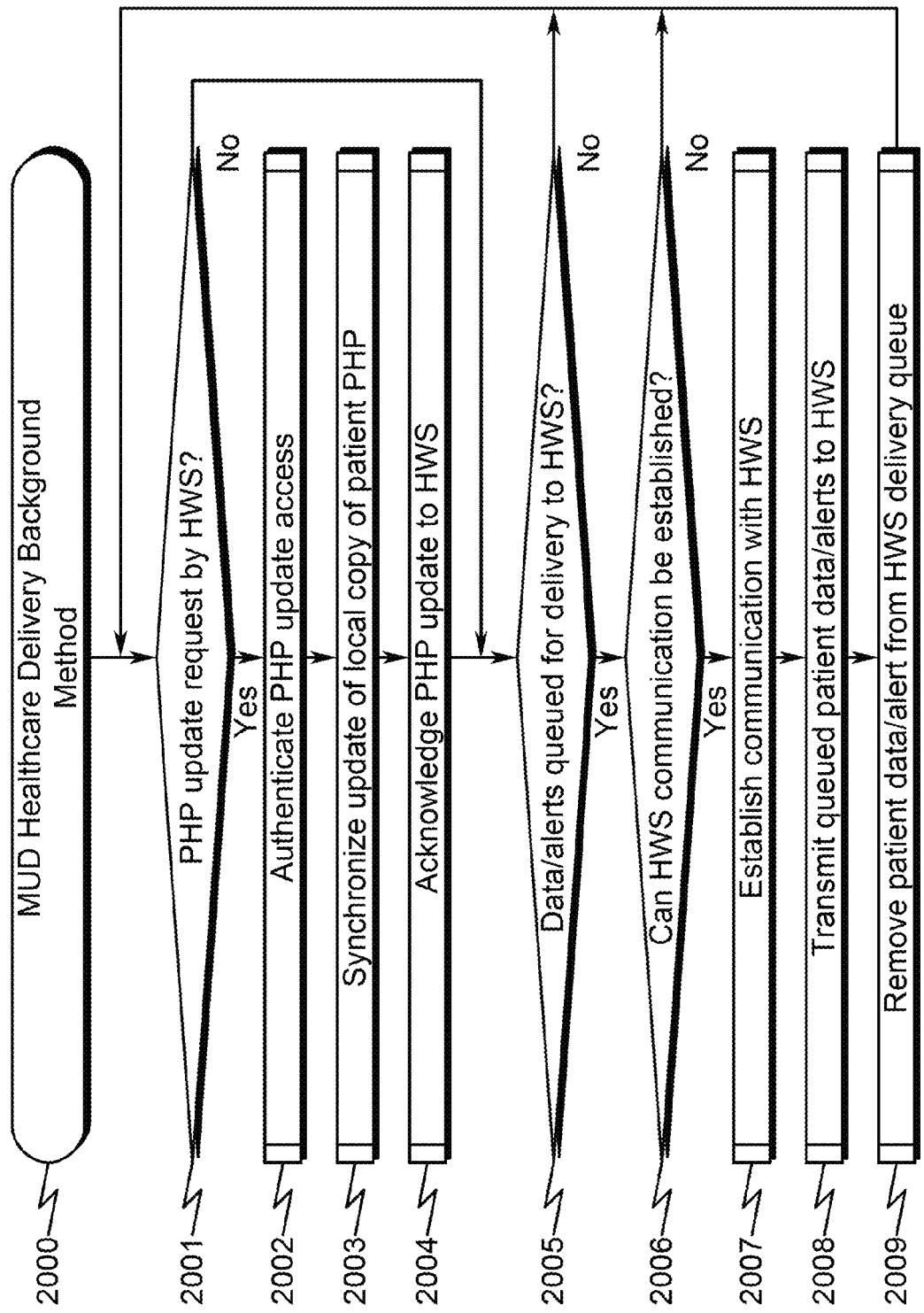
FIG. 20 illustrates a flowchart depicting a preferred exemplary MUD healthcare delivery background method.

Associated with the HWS healthcare delivery method depicted in FIG. 18 (1800) and the foreground process depicted in FIG. 19 (1900) is a MUD healthcare delivery background method as depicted in FIG. 20 (2000) that services PHP update requests from the HWS as well as the queued delivery of data/alert message information from the MUD to the HWS. This method may operate continuously on the MUD or be triggered by interactions between the HWS and the MUD or the HWS and a web browser interface interacting with a healthcare provider. This method generally involves the following steps:

(1) Determining if a PHP update request has been received by the MUD from the HWS, and if not, proceeding to step (5) (2001);
(2) Authenticating the PHP update request to ensure that it corresponds to the patient associated with the MUD and that the HWS is in fact authorized to perform the PHP update (2002);
(3) Synchronizing the update of a local copy of the HWS PHP with the master copy of the PHP maintained by the HWS (this may involve terminating execution of a currently running PHP within the MUD foreground or waiting until a point in time where the currently executing PHP may be stopped) (2003);
(4) Acknowledging the PHP update to the HWS (2004);
(5) Determining if data/alerts are queued for delivery to the HWS from the MUD, and if not, proceeding to step (1) (2005);
(6) Determining if communication between the MUD and the HWS can be established, and if not, proceeding to step (1) (2006);
(7) Establishing communication between the MUD and the HWS (2007);
(8) Transmitting queued patient data/alerts from the MUD to the HWS (2008); and
(9) Removing queued patient data/alerts from the MUT-to-HWS transmission queue and proceeding to step (1) (2009).

Note that this MUD process provides for both updating of the PHP by the HWS as well as mechanisms to transmit accumulated patient data/alerts from the MUD to the HWS. As a background task running on the MUD, this process permits autonomous operation of the MUD without direct connectivity to the HWS so that PHP updates may occur and data/alerts may be queued for transmission to the HWS as MUD-HWS connectivity is achieved. This ability to dynamically update the execution of the PHP on the MUD also allows healthcare providers the ability to view incoming patient medical data and alerts and immediately update the PHP to address changing patient healthcare needs.

Exemplar PHP Hierarchy Data Structure (2100)-(2400)

The patient healthcare plan (PHP) as described herein is used to coordinate patient care among a variety of contributing healthcare professionals. This PHP is generated visually by healthcare professionals using a drag-and-drop interface that permits existing customized healthcare plans, healthcare templates, and/or user questionnaires to be integrated into a custom patient healthcare plan that may be manipulated using a traditional GUI web browser interface. The result of this integration is a data structure that is interpreted by the MUD to coordinate patient care remotely. While many forms of this data structure are anticipated with the present invention, an exemplary form of this structure is depicted in FIG. 21 (2100)-FIG. 24 (2400).

Figure 21:
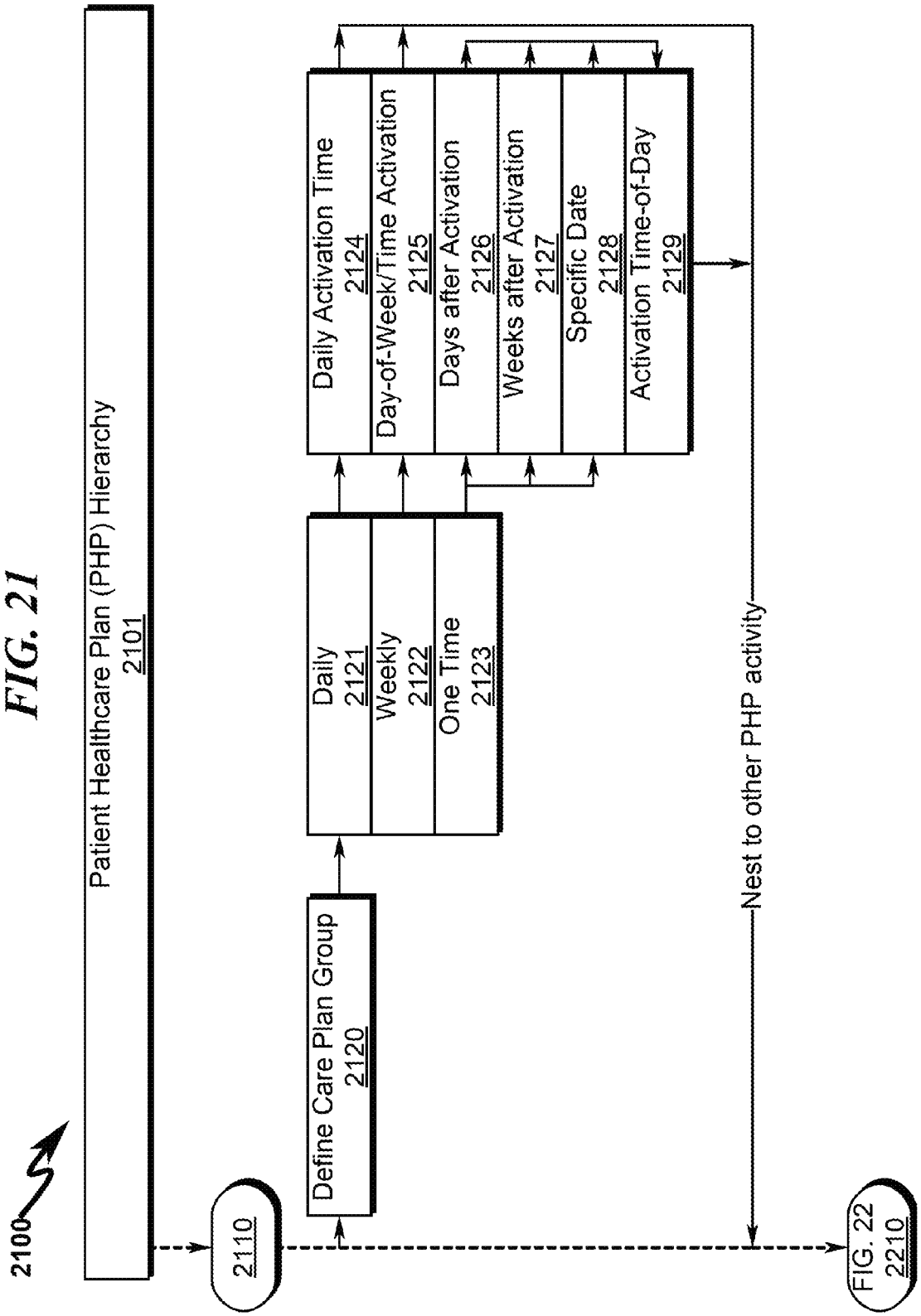
FIG. 21 illustrates details associated with a typical patient healthcare plan (PHP) data structure hierarchy (part 1/4)
Figure 22:
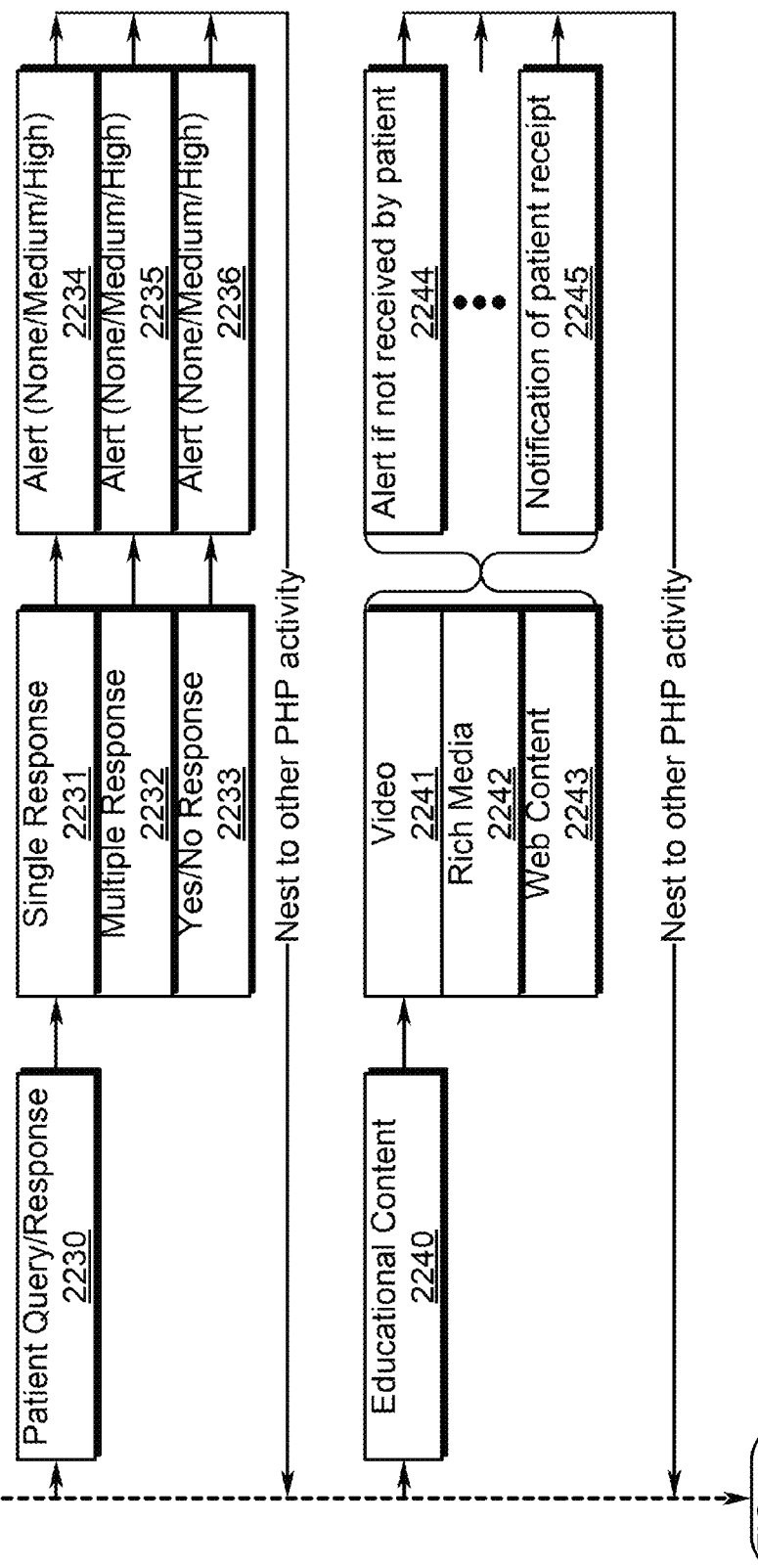
FIG. 22 illustrates details associated with a typical patient healthcare plan (PHP) data structure hierarchy (part 2/4)
Figure 23:
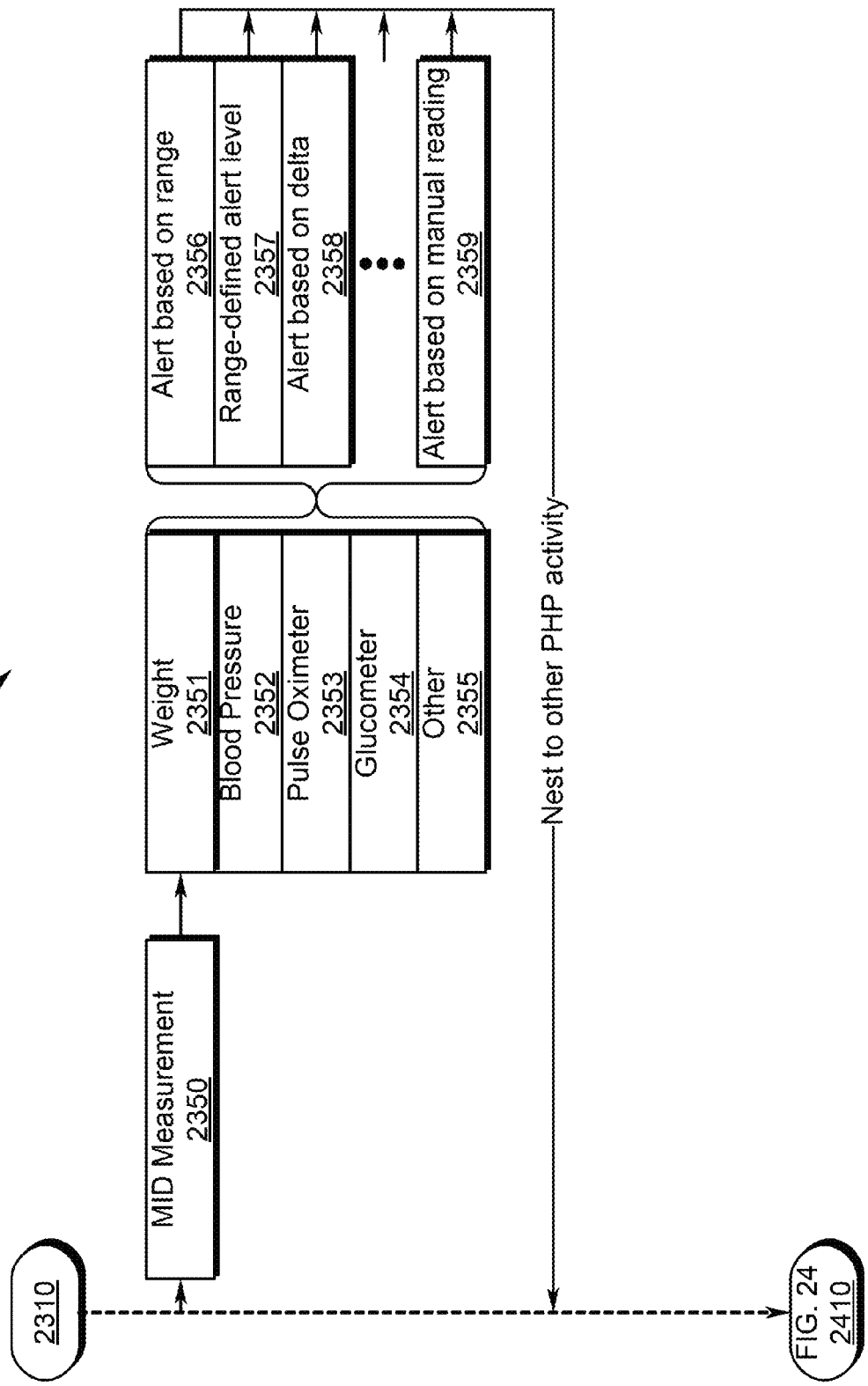
FIG. 23 illustrates details associated with a typical patient healthcare plan (PHP) data structure hierarchy (part 3/4)
Figure 24:
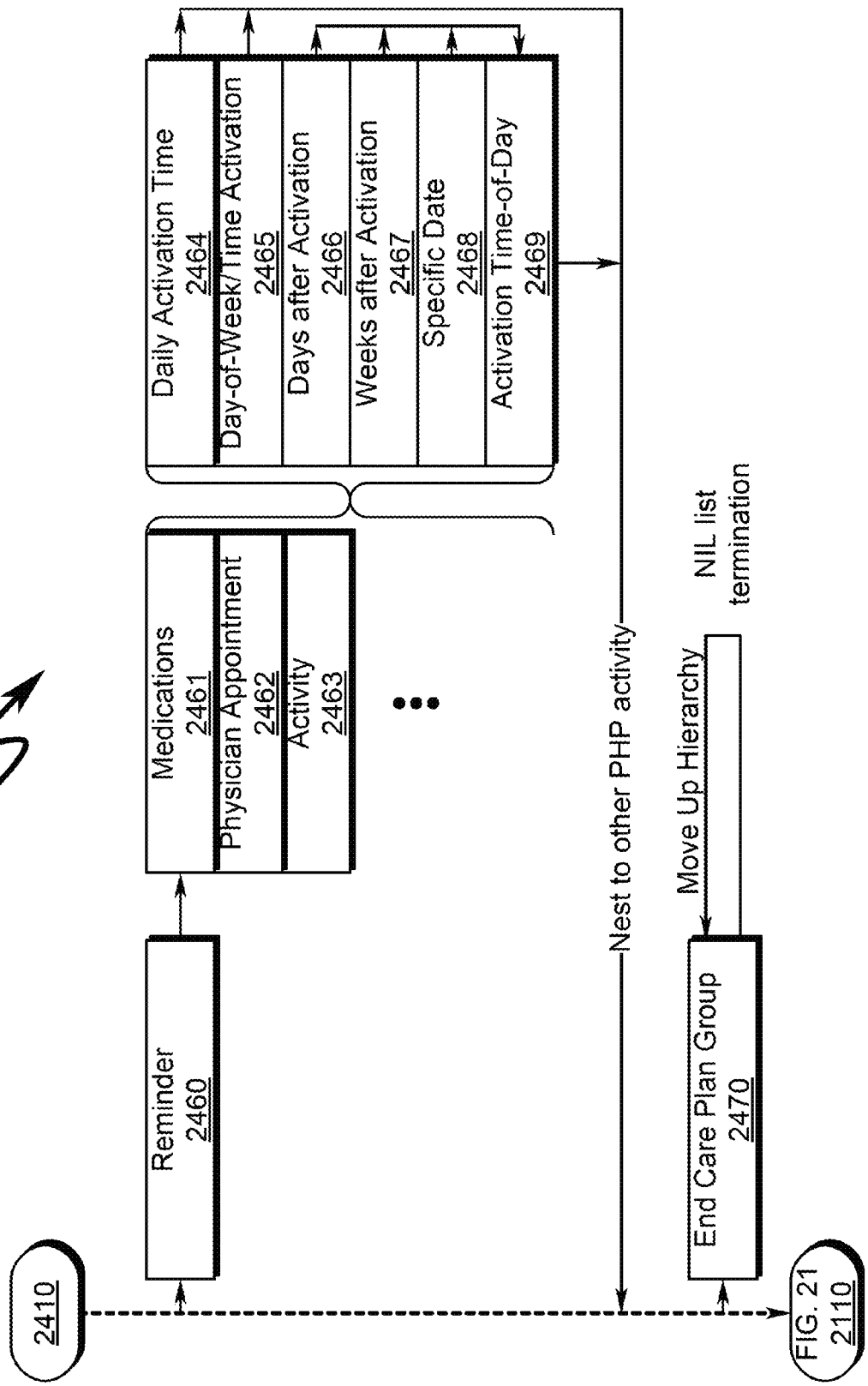
FIG. 24 illustrates details associated with a typical patient healthcare plan (PHP) data structure hierarchy (part 4/4)

The data structure as depicted in FIG. 21 (2100)-FIG. 24 (2400) is hierarchical and begins with an initial tree node (2101) that is combined with a variety of nested primitives that may include (but are not limited to) items such as care plan groups (2120) (defining major branches of activity); patient query/responses (2230); patient interaction with educational content (2240); medical instrumentation device monitoring (2350); and reminder services (2460).

Define Care Plan Group (2120)

This PHP node represents the beginning of a group of related healthcare plans and may represent the container representing the entire healthcare plan. Within this context, daily (2121), weekly (2122), and one-time (2123) activities may be scheduled according to a daily activation time (2124), day-of-week at specific time activation (2125), days after PHP activation time (2126), weeks after PHP activation time (2127), specific activation date (2128), and/or time-of-day activation (2129). Within this context delays may be associated to repeatedly trigger activation of specific PHP actions or groups.

Patient Query/Responses (2230)

The PHP may be configured to allow patient queries and responses (2230) to be gathered and then used to trigger alerts that are routed to the HWS. Within this context it is anticipated that the user may be prompted with text and allowed to provide a single response from a list (2231), multiple responses from a list (2232), or yes/no responses (2233). Each of these response types may be associated with a variety of alert levels (2234, 2235, 2236) that are routed through the HWS to the healthcare providers.

Educational Content (2240)

The PHP may be configured to allow educational content to be presented to the patient (2240) which may include video (2241), rich media content (2242), or other web content (2243). In each of these cases alerts may be generated if the content is not received or interacted with by the patient (2244) and/or notification may be provided on patient receipt (2245) of the educational content.

MID Data Collection (2350)

The PHP anticipates that a variety of medical instrumentation device data may be collected including but not limited to weight (2351), blood pressure (2352), pulse oximeter (2353), glucometer (2354), or other medical instrumentation (EKG, etc.) (2355). For each of these MID data collections, the PHP may be configured to provide alerts based on ranges of input data values (2356), range-defined alert levels (different alert levels based on different data ranges) (2357), alerts based on delta values obtained in successive measurements (2358), and/or alerts based on number of manually collected MID data readings (2359). One skilled in the art will recognize that a variety of control structures may be utilized within the scope of MID data collection to affect a variety of alerts to prompt intervention of healthcare personnel for the benefit of the patient.

Reminders (240)

The PHP anticipates that patient and/or healthcare professional reminders (2460) may be triggered to support medication ingestion (2461), physician appointments (2462), and/or patient activity (2463) on a variety of timetables and schedules (2464, 2465, 2466, 2467, 2468, 2469).

End Care Plan Group (2470)

Each care plan group may be terminated with data indicia as indicated in FIG. 24 (2400) that indicates the end of the care plan group and a move upward in the PHP hierarchy. As indicated, each major element of the PHP may be nested with other elements or care plan groups as indicated in FIG. 21 (2100)-FIG. 24 (2400). This nesting capability permits formalized procedures for specific care plan actions to be defined and then applied to a given patient in a customized manner. For example, care plans for heart disease and diabetes may be formalized and standardized by healthcare administrative staff and then applied as HEART DISEASE and DIABETES care plan groups to the customized PHP for a given patient. Updating of these master HEART DISEASE and DIABETES care plan groups by healthcare administrators (as in the case of a hospital policy change) may then be automatically updated to all patients having these groups as part of their individual PHP. Furthermore, customized editing of these standard plans may be performed by healthcare personnel to meet the individual needs of each patient.

PHP Templates and Master Query Database (2500)

Figure 25:
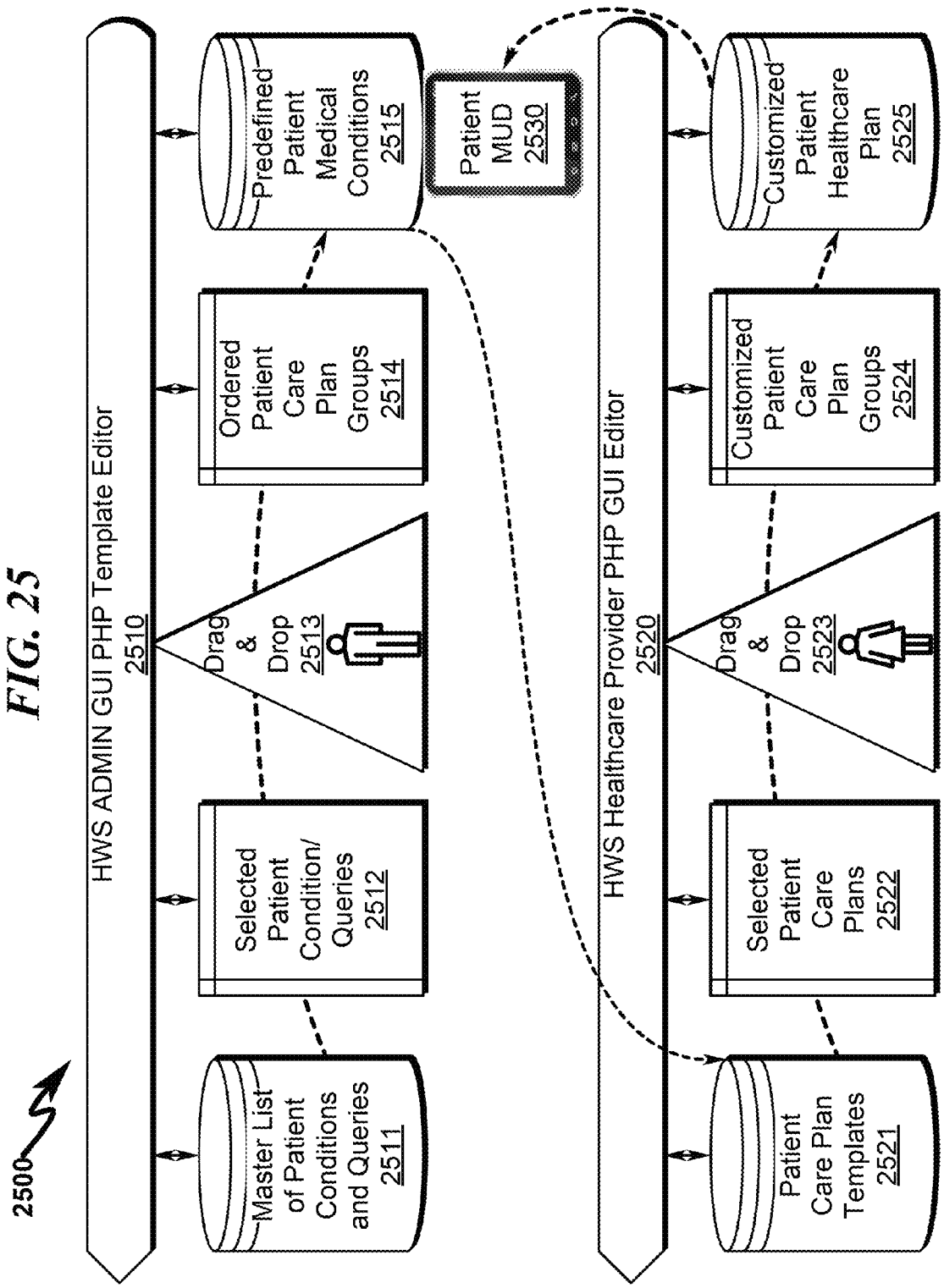
FIG. 25 illustrates an exemplary data flow diagram depicting creation of predefined care plan group templates from a master list of patient conditions and queries by administrative personnel followed by creation of customized patient care plans from these predefined group templates.

As generally illustrated in FIG. 25 (2500), the present invention anticipates that the creation of individualized patient healthcare plans (PHPs) may be accelerated and standardized via the use of Master Patient Condition/Query lists and Predefined Patient Medical Condition healthcare plans that are created and maintained at an administrative level of the healthcare system. This hierarchy of care standardization permits entire patient healthcare plans (PHPs) to be standardized based on industry standards of care as well as customized to the individual medical needs of each patient.

As depicted in FIG. 25 (2500), this multi-level care standardization begins with an ADMIN GUI template editor web interface (2510) in the HWS that allows a database (2511) containing a master list of patient conditions and/or patient queries to be edited by healthcare administrative staff to include healthcare plan information for all possible known medical conditions. This information might include standardized healthcare remote monitoring scenarios for patients in addition to associated patient queries, acceptable responses, and triggered alert conditions. From this broad database (2511) of information the ADMIN user selects specific patient conditions and/or patient queries (2512) and via a GUI drag-and-drop interface (2513) orders these into patient care groups (2514) within the template editor GUI (2510). These coordinated PHP templates for healthcare are then stored in a database (2515) that defines predefined patient medical conditions and the associated healthcare plan groups that should be associated with each medical condition.

Once the PHP template database (2515) has been populated, a healthcare worker using a provider PHP GUI editor (2520) on the HWS accesses one or more patient care plan templates (2521) based on the previously defined patient medical conditions (2515) database and selects specific care plan groups (2522) via a GUI drag-and-drop interface (2523) and orders these into customized patient care plan groups (2524) which are then stored in a database (2525) as a customized patient healthcare plan (PHP) for later dissemination by the HWS to the patient MUD (2530).

This nested approach to the definition of standardized healthcare plans provides two significant advantages over the prior art, including but not limited to:
  Healthcare administrators may standardize healthcare plans for a variety of medical conditions.
  Updates to standardized healthcare plans may trigger across-the-board application of new healthcare policies to all patients participating in the individual care plan group. For example, a change in protocol for diabetes patients could be modified at the administrative level and immediately trigger a PHP update to innumerable patients that are monitored with this medical condition.

Healthcare providers need not have intimate knowledge of acceptable care plans for each medical condition, but rather can use predefined protocols for patient care.

Healthcare providers may mix-and-match predefined care plan groups from the care plan group templates as well as create additional customized care plan groups for the patient that are tailored to the medical needs of each patient. This integration of standardized care plans with patient customization permits administrative control of the standard of patient care but also allows customization of patient care based on changing patient medical conditions.

Thus, the creation of individualized PHP datasets for each patient may have components of standardized healthcare plans as well as individualized healthcare activity associated with each patient.

Exemplary HWS Main Web Browser Interface (2600)-(2700)

Figure 26:
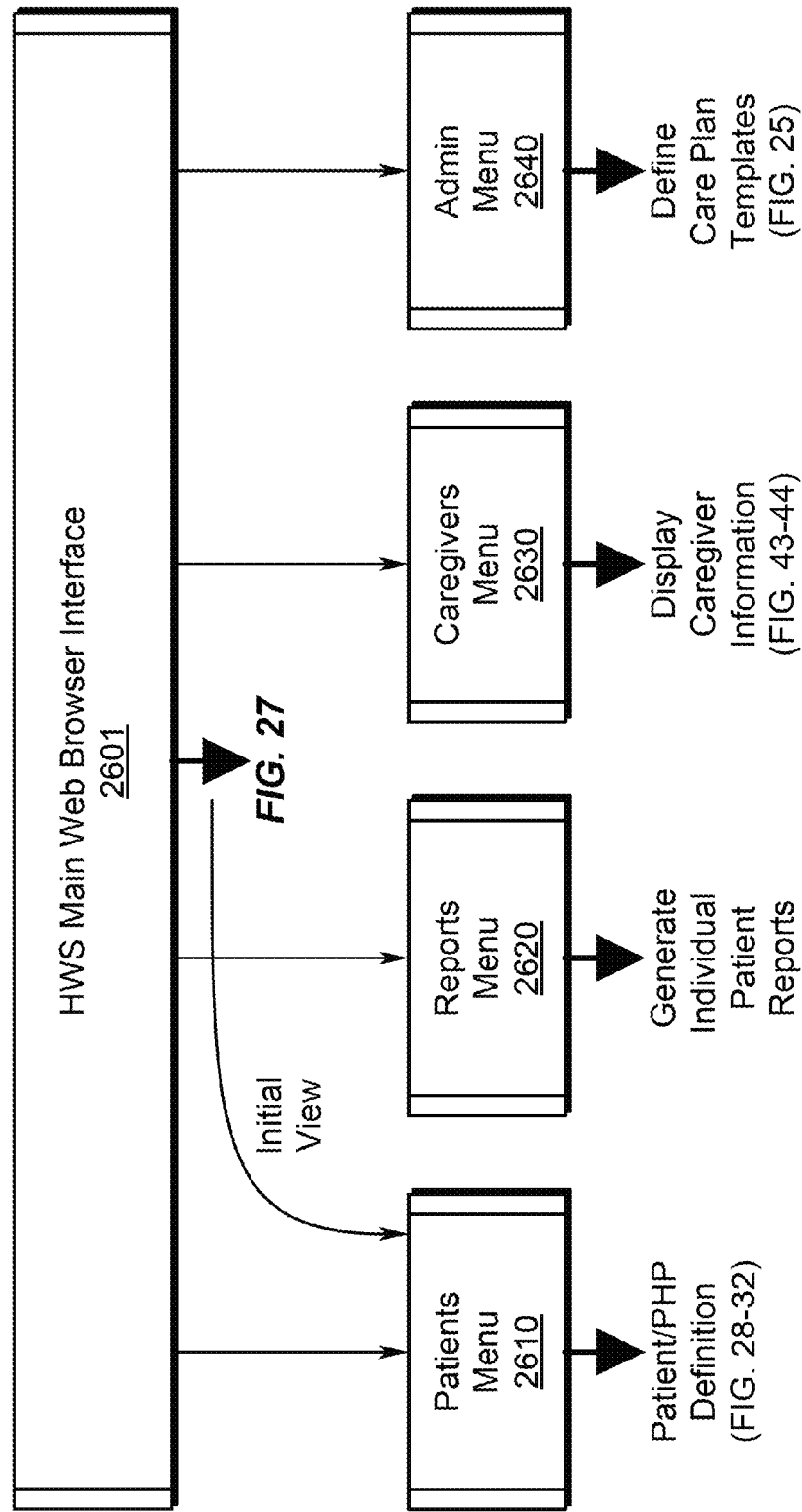
FIG. 26 illustrates a menu overview of an exemplary HWS main web browser interface.

While the HWS may be configured in many ways, an exemplary top level menu structure is depicted in FIG. 26 (2600) wherein the browser interface (2610) comprises a patients menu (2610), reports menu (2620), caregivers menu (2630), and administration menu (2640). The patients menu (2610) is the main portal to drive patient care via the PHP. The reports menu (2620) permits individual patient reports to be generated. The caregivers menu (2630) defines information regarding individual health caregivers. The administration menu (2640) provides supervisory functions such as the capability of defining patient care plan templates and defining overall standard of care for all patients being serviced.

Figure 27:
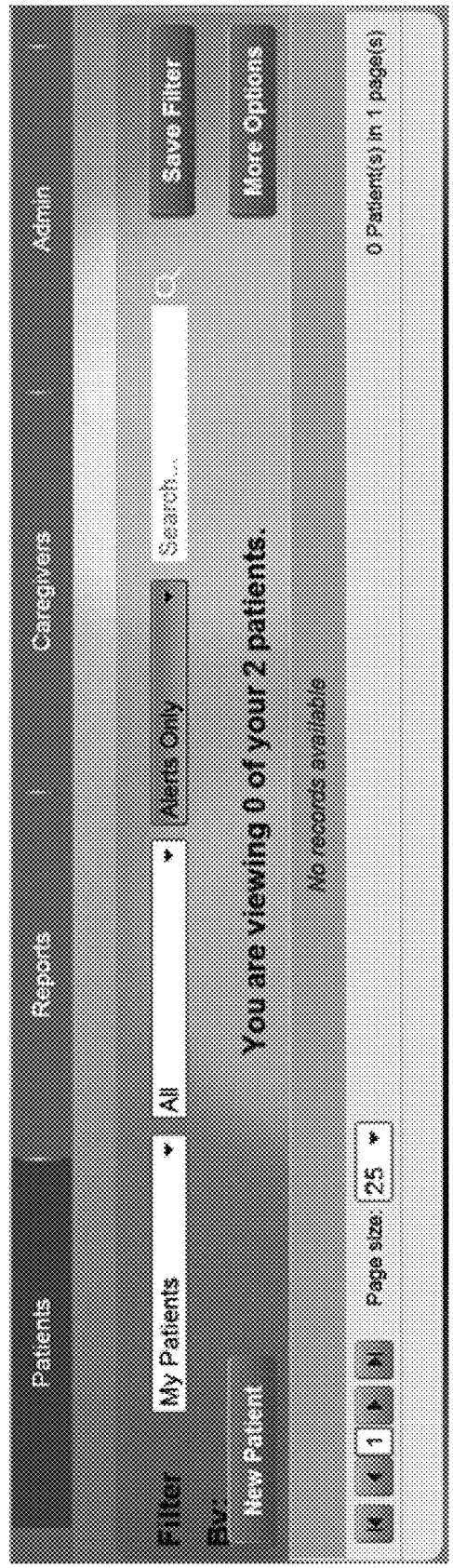
FIG. 27 illustrates a screenshot of an exemplary HWS main web browser interface.

A screenshot of an exemplary HWS main browser interface is depicted in FIG. 27 (2700).

Exemplary HWS Patient Dialogs (2800)-(3200)

Figure 28:
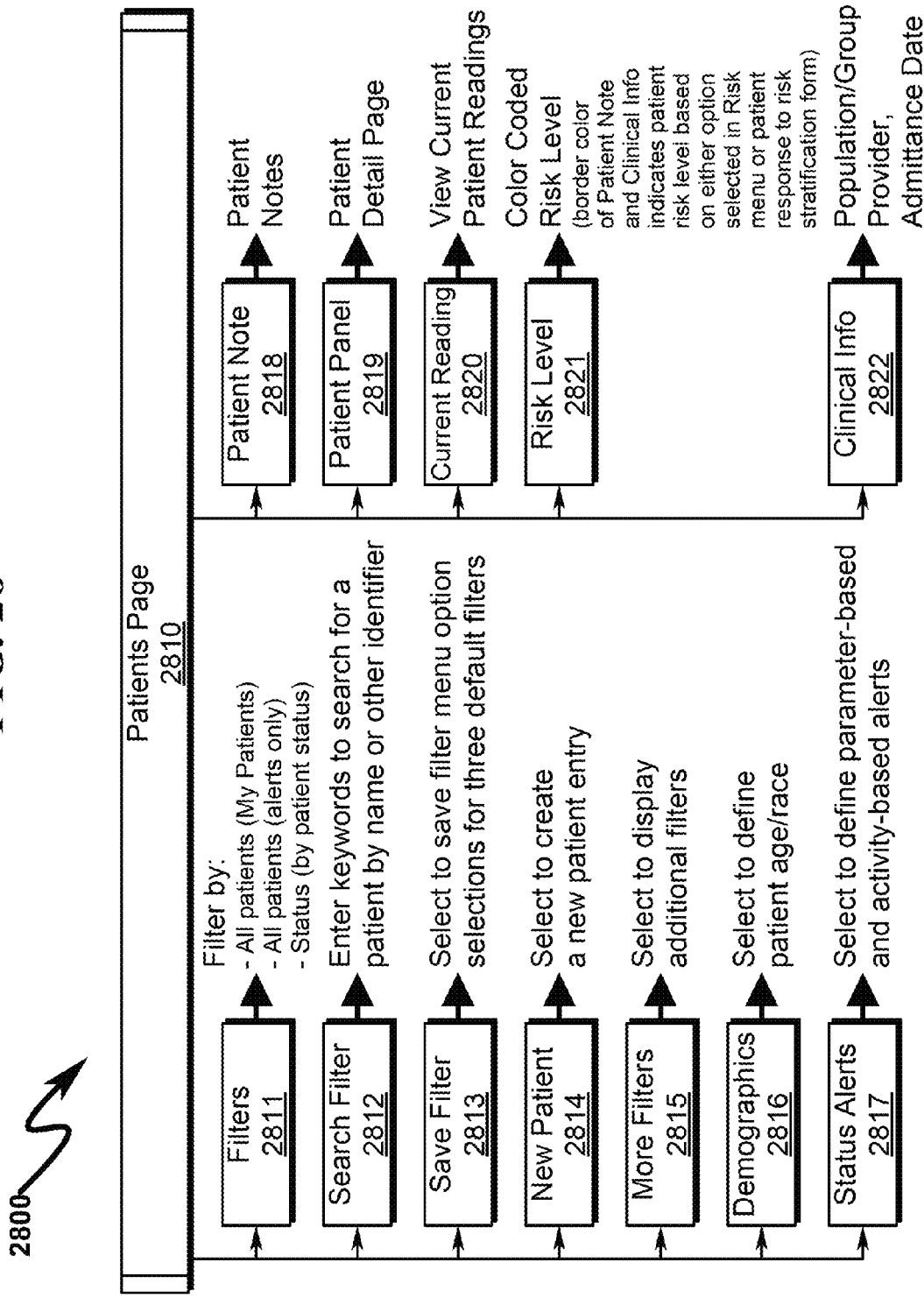
FIG. 28 illustrates a menu overview of an exemplary HWS patient web browser interface.
Figure 29:
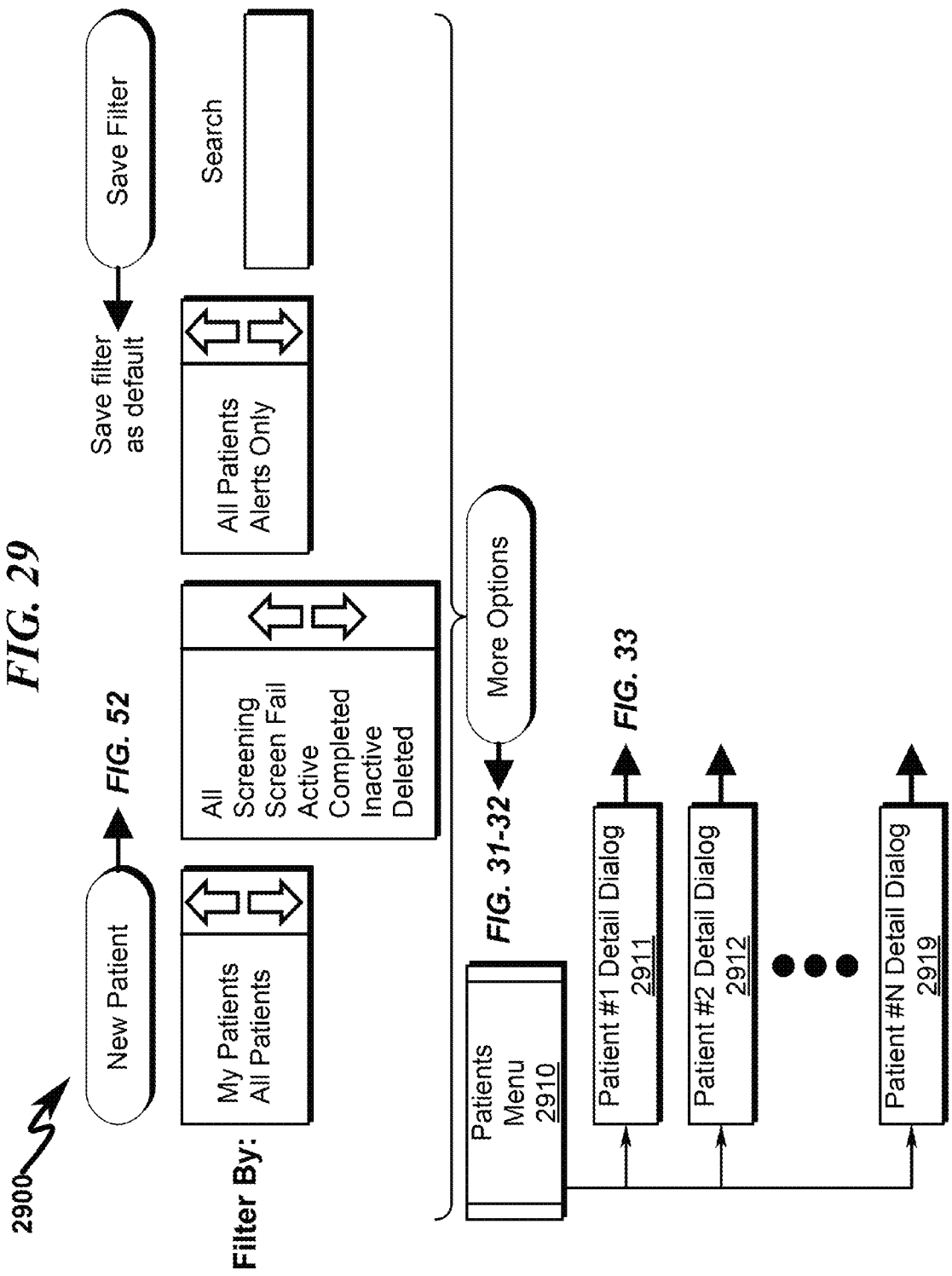
FIG. 29 illustrates a menu overview of an exemplary HWS patient filtering interface.
Figure 30:
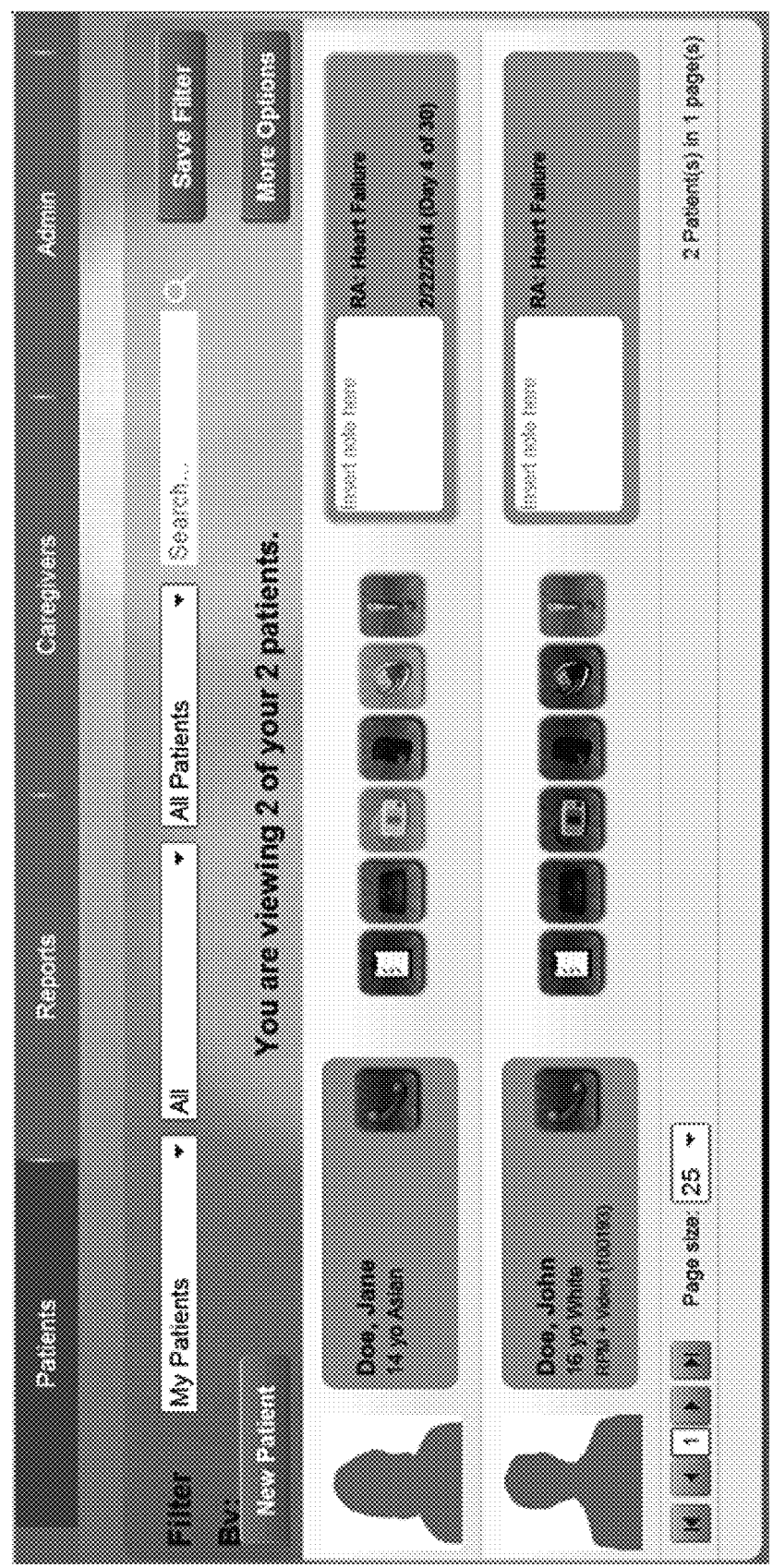
FIG. 30 illustrates a screenshot of an exemplary HWS patient filtering interface.
Figure 31:
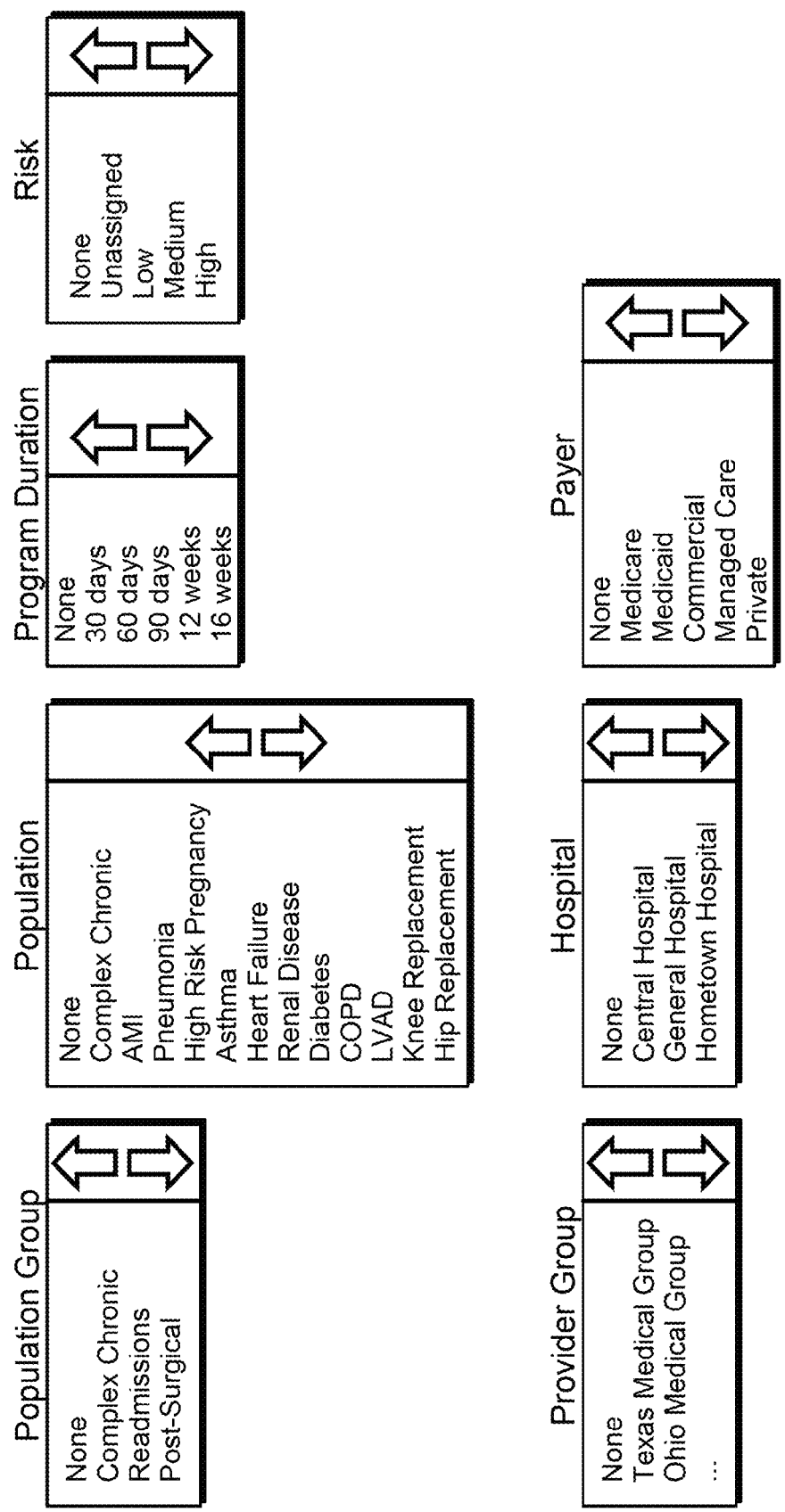
FIG. 31 illustrates a menu overview of an exemplary HWS detail patient filtering interface.
Figure 32:
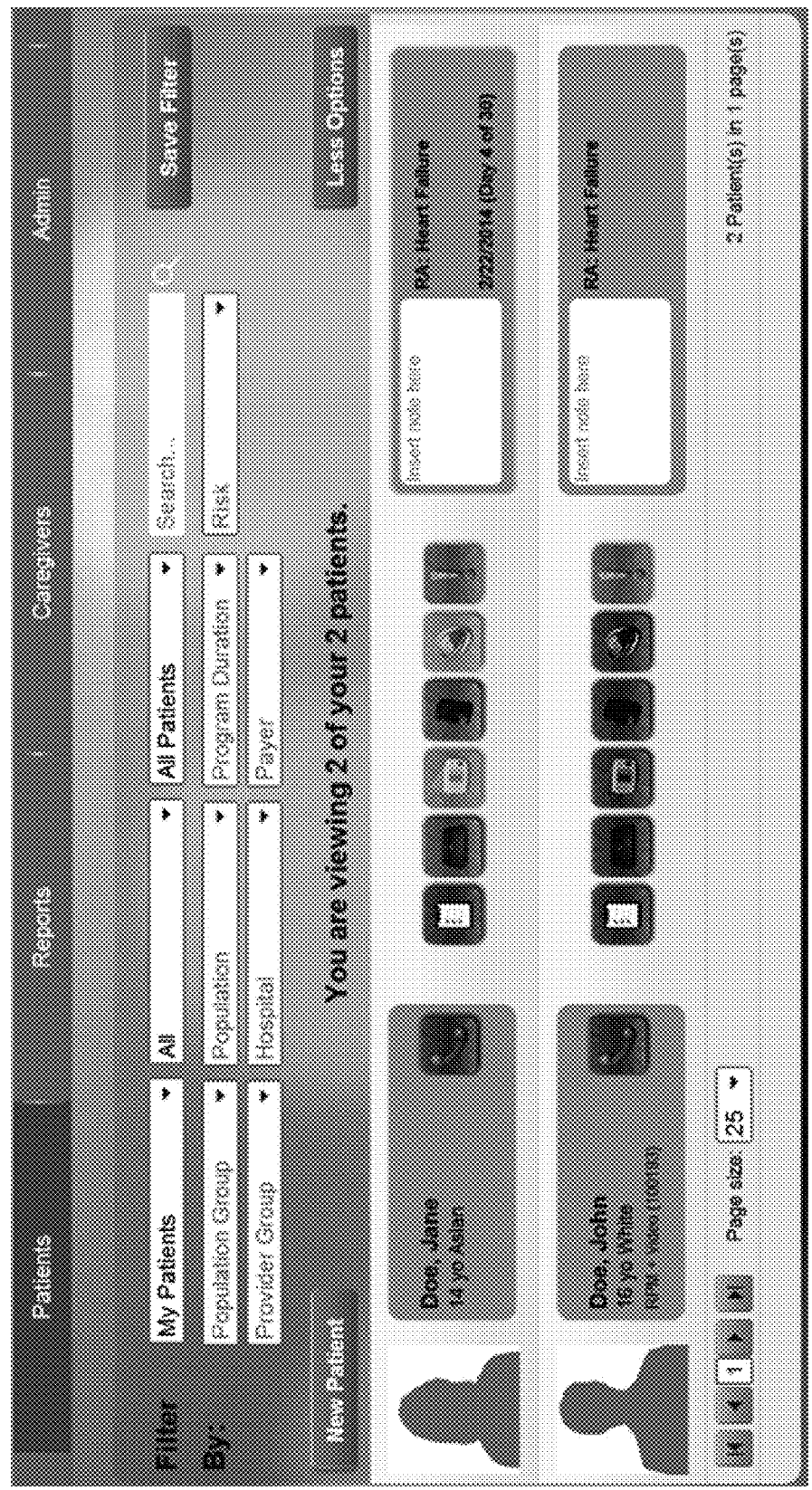
FIG. 32 illustrates a screenshot of an exemplary HWS detail patient filtering interface.

FIG. 28 (2800)-FIG. 32 (3200) provide additional detail on exemplary patient definition dialogs that may be employed by the HWS to permit health caregivers the ability to both define patients in the system and define alerts associated with the patient.

Exemplary HWS Patient Detail Dialogs (3300)-(4000)

Figure 33:
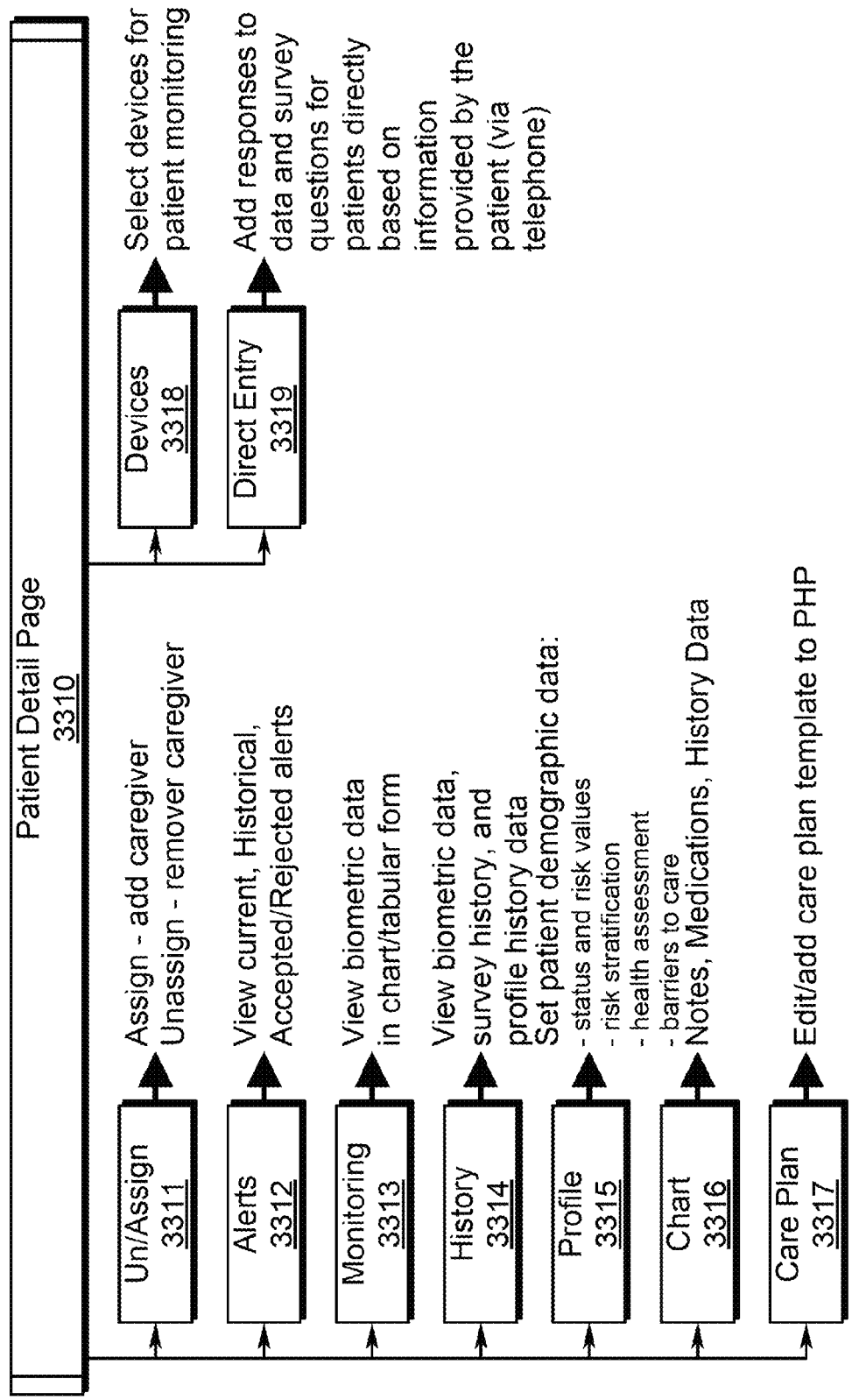
FIG. 33 illustrates a menu of an exemplary HWS detail patient display.
Figure 40:
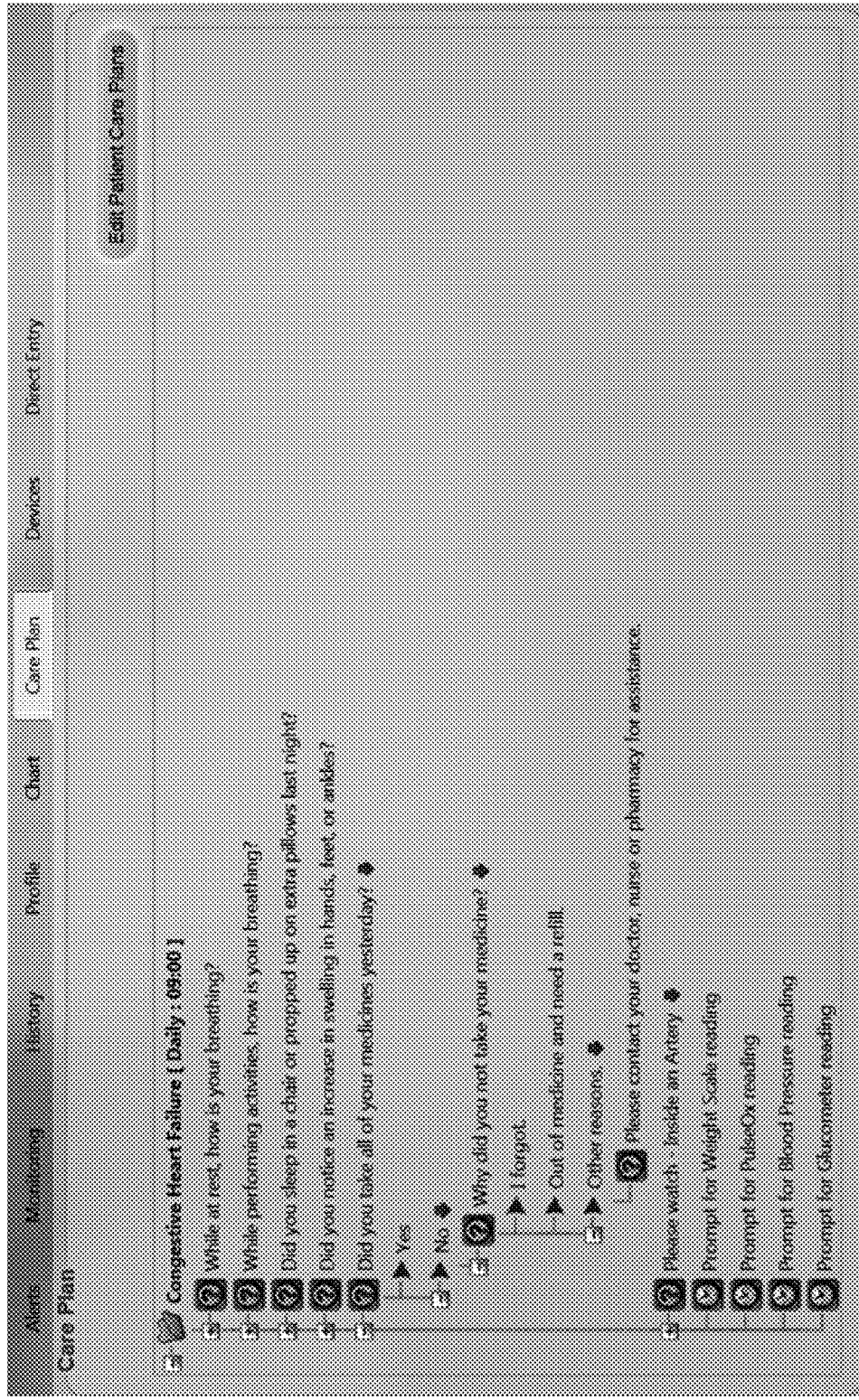
FIG. 40 illustrates an exemplary patient care plan web browser screenshot.

FIG. 33 (3300)-FIG. 40 (4000) illustrate exemplary patient detail definition dialogs that may be employed by the HWS to permit health caregivers the ability to both define patients in the system and define alerts associated with the patient.

Figure 34:
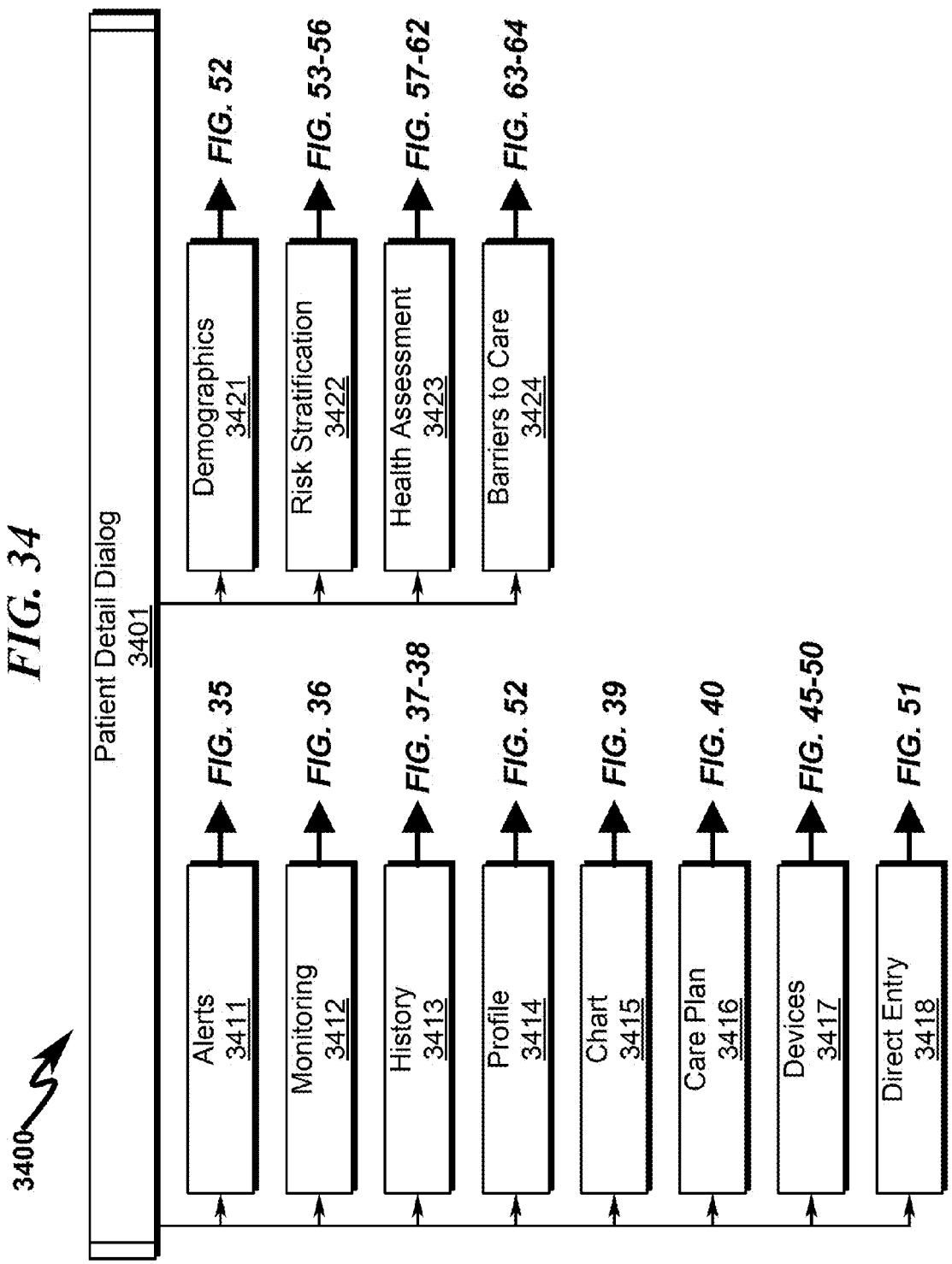
FIG. 34 illustrates a menu of an exemplary HWS detail patient web browser display and depicts sub-functions associated with the patient care.
Figure 35:
FIG. 35 illustrates an exemplary patient alert web browser screenshot.
Figure 36:
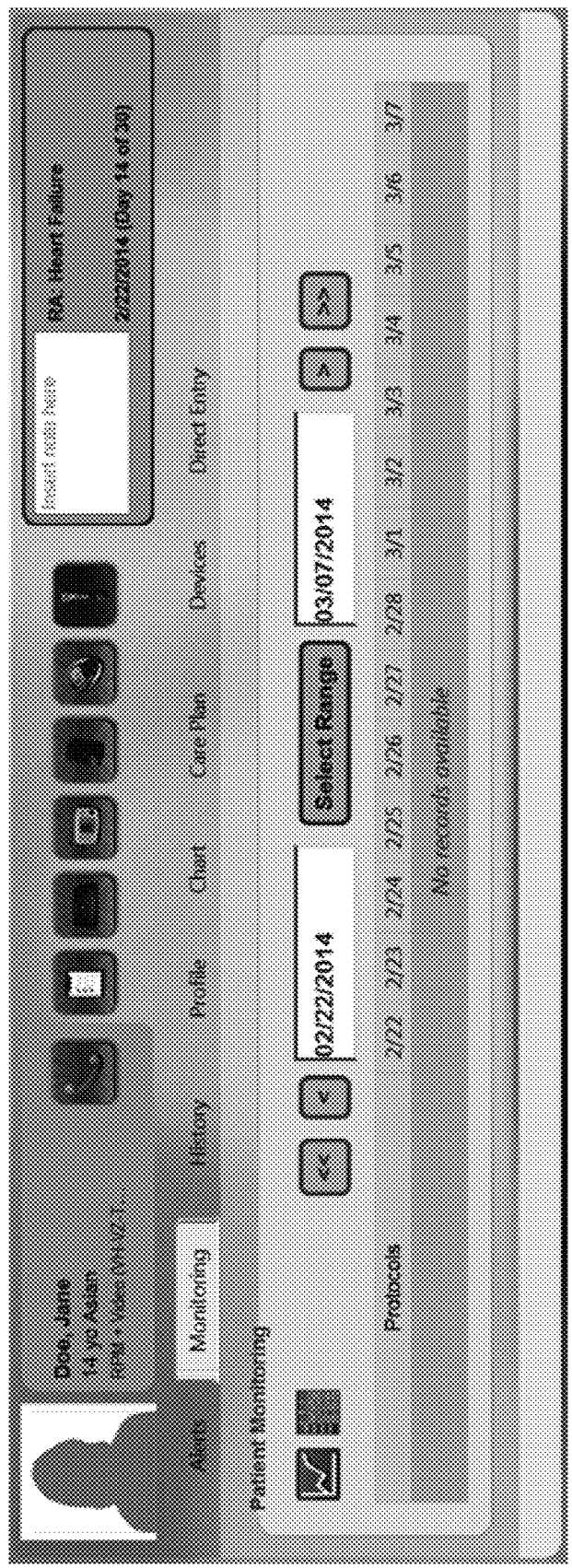
FIG. 36 illustrates an exemplary patient monitoring web browser screenshot.
Figure 37:
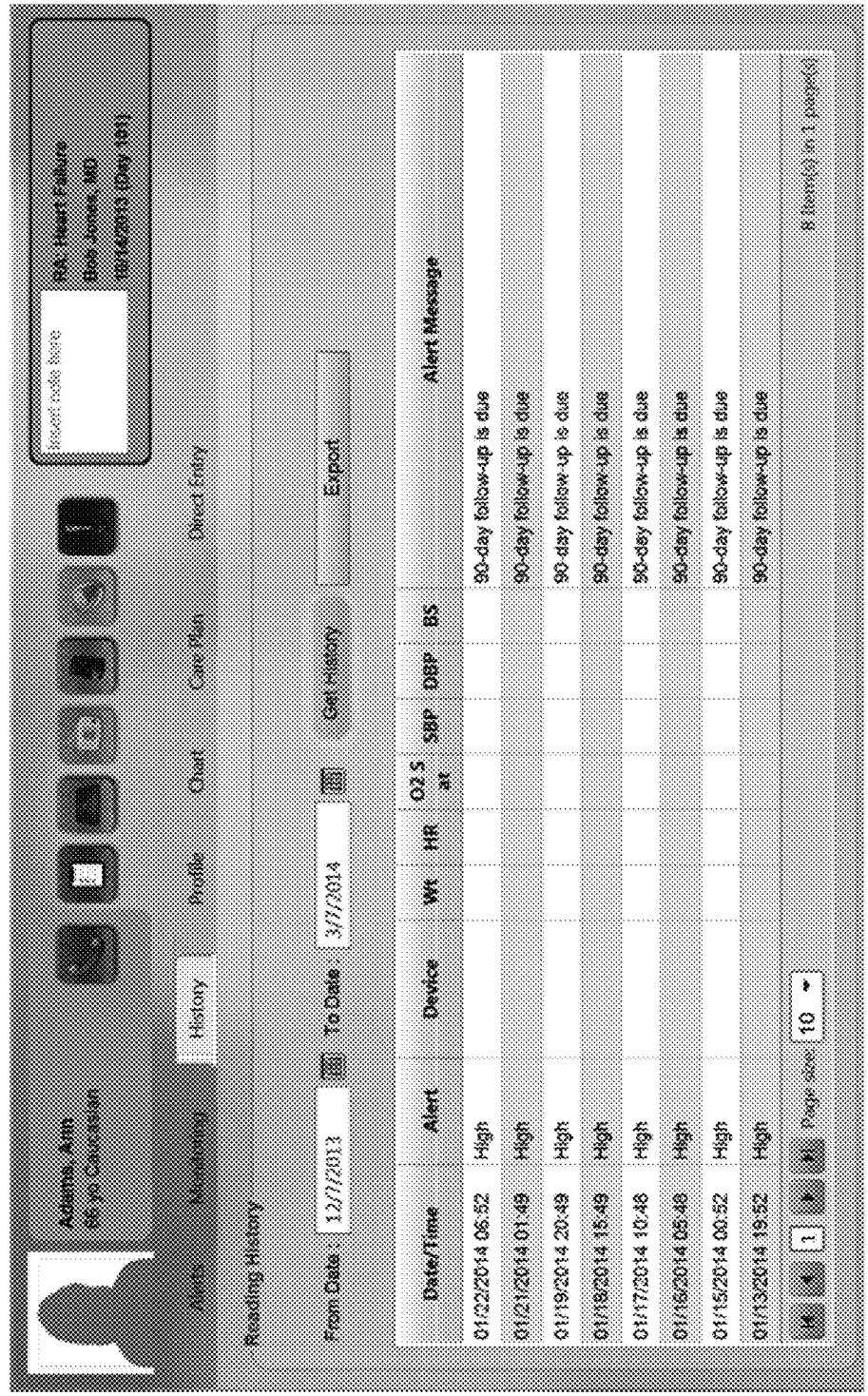
FIG. 37 illustrates an exemplary patient reading history web browser screenshot.
Figure 39:
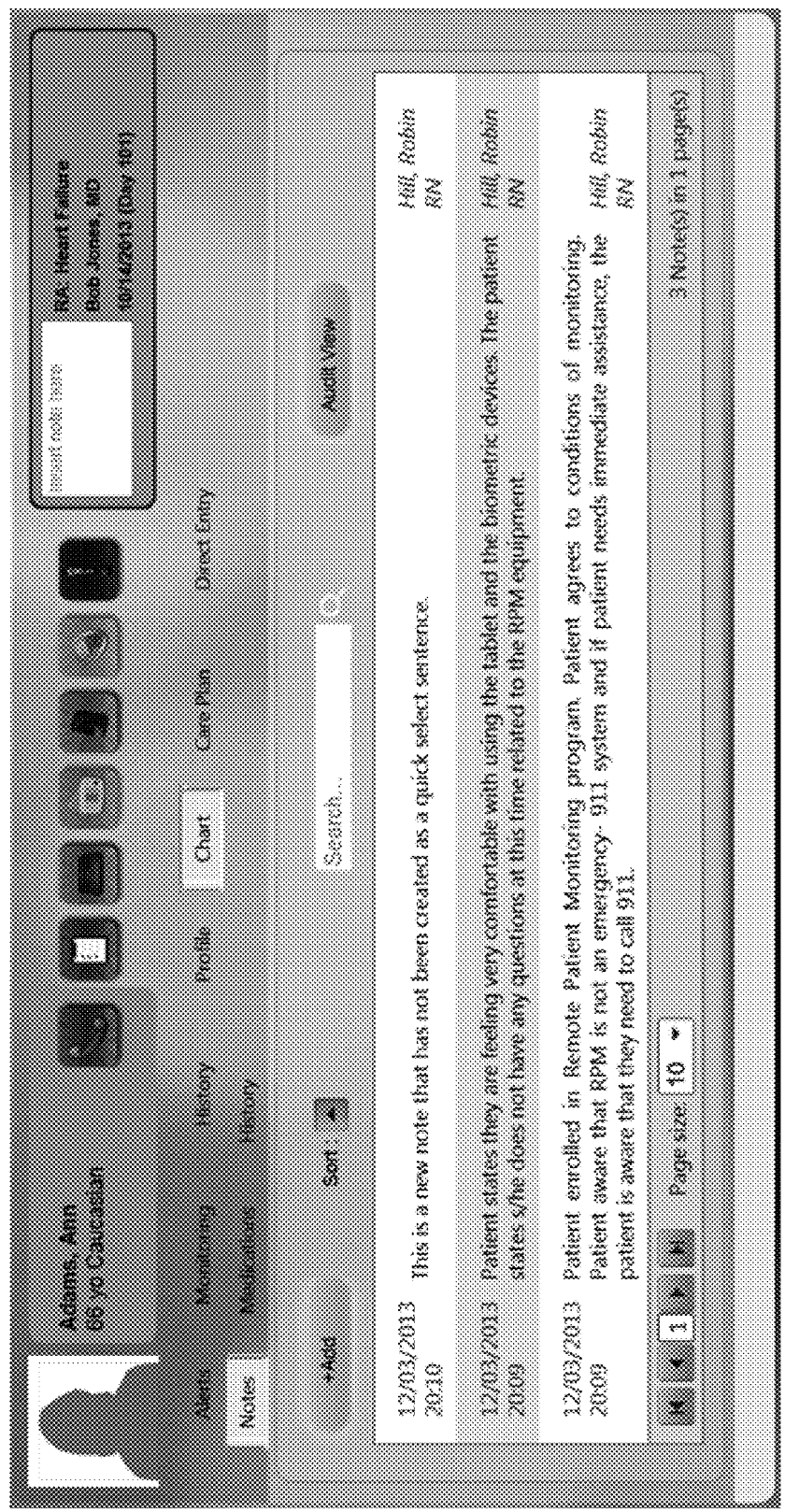
FIG. 39 illustrates an exemplary patient chart web browser screenshot.

FIG. 33 (3300) provides an overview of the various submenus available in the patient definition web interface, including options to assign/unassign caregivers (3311), display patient alerts (3312), view real-time biometric data (3313), view patient history (3314), view/edit patient profile information (3315), view/edit the patient chart (3316), view/edit the patient healthcare plan (PHP) (3317), view/edit the patient MID hardware complement (3318), and provide for direct entry of patient medical data and query responses (3319). FIG. 34 (3400) illustrates how these menus are related to screenshots provided in the drawings that depict exemplary embodiments of each of these submenu elements.

Exemplary PHP Edit/Display Dialog Structure (4000)-(4100)

Figure 41:
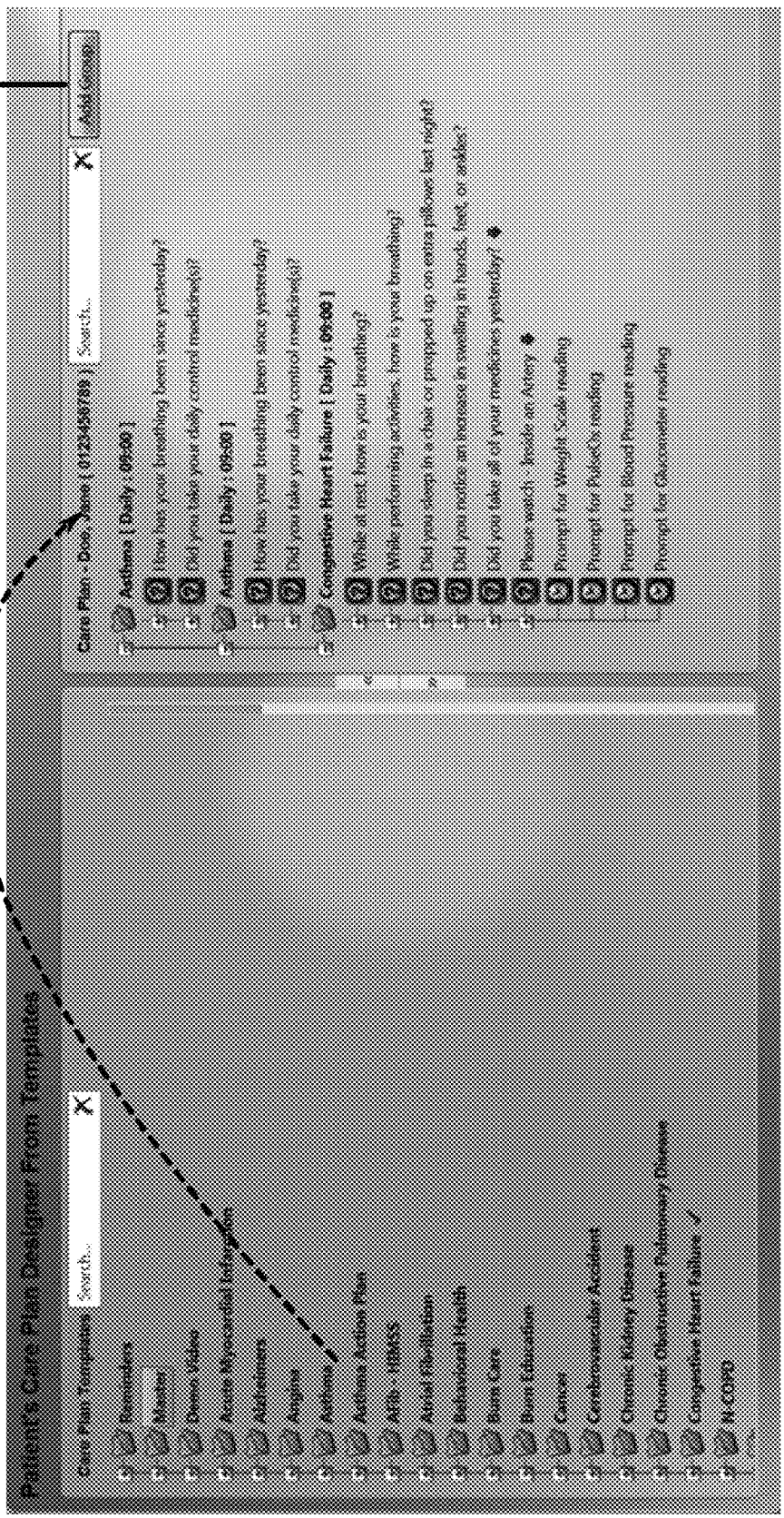
FIG. 41 illustrates an exemplary caregiver PHP editing dialog screenshot.
Figure 42:
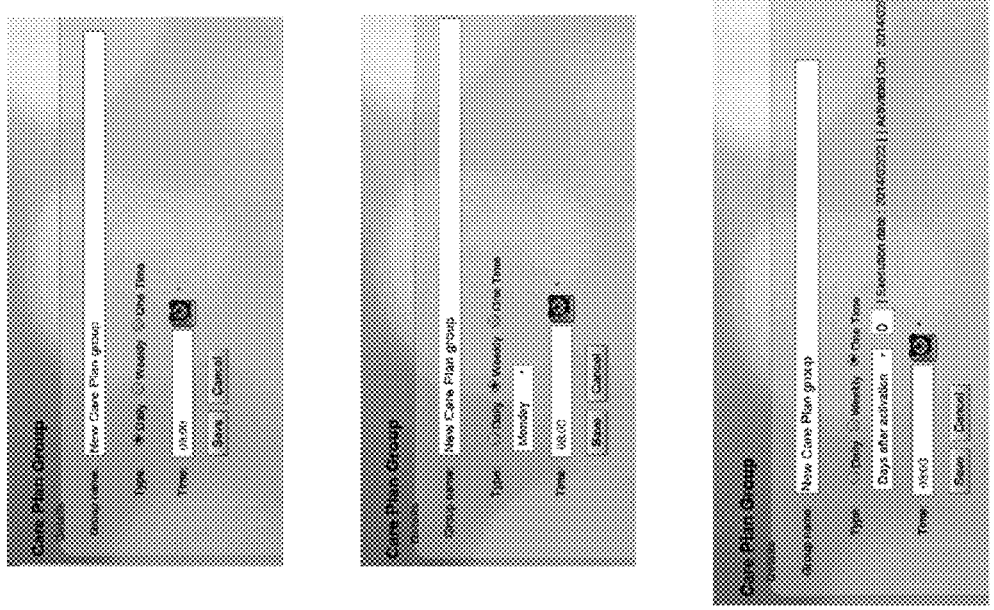
FIG. 42 illustrates a exemplary caregiver PHP editing dialog screenshots depicting creation of new care plan groups.
Figure 43:
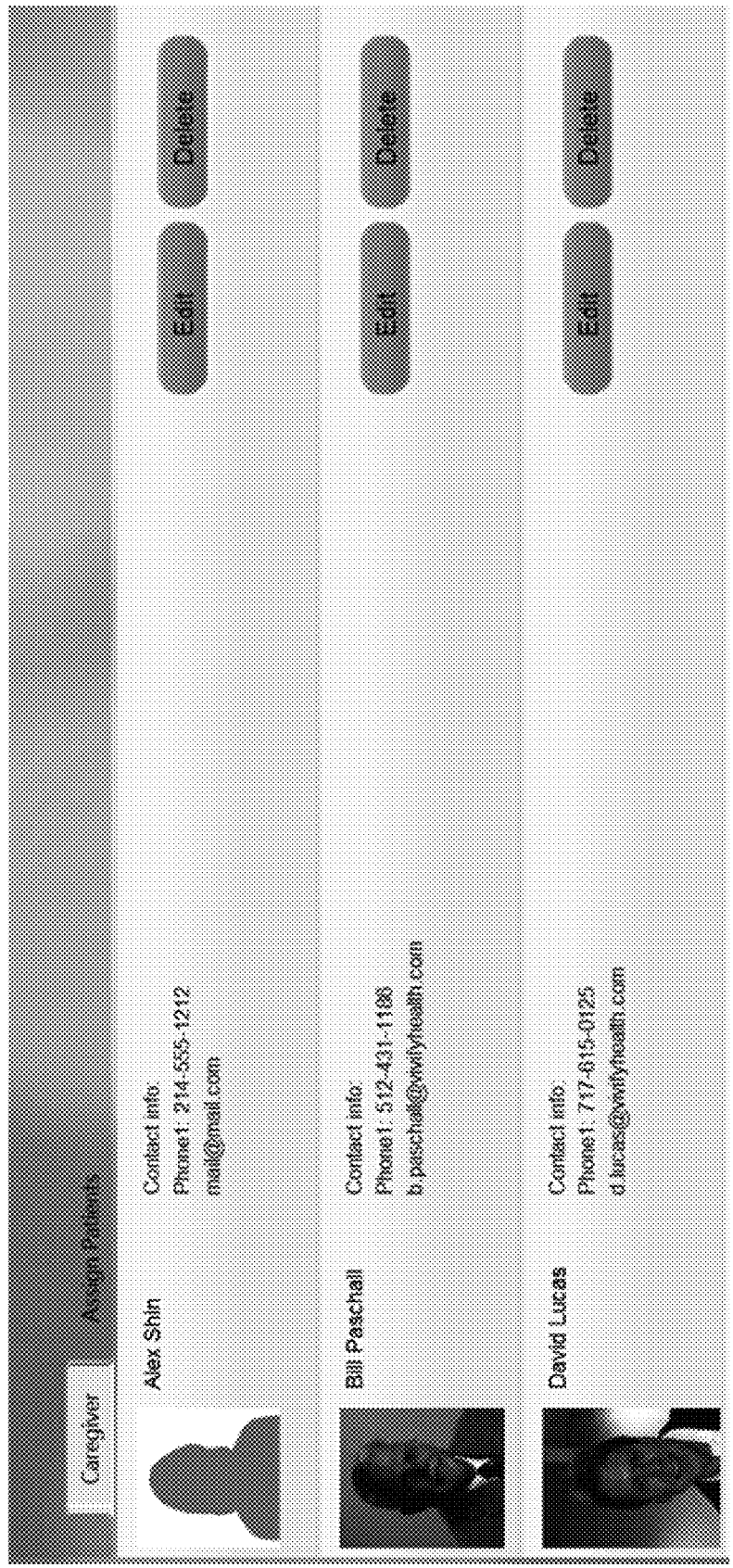
FIG. 43 illustrates an exemplary caregiver definition dialog screenshot.
Figure 44:
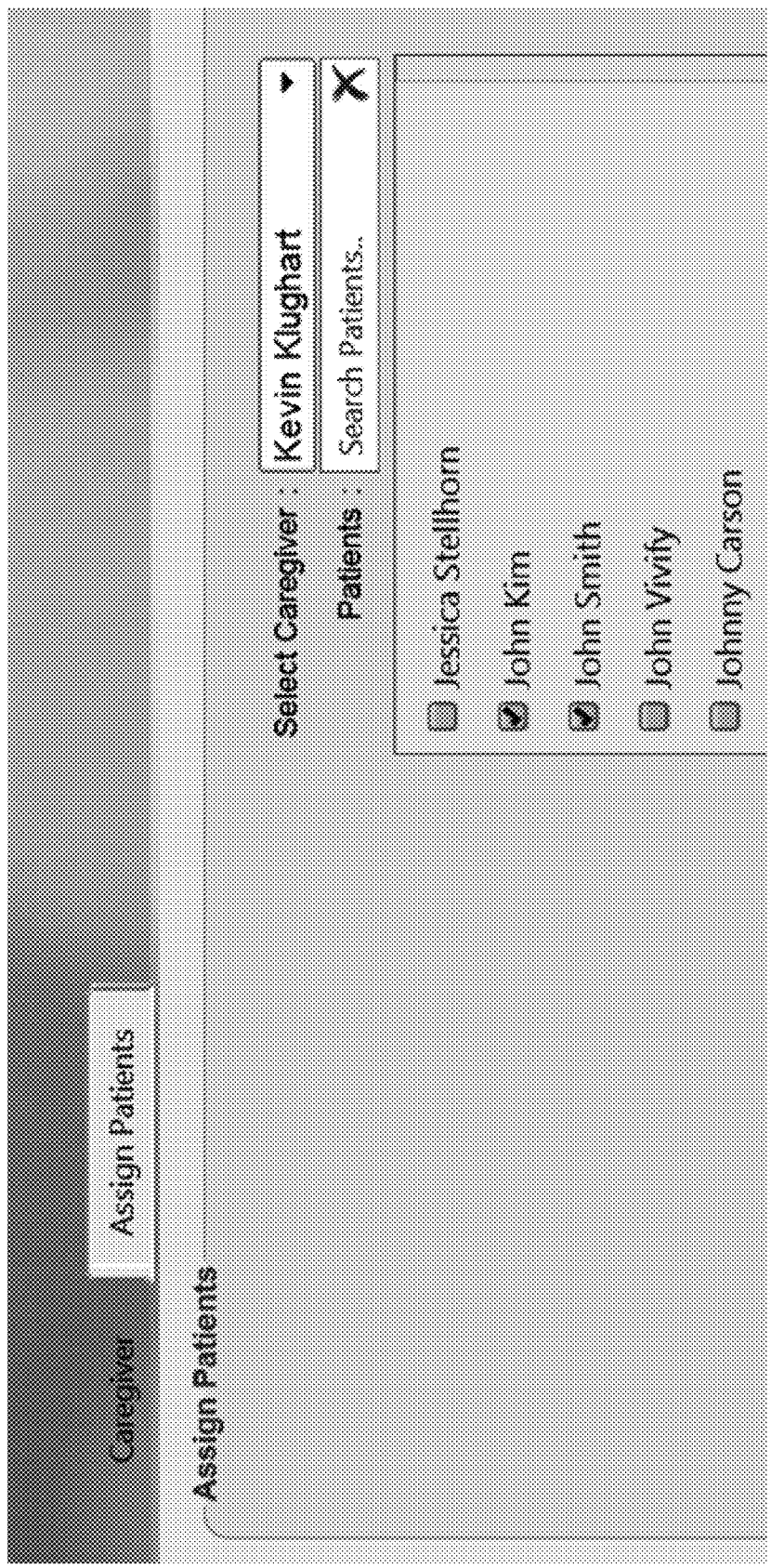
FIG. 44 illustrates an exemplary caregiver-to-patient association definition dialog screenshot.

An exemplary PHP hierarchical structure presented for healthcare provider editing via a HWS GUI is displayed in the dialogs depicted in FIG. 40 (4000)-FIG. 41 (4100). These display dialogs depict the hierarchical nature of the PHP as well as a variety of timed patient medical reading triggers, patient questionnaires, and response triggered audio/video educational content that may be presented to the patient.

This PHP hierarchy is maintained and updated by the healthcare provider on the HWS. The HWS is then responsible for disseminating the PHP to the MUD so that the MUD may autonomously execute the PHP without need for further instruction from the HWS. This permits independent operation without the need for a "master" controlling system, and allows independent collection of patient information in the event of communication loss with the HWS.

As depicted in FIG. 41 (4100), the PHP may be constructed by the healthcare provider using a graphical user interface (GUI) as a hierarchy of patient dialogs that are triggered at certain times of the day. These care plans may be constructed as custom care plans or derived from care plan templates that are specific to certain types of diseases or other medical conditions.

Within this context, it is anticipated that PHP patient care plan templates associated with specific diseases and medical conditions may be used as the basis for the creation of a custom PHP patient care plan. For example, patients having a history of heart disease may be placed on a common PHP that may be managed at a global level and updated as necessary to cover a wide variety of patient conditions. This template-assisted PHP generation process anticipates that a graphical user interface (GUI) may be used to drag-and-drop templates into a custom patient PHP care plan.

The PHP as defined may incorporate a variety of custom patient questions and queries that when answered by the patient trigger specific healthcare alert levels to be logged by the HWS for distribution to appropriately authorized healthcare professionals associated with the care of the patient. These patient queries may in some preferred invention embodiments incorporate responses selected from a group consisting of: single selections; multiple selections; and yes/no responses. However, other query formats may also be incorporated into this hierarchy as well. A variety of alert levels may be associated with each patient response, including but not limited to response alert values selected from a group consisting of: no alert; medium alert; and high alert. This alert level granularity may be increased without loss of generality in the teachings of the present invention.

Exemplary MID Alert Definitions (4500)-(5000)

The medical instrumentation device (MID) as it communicates patient information to the mobile user device (MUD) may be controlled by the MUD via the downloaded patient healthcare plan (PHP) to affect a number of calendared or periodic patient measurements. These patient measurement once taken by the MID may be used by the MUD to generate alerts based on a variety of factors. These include but are not limited to the following:

Upper and/or lower range MID values. Each patient MID reading may be associated with an upper and/or lower range value. Alerts may be triggered if the measured MID value exceeds these upper/lower range values. For example, an alert may be triggered for measured heart rates below 50 and above 100.

Multiple upper/lower range MID values. Each patient MID reading may be associated with a plurality of upper and/or lower range values, with each of these range values associated with a risk stratification alert level. Risk stratified alerts may be triggered if the measured MID value exceeds these upper/lower range values. For example, a medium alert level may be triggered for heart rates below 60 and above 80, whereas a high alert level may be triggered for pulse rates less than 40 or greater than 100.

Differential delta values. Multiple MID values may be collected and if differentials between these values exceed certain thresholds, an alert may be triggered. For example a differential patient weight reading of 10 pounds taken over a period of two days might trigger an alert.

Failure of said patient to execute a biometric measurement. If the patient fails to take a MID biometric reading when scheduled this may be configured within the PHP to trigger an alert. For example, if the patient was scheduled to collect a blood pressure reading at noon and failed to do so, the PHP may be configured to trigger an alert. This may be configured to inform a healthcare professional of the measurement failure as well as send an audio/video reminder to the patient via the MUD.

Entry of multiple manual biometric measurement entries from said patient. The patient may in some circumstances manually enter some biometric data, such as weight, blood pressure, etc. The PHP may be configured to trigger an alert if manual data entry by the patient exceeds a certain threshold absent an intervening automated measurement. For example, the PHP may be configured to trigger an alert if more than weight readings are entered manually without an intervening automated weight scale reading being collected.

Periodic triggering of biometric measurements. The PHP may be configured to force biometric measurements to be collected from the patient on a periodic basis. For example, reminders may be sent to collect glucose and blood pressure measurements at noon every day and weight readings every Saturday.

Periodic triggering of manual/automatic biometric measurements. The PHP may be configured to force manual and/or biometric measurements to be collected from the patient on a periodic basis. For example, reminders may be sent to manually collect glucose and blood pressure measurements at noon every day and automated weight readings every Saturday.

Figure 45:
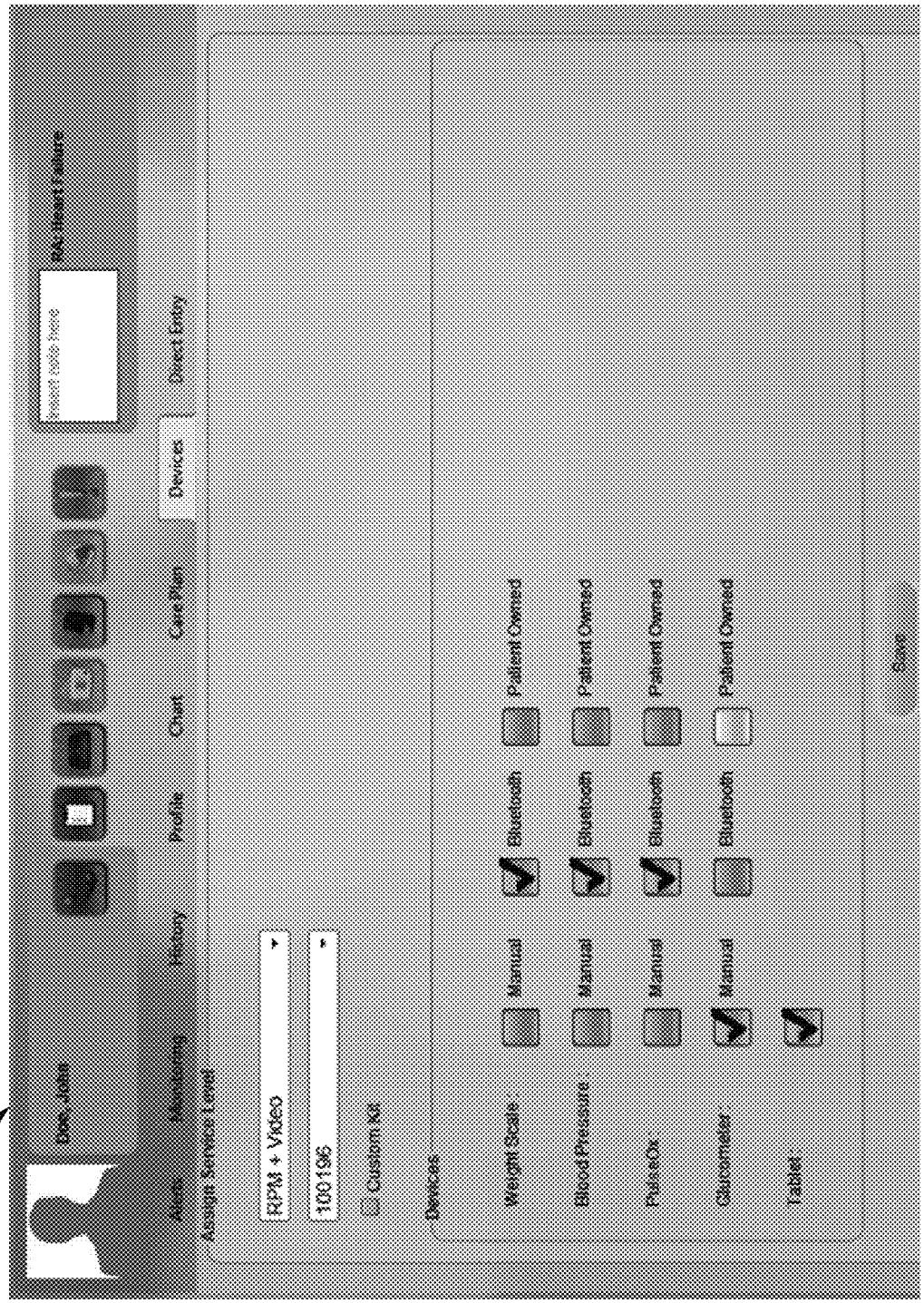
FIG. 45 illustrates an exemplary remote patient monitoring device setup dialog.
Figure 46:
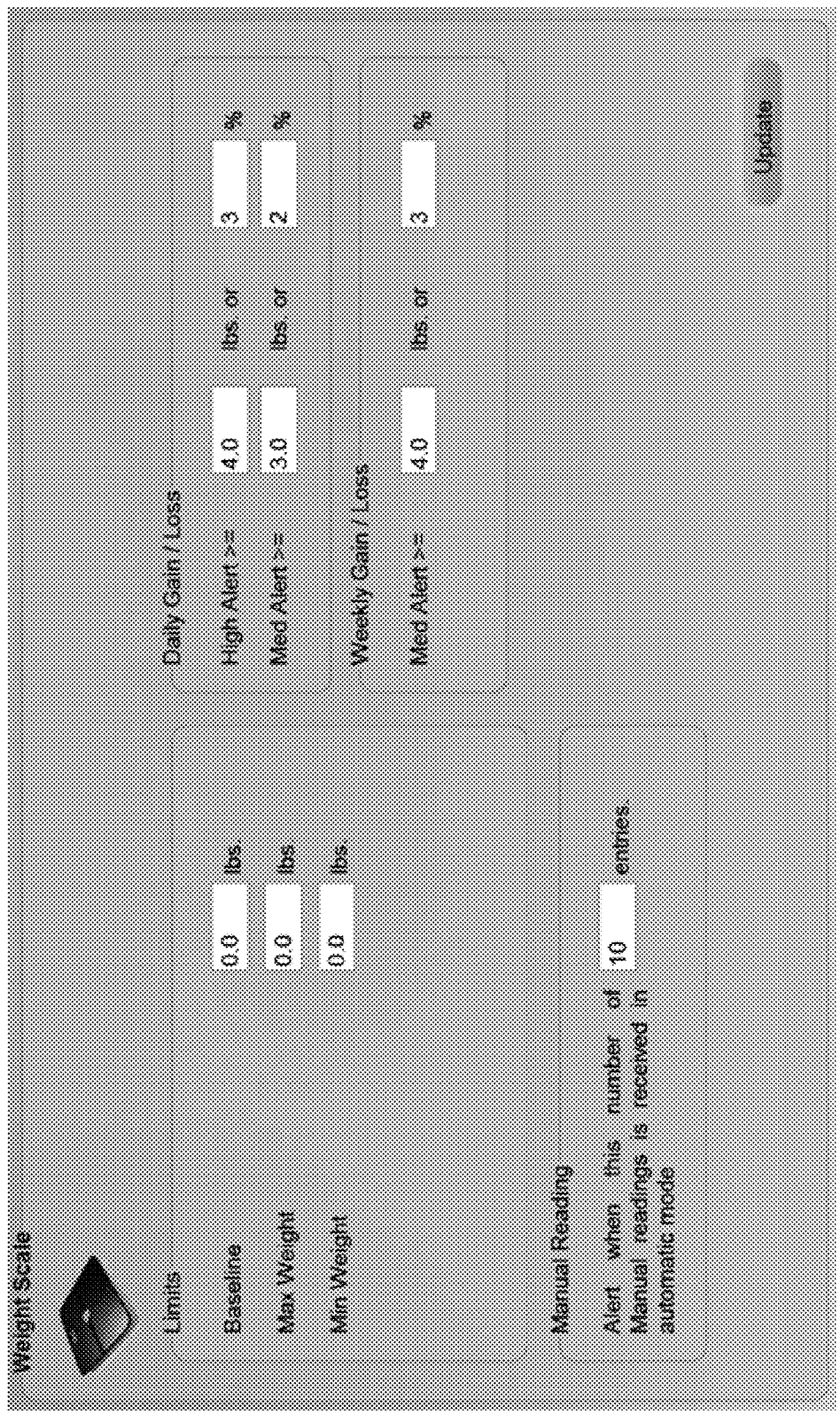
FIG. 46 illustrates an exemplary PHP weight scale alert configuration dialog.
Figure 47:
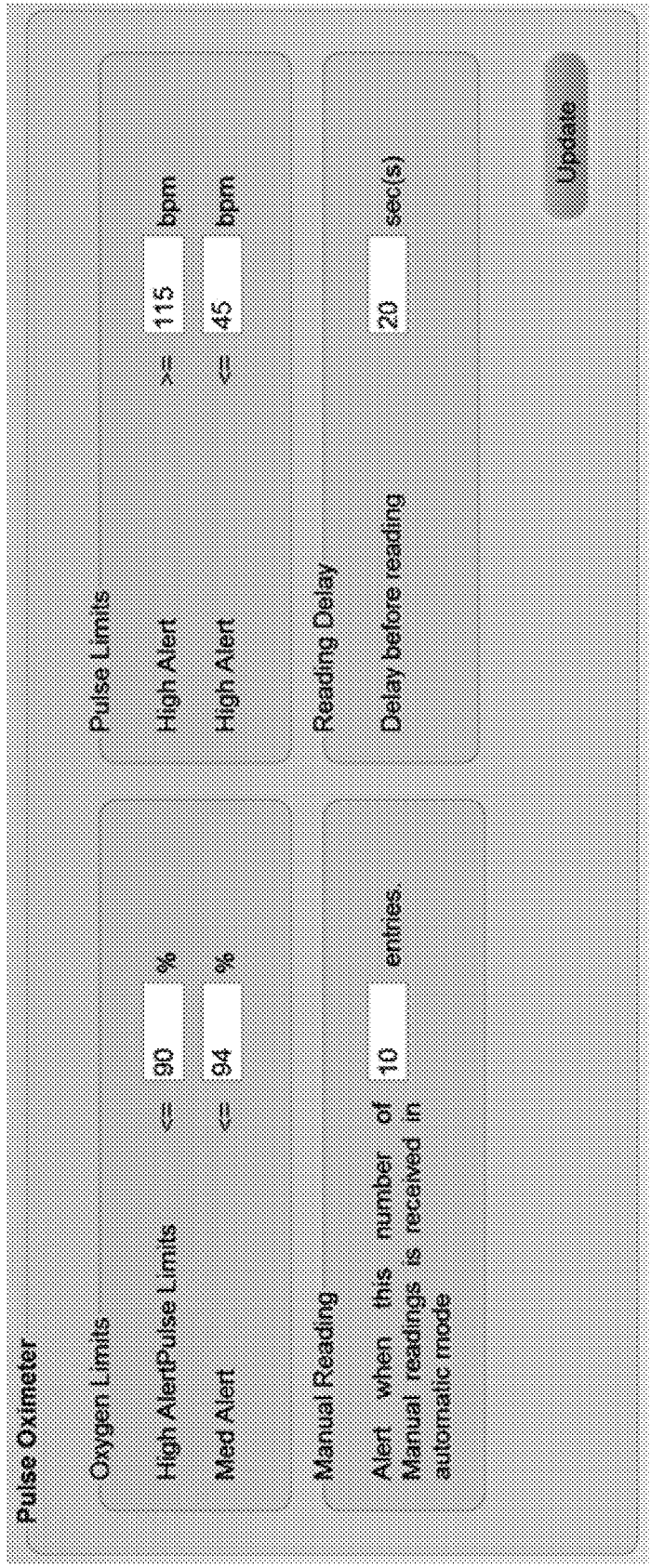
FIG. 47 illustrates an exemplary PHP pulse oximeter alert configuration dialog.
Figure 48:
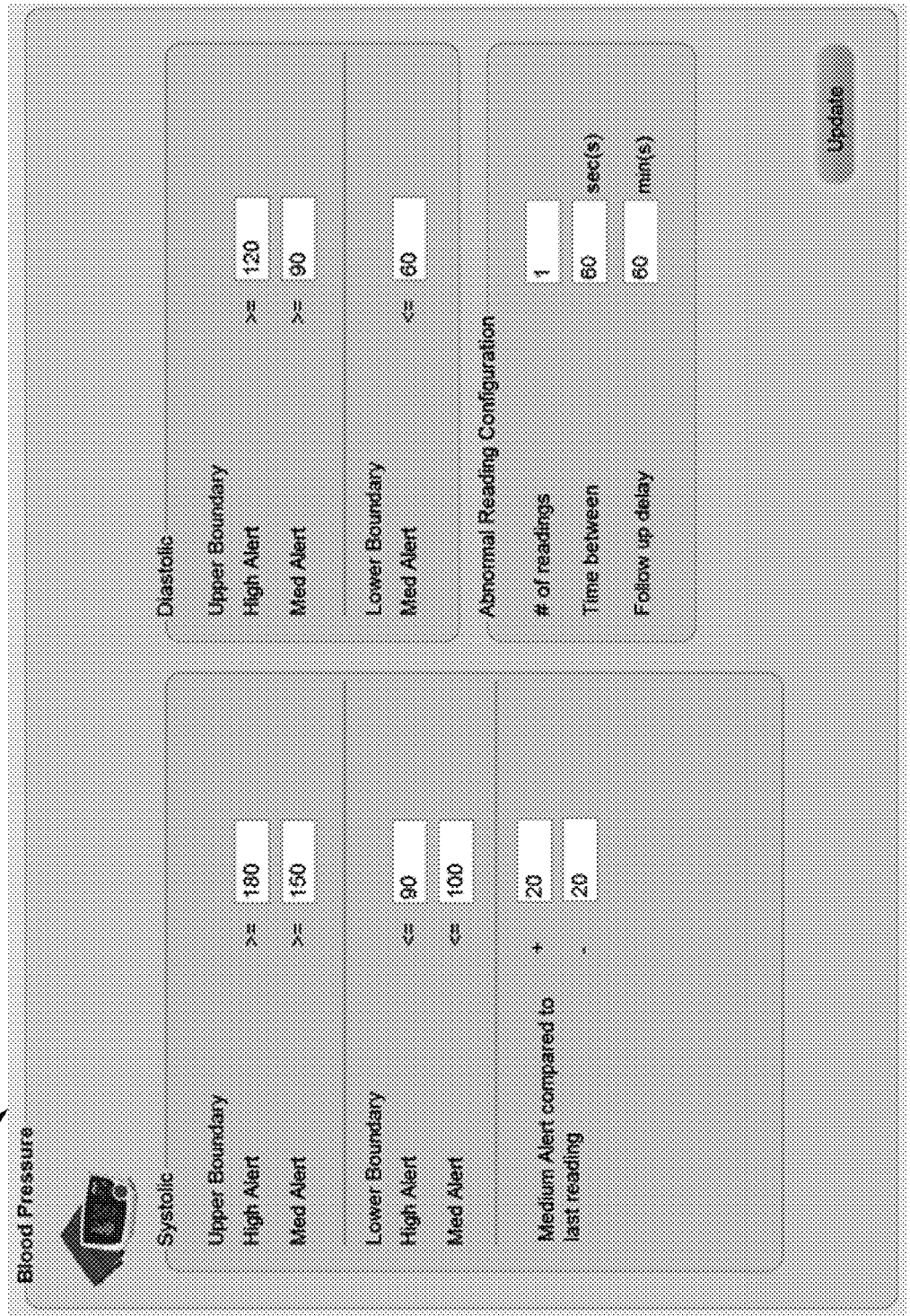
FIG. 48 illustrates an exemplary PHP blood pressure alert configuration dialog.
Figure 49:
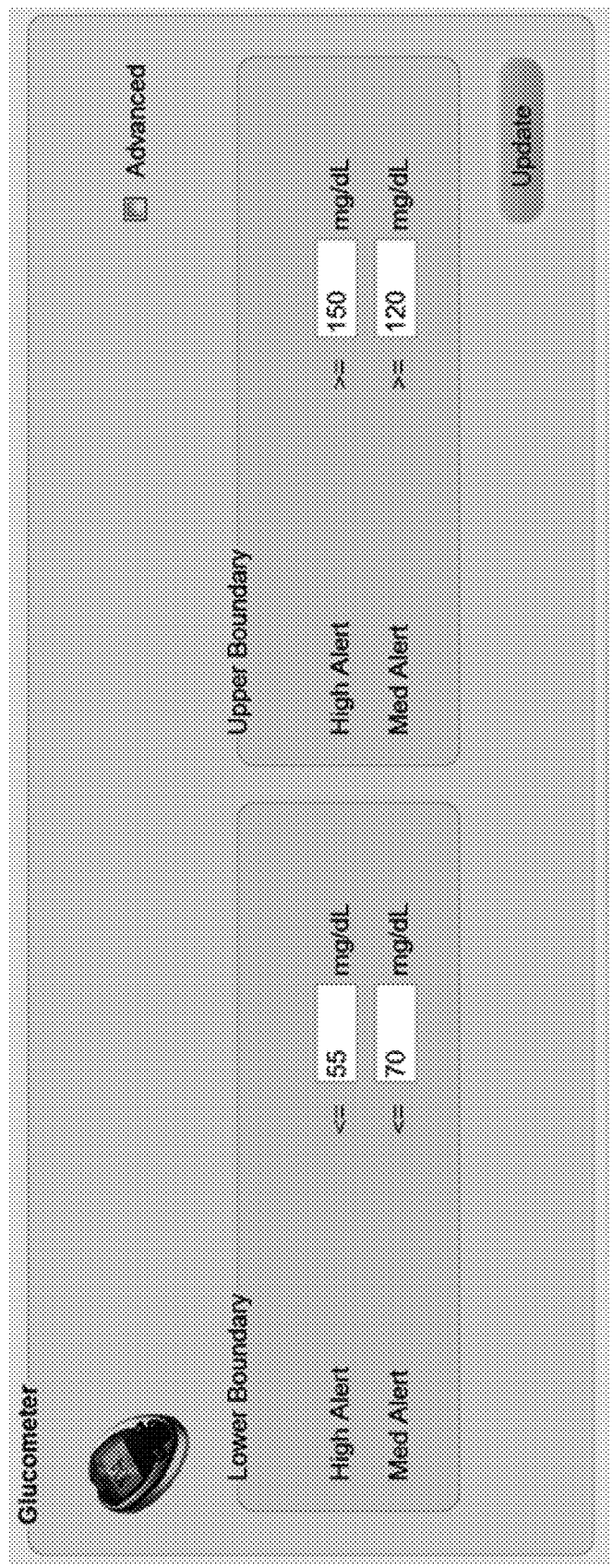
FIG. 49 illustrates an exemplary PHP glucometer alert configuration dialog.
Figure 50:
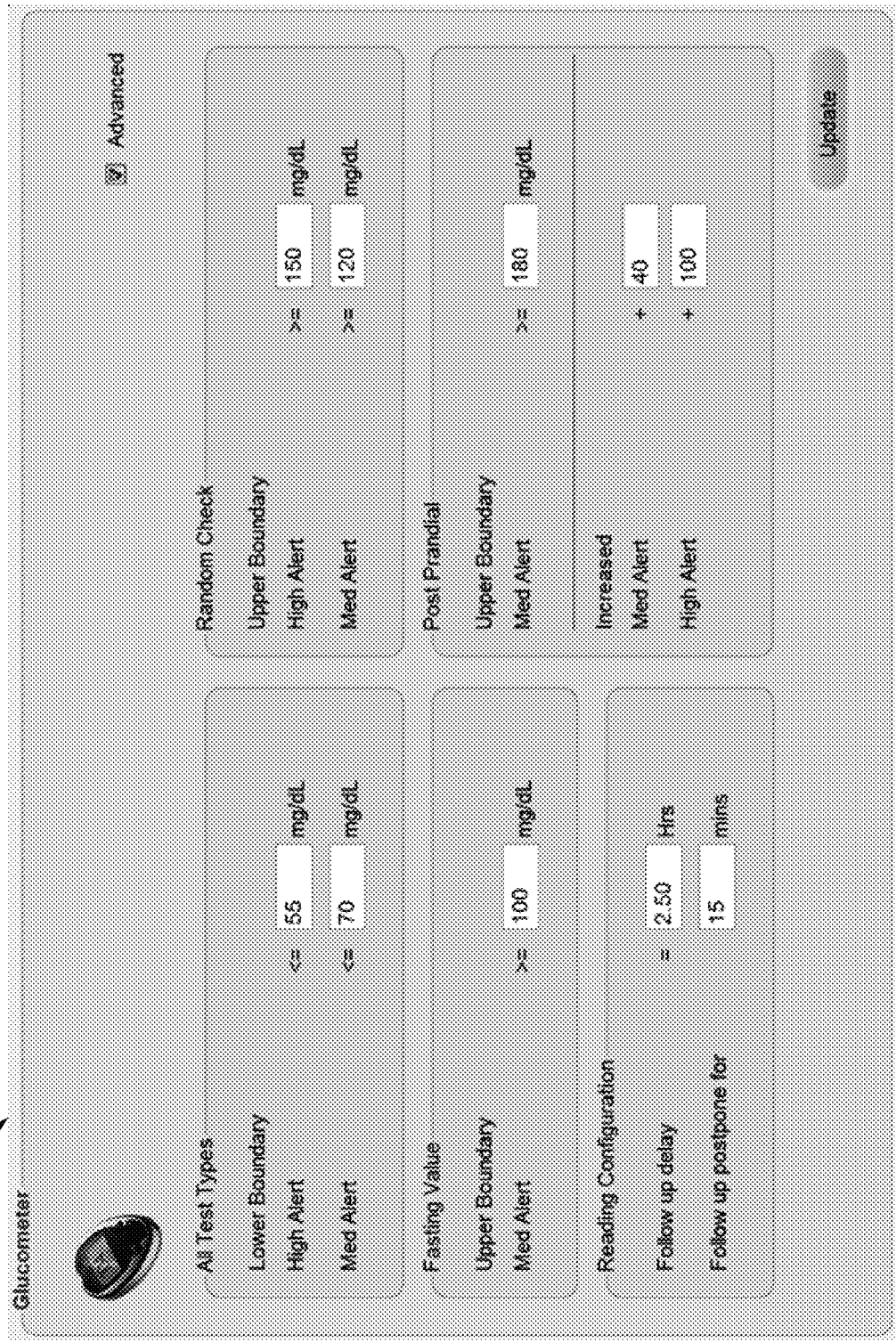
FIG. 50 illustrates an exemplary PHP advanced glucometer alert configuration dialog.

Examples of these types of alerts are generally provided in the exemplary screenshots depicted in FIG. 45 (4500)-FIG. 50 (5000). One skilled in the art will recognize that these are only exemplary of the alert scope which may be implemented using the MUD as directed by the PHP. It is important to realize that as the PHP is updated by healthcare professionals via the HWS web browser interface, it is simultaneously pushed down to the individual patient MUD systems for execution by the HWS. This real-time PHP deployment ensures that every patient is automatically updated with a current healthcare plan that may involve modifications to the patient measurements that are taken as well as associated alerts and patient educational interaction associated with the updated patient care plan.

Exemplary MID Alert Configuration Dialogs (4500)-(5000)

Examples of MID device configuration and MID alert definition dialogs used to create alerts within the PHP-driven healthcare plan are depicted in FIG. 45 (4500)-FIG. 50 (5000) and depict weight scale, pulse oximeter, blood pressure, and glucometer dialog configuration menus respectively. Note that these dialogs in some circumstances implement different alerts for MID measurement readings based on different alert ranges and conditions for the patient as well as alerts triggered based on missed readings or manual readings that exceed a certain threshold.

The MID device configuration page (FIG. 45 (4500)) permits a variety of MID "kits" to be defined based on the specific needs for patient device monitoring. Note that this dialog also permits for manual entry of data using the direct data entry dialog depicted in FIG. 51 (5100).

Exemplary Direct Entry Dialog (5100)

Figure 51:
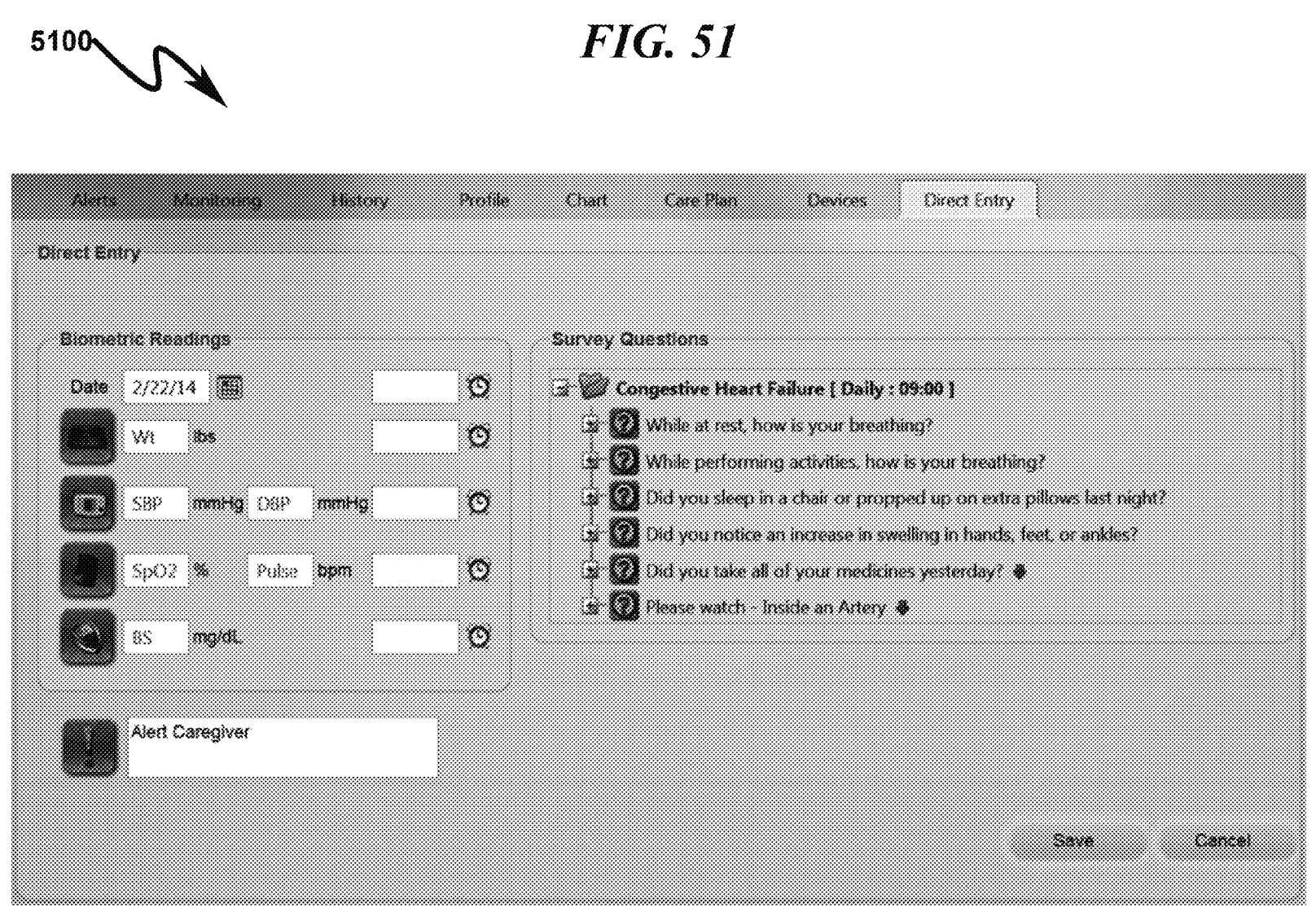

While the present invention anticipates that much of the MID information will be collected using a PHP-driven healthcare plan operating in the context of the MUD, as depicted in FIG. 51 (5100) the system does anticipate that under some circumstance MID data may be entered manually (such as for weight scale, pulse oximeter, blood pressure, and glucometer data as depicted). In addition, as depicted, the patient dialog question/answers can be manually entered by a healthcare professional interacting directly with the patient. This manual data entry option is useful in situations where the patient has failed to take MID biometric data or is unable or incapable of providing this information.

An exemplary Direct Entry dialog used to directly enter patient information within the PHP-driven healthcare plan is depicted in FIG. 51 (5100). This dialog permits a healthcare provider the opportunity to directly enter patient information that may be retrieved from the patient via the telephone or other means. Note that this dialog also permits entry of alert-driven responses to patient questions for patients that are unable to respond to these questions directly.

Exemplary Demographics Dialog (5200)

Figure 52:
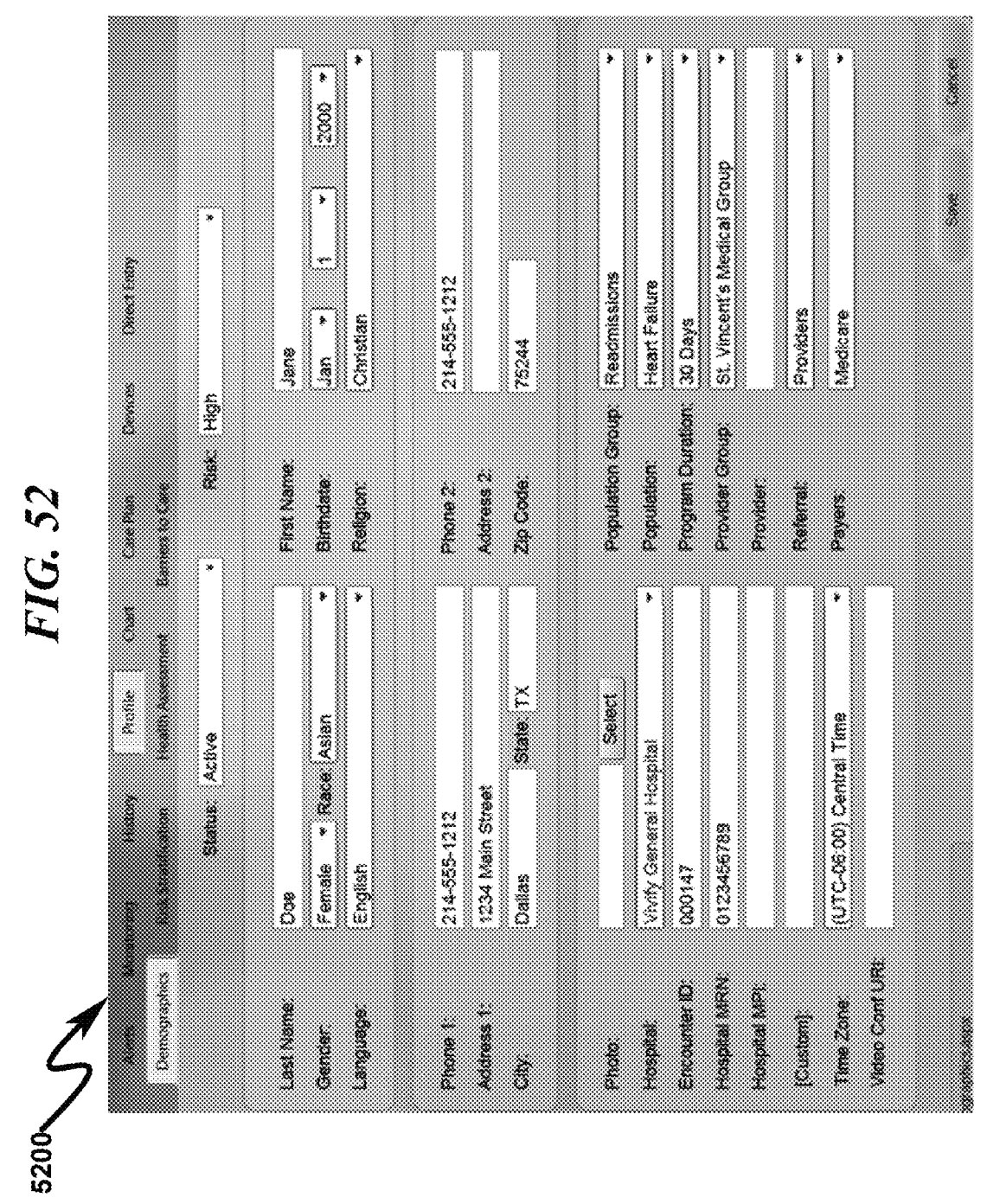

An exemplary Demographics dialog used to update patient information within the PHP-driven healthcare plan is depicted in FIG. 52 (5200) and depicts an exemplary dataset of patient information that may be used to risk stratify the patient and provide individualized healthcare. Information within this dialog including fields such as RACE, AGE, GENDER, etc. may be used with risk stratification paradigms to determine if the patient is at high risk for a variety of medical conditions.

Exemplary Risk Stratification Dialog (5300)-(5600)

Figure 53:
FIG. 53 illustrates an exemplary RISK STRATIFICATION data entry dialog interface (part 1/4)
Figure 55:
FIG. 55 illustrates an exemplary RISK STRATIFICATION data entry dialog interface (part 3/4)
Figure 56:
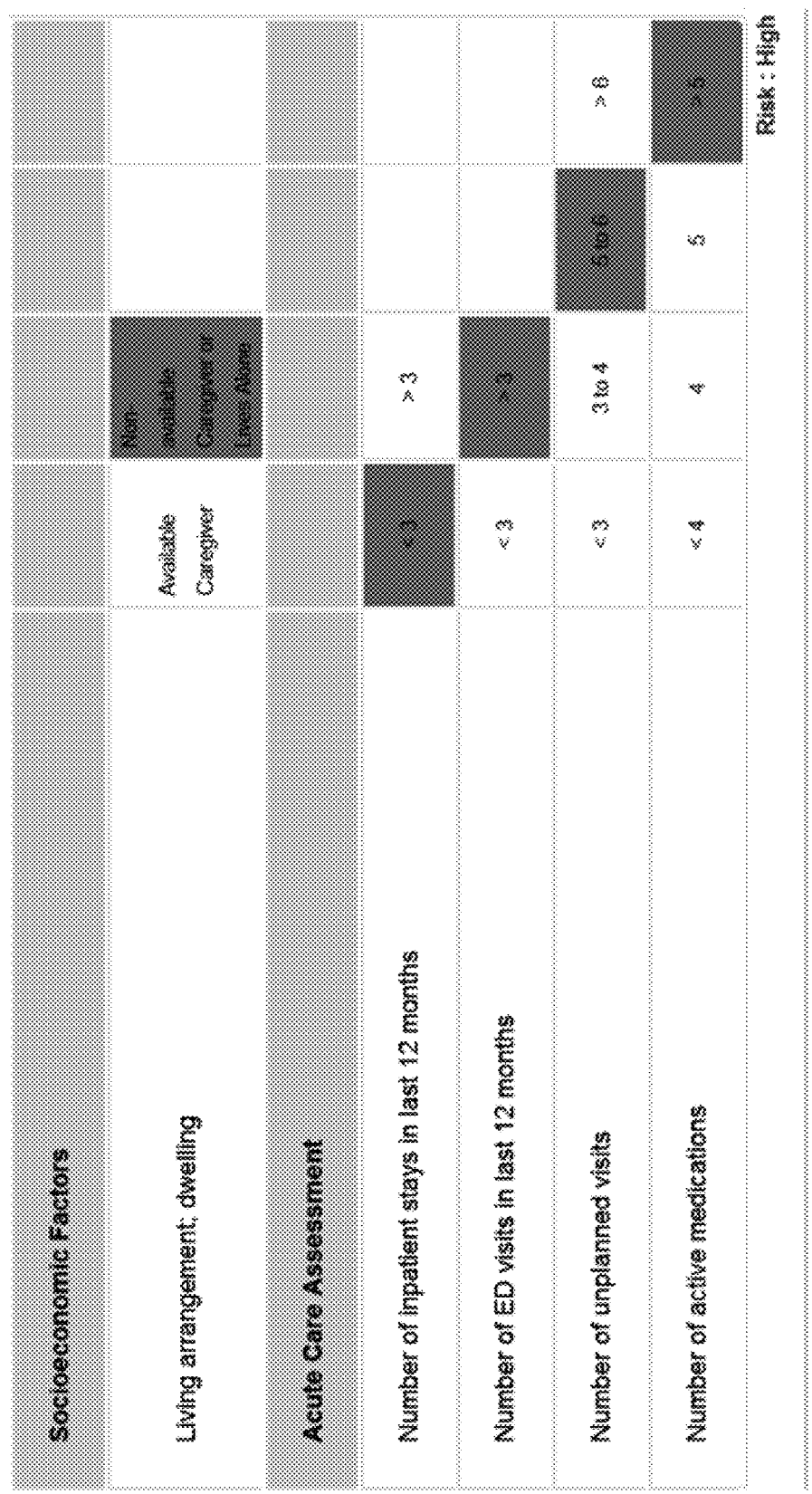
FIG. 56 illustrates an exemplary RISK STRATIFICATION data entry dialog interface (part 4/4)
Figure 58:
FIG. 58 illustrates an exemplary HEALTH ASSESSMENT data entry dialog interface (part 2/6)
Figure 59:
FIG. 59 illustrates an exemplary HEALTH ASSESSMENT data entry dialog interface (part 3/6)
Figure 60:
FIG. 60 illustrates an exemplary HEALTH ASSESSMENT data entry dialog interface (part 4/6)

Examples of Risk Assessment dialogs used to update patient status and further risk stratify the patient within the PHP-driven healthcare plan are depicted in FIG. 53 (5300)-FIG. 56 (5600) and depict an exemplary set of health conditions that may be used to categorize the patient risk for re-admission. The example provided in FIG. 53 (5300)-FIG. 56 (5600) depicts a combination of health conditions resulting in a HIGH risk level for the patient. However, other risk levels (NONE, LOW, MEDIUM, etc.) are anticipated as well. As patient conditions are modified, this information is updated and may result in modifications within the PHP to increase patient monitoring or trigger monitoring of a variety of patient monitors. This risk stratification information also promotes the priority of the patient to the healthcare team via the dynamic status displays to allow immediate attention to be given to high risk patients if their health status deteriorates.

Exemplary Health Assessment Dialog (5700)-(6200)

Examples of Health Assessment dialogs used to update patient status and further risk stratify the patient within the PHP-driven healthcare plan are depicted in FIG. 57 (5700)-FIG. 62 (6200) and depict an exemplary set of patient questions that may be used to categorize the patient health status. Note that these dialogs in some circumstances may be completed by a healthcare professional to dynamically respond to perceived changes in patient condition.

Exemplary Barriers to Care Dialog (6300)-(6400)

Examples of Barriers to Care dialogs used to update patient status and further risk stratify the patient within the PHP-driven healthcare plan are depicted in FIG. 63 (6300)-FIG. 64 (6400) and depict an exemplary set of patient questions that may be used to categorize the patient. Note that these dialogs in some circumstances may be completed by a healthcare professional to dynamically respond to perceived changes in patient condition.

Exemplary Application Contexts

The present invention may be utilized in a wide variety of disparate healthcare delivery contexts which may include but are not limited to hospitals, healthcare clinics, nursing homes, rehabilitation centers, physical therapy clinics, and the like. Patient interfacing with the MUD may include but is not limited to a wide variety of query/response dialogs that include healthcare information, patient cognitive skills tests, monitored patient medical information, and the like.

Preferred Embodiment System Summary

The present invention preferred exemplary system embodiment anticipates a wide variety of variations in the basic theme of construction, but can be generalized as a healthcare delivery system comprising:
  (a) hospital information system (HIS);
  (b) healthcare web server (HWS);
  (c) mobile user interface device (MUD);
  (d) medical instrumentation device (MID); and
  (e) computer communication network (CCN);
  wherein
  the HWS is configured to communicate with the HIS via the CCN;
  the HIS is configured to extract real-time patient data from a variety of patient data sources in the hospital;
  the HIS is configured to transmit the real-time patient data to the HWS;
  the HWS is configured to communicate with the MUD via the CCN;
  the MUD is configured to present audio/video information to a patient;
  the MUD is configured to accept user inputs from a patient;
  the MID is configured to detect medical events or conditions associated with a patient;
  the MID is configured to transmit information on the medical events or conditions to the MUD;
  the HWS is configured to permit definition of a patient healthcare plan (PHP) that controls the delivery of healthcare to a patient;
  the HWS is configured to transfer the PHP to the MUD via the CCN;
  the MUD is configured to execute the PHP to control presentation of the audio/video information to a patient;
  the MUD is configured to execute the PHP to control acceptance of the user inputs from a patient;
  the MUD is configured to execute the PHP to control detection of medical events or conditions associated with a patient via operation of the MID;
  the PHP is configured to permit definition of alerts that are associated with time triggers or detected patient events;
  the HWS is configured to allow authorized healthcare professionals access to real-time status information on patients under their care via a web browser interface;
  the real-time status information includes the real-time patient data, the user inputs, the time triggers, and the detected patient events; and
  the HWS is configured to perform a risk stratification analysis (RSA) of the hospital patient data, the remote patient monitoring (RPM) data, and the alerts and display the RSA to a status dashboard via a web browser interface.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a healthcare delivery method, the method operating in conjunction with a healthcare delivery system comprising:
  (a) hospital information system (HIS);
  (b) healthcare web server (HWS);
  (c) mobile user interface device (MUD);
  (d) medical instrumentation device (MID); and
  (e) computer communication network (CCN);
  wherein
  the HWS is configured to communicate with the HIS via the CCN;
  the HIS is configured to extract real-time patient data from a variety of patient data sources in the hospital;
  the HIS is configured to transmit the real-time patient data to the HWS;
  the HWS is configured to communicate with the MUD via the CCN;
  the MUD is configured to present audio/video information to a patient;
  the MUD is configured to accept user inputs from a patient;
  the MID is configured to detect medical events or conditions associated with a patient;
  the MID is configured to transmit information on the medical events or conditions to the MUD;
  the HWS is configured to permit definition of a patient healthcare plan (PHP) that controls the delivery of healthcare to a patient;
  the HWS is configured to transfer the PHP to the MUD via the CCN;
  the MUD is configured to execute the PHP to control presentation of the audio/video information to a patient;
  the MUD is configured to execute the PHP to control acceptance of the user inputs from a patient;
  the MUD is configured to execute the PHP to control detection of medical events or conditions associated with a patient via operation of the MID;

the PHP is configured to permit definition of alerts that are associated with time triggers or detected patient events;

the HWS is configured to allow authorized healthcare professionals access to real-time status information on patients under their care via a web browser interface;

the real-time status information includes the real-time patient data, the user inputs, the time triggers, and the detected patient events; and the HWS is configured to perform a risk stratification analysis (RSA) of the hospital patient data, the remote patient monitoring (RPM) data, and the alerts and display the RSA to a status dashboard via a web browser interface;

wherein the method comprises the steps of:
(1) with the HWS, correlating the real-time patient data to individual patients;
(2) with the HWS, entering data from a web browser interface from a healthcare professional to define the PHP;
(3) with the HWS, integrating the RPM data, the real-time patient data, and the alerts generated by the PHP to form a risk stratification index associated with a patient;
(4) with the HWS, risk stratifying patients in patient groups to queue prioritized healthcare delivery within the patient groups;
(5) with the HWS, displaying a risk stratification dashboard via a web browser in real-time to trigger healthcare provider activity on specific patients within the patient groups;
(6) with the HWS, updating or clearing patient alert status once a patient status is improved or modified;
(7) with the HWS, entering data from a web browser interface from a healthcare professional to update or modify the PHP; and
(8) with the HWS, triggering interaction between a patient and a healthcare professional based on the state of the PHP.

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the CCN comprises the Internet.

An embodiment wherein the MID is selected from a group consisting of: weight scale; pulse oximeter; blood pressure meter; and blood glucose meter.

An embodiment wherein the PHP comprises a hierarchical decision tree incorporating alert conditions triggered based on upper and lower range values associated with measurements from the MID.

An embodiment wherein the PHP comprises a hierarchical decision tree incorporating a plurality of risk stratification alert conditions triggered based on multiple upper/lower range values associated with measurements from the MID.

An embodiment wherein the PHP comprises a hierarchical decision tree incorporating alert conditions triggered based on differential delta values associated with multiple measurements from the MID.

An embodiment wherein the PHP comprises a hierarchical decision tree incorporating alert conditions triggered based on the failure of the patient to execute a biometric measurement from the MID.

An embodiment wherein the PHP comprises a hierarchical decision tree incorporating alert conditions triggered based on the entry of multiple manual biometric measurement entries from the patient.

An embodiment wherein the PHP is configured to trigger biometric measurements from the MID on a demand basis.

An embodiment wherein the PHP is configured to trigger biometric measurements from the MID on a periodic basis.

An embodiment wherein the PHP is configured to trigger manual and automatic biometric measurements from the MID on a periodic basis.

An embodiment wherein the RSA is configured to calculate per-patient risk assessments via summation of individual patient datum risk values.

An embodiment wherein the HWS is configured to provide PHP patient care plan templates associated with specific diseases and medical conditions that may be used as the basis for the creation of a custom PHP patient care plan.

An embodiment wherein the HWS is configured to permit PHP patient care plan templates to be inserted within a custom PHP patient care plan using a drag-and-drop graphical user interface (GUI).

An embodiment wherein the PHP comprises patient queries incorporating responses selected from a group consisting of: single selections; multiple selections; and yes/no responses.

An embodiment wherein the PHP comprises patient queries that have associated response alert values selected from a group consisting of: no alert; medium alert; and high alert.

An embodiment wherein the PHP comprises triggers to execute presentation of audio/visual educational materials to a patient via the MUD.

An embodiment wherein the HWS is configured to:
(1) receive data/alert messages from the MUD;
(2) update a patient electronic medical record (EMR) with the data/alert messages;
(3) determine if alerts have been triggered by the MUD and deliver the alerts via a web browser interface to a healthcare provider if the alerts have been triggered; and
(4) determine if a healthcare provider via a web browser interface has updated the PHP and trigger a download of a new PHP to the MUD if the PHP has been updated.

An embodiment wherein the MUD is configured to:
(1) register MID equipment for automated measurement readings from a patient;
(2) capture MID equipment data under control of the PHP;
(3) determine if the MID data falls within the bounds of an alert limit and generate an alert and queue the alert for transmission to the HWS in the event the alert limit is within the bounds;

(4) determine if a patient interaction has been staged by the PHP and initiate a patient interaction involving a query/response or audio/video interaction if the patient interaction has been staged; and (5) determine if a patient interaction alert has been triggered and generate a patient interaction alert for queued transmission to the HWS if the patient interaction alert has been triggered.

An embodiment wherein the MUD is configured to:

(1) determine if the HWS has a PHP update ready for installation and then authenticate and synchronize the installation of the PHP update to a local copy of the patient PHP if the PHP update is ready for installation; and (2) determine if patient data/alerts are queued for transmission to the HWS and transmit the patient data/alerts to the HWS if the patient data/alerts are queued for transmission.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to *In re Beauregard*, 35 USPQ2d 1383 (U.S. Pat. No. 5,710,578), the present invention anticipates and includes this type of computer readable media within the scope of the invention. Pursuant to *In re Nuijten*, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method integrating healthcare delivery to patients using data bridges that connect healthcare providers, patients, patient medical education, and patient monitoring devices has been disclosed. The system incorporates a mobile user interface device (MUD) allowing user inputs or detected events from a variety of medical instrumentation devices (MID) to be controlled by a healthcare web server computer (HWS) over a computer communication network (CCN). Information retrieved from the MID and transmitted by the MUD to the HWS is then used by a patient healthcare monitor (PHM) process to populate a medical records database (MRD). MRD contents are then matched to patient healthcare plan (PHP) event/time triggers (ETT) that drive information from a provider content database (PCD) to the MUD through the HWS over the CCN. Healthcare provider update/control of the PHP/ETT/PCD allow integration of patient educational materials with patient health status monitoring.

What is claimed is:

1. A healthcare delivery system comprising:
   (a) hospital information system (HIS);
   (b) healthcare web server (HWS);
   (c) mobile user interface device (MUD);
   (d) medical instrumentation device (MID); and
   (e) computer communication network (CCN);
   wherein
   said HWS is configured to communicate with said HIS via said CCN;
   said HIS is configured to extract real-time data associated with a hospital in-patient from patient data sources in said hospital;
   said HIS is configured to transmit said real-time hospital in-patient data to said HWS;
   said MUD is associated with said in-patient after said in-patient is discharged from said hospital and said in-patient becomes an out-patient;
   said HWS is configured to communicate with said MUD via said CCN;
   said MUD is configured to accept user inputs from said out-patient;
   said MID is configured to physically interact with the body of said out-patient and collect real-time biometric data associated with the physical condition of said out-patient;
   said MID is configured to detect medical events associated with said out-patient;
   said MID is configured to detect medical conditions associated with said out-patient;
   said MID is configured to transmit information on said medical events to said MUD;
   said MID is configured to transmit information on said medical conditions to said MUD;
   said MID is configured to transmit said real-time biometric data to said MUD;
   said HWS is configured to permit definition of a patient healthcare plan (PHP) that controls the delivery of healthcare to said out-patient;
   said HWS is configured to transfer said PHP to said MUD via said CCN;
   said MUD is configured to execute said PHP to control presentation of audio/video information to said out-patient;
   said MUD is configured to execute said PHP to control acceptance of said user inputs from said out-patient;
   said MUD is configured to execute said PHP to control detection of medical events associated with said out-patient via operation of said MID;
   said MUD is configured to execute said PHP to control detection of medical conditions associated with said out-patient via operation of said MID;
   said PHP is configured to permit definition of alerts that are associated with time triggers;

said PHP is configured to permit definition of alerts that are associated with detected medical events for said out-patient;

said PHP comprises triggers to execute presentation of audio/visual educational materials based on said medical events to said out-patient via said MUD;

said PHP comprises triggers to execute presentation of audio/visual educational materials based on said medical conditions to said out-patient via said MUD;

said PHP comprises a hierarchical decision tree incorporating alert conditions triggered based on the failure of said out-patient to execute a manual biometric measurement from said MID;

said HWS is configured to allow an authorized healthcare professional access to real-time status information on said out-patient under the care of said authorized healthcare professional via a web browser interface;

said real-time status information includes said real-time biometric data, said real-time data on said hospital in-patient, said real-time data on said out-patient, said user inputs, said time triggers, said medical events, and said medical conditions;

said HWS is configured to continuously perform a risk stratification analysis (RSA) of said real-time hospital in-patient data, said real-time biometric data, and said alerts and display said RSA to a status dashboard via a web browser interface;

said HWS is configured to allow said authorized healthcare professional to edit said PHP via said HWS in response to the display of said RSA on said status dashboard to generate an updated PHP;

said HWS is configured to automatically transfer said updated PHP to said MUD via said CCN; and said MUD is configured to execute said updated PHP autonomously upon receipt of said updated PHP from said HWS.

2. The healthcare delivery system of claim 1 wherein said CCN comprises the Internet.

3. The healthcare delivery system of claim 1 wherein said MID is selected from a group consisting of: weight scale; pulse oximeter; blood pressure meter; and blood glucose meter.

4. The healthcare delivery system of claim 1 wherein said PHD comprises a hierarchical decision tree incorporating alert conditions triggered based on upper and lower range values associated with measurements from said MID.

5. The healthcare delivery system of claim 1 wherein said PHP comprises a hierarchical decision tree incorporating a plurality of risk stratification. alert conditions triggered based on multiple upper/lower range values associated with measurements from said MID.

6. The healthcare delivery system of claim 1 wherein said PHD comprises a hierarchical decision tree incorporating alert conditions triggered based on differential delta values associated with multiple measurements from said MID.

7. The healthcare delivery system of claim 1 wherein said PHP comprises a hierarchical decision tree incorporating alert conditions triggered based on the entry of multiple manual biometric, measurement entries from said out-patient.

8. The healthcare delivery system of claim 1 wherein said PHP is configured to trigger biometric measurements from said MID on a demand basis.

9. The healthcare delivery system of claim 1 wherein said PHP is configured to trigger biometric measurements from said MID on a periodic basis.

10. The healthcare delivery system of claim 1 wherein said PHP is configured to trigger manual and automatic biometric measurements from said MID on a periodic basis.

11. The healthcare delivery system of claim 1 wherein said RSA is configured to calculate per-patient risk assessments via summation of individual patient datum risk values.

12. The healthcare delivery system of claim wherein said HWS is configured to provide PHP patient care plan templates associated with specific diseases and medical conditions that may be used as the basis for the creation of a custom PHP patient care plan.

13. The healthcare delivery system of claim 1 wherein said HWS is configured to permit PHP patient care plan templates to be inserted within a custom PHP patient care plan using a drag-and-drop graphical user interface (GUI).

14. The healthcare delivery system of claim 1 wherein said PHP comprises patient queries incorporating responses selected from a group consisting of: single selections; multiple selections; and yes/no responses.

15. The healthcare delivery system of claim 1 wherein said PHP comprises patient queries that have associated response alert values selected from a group consisting of: no alert; medium alert; and high alert.

16. The healthcare delivery system of claim 1 wherein said HWS is configured to:
(1) receive data/alert messages from said MUD;
(2) update a patient electronic medical record (EMR) with said data/alert messages;
(3) determine if alerts have been triggered by said MUD and deliver said alerts via a web browser interface to a healthcare provider if said alerts have been triggered; and
(4) determine if a healthcare provider via a web browser interface has updated said PHP and trigger a download of a new PHP to said MUD if said PHP has been updated.

17. The healthcare delivery system of claim 1 wherein said MUD is configured to:
(1) register MID equipment for automated measurement readings from a patient;
(2) capture MID equipment data under control of said PHP;
(3) determine if said MID data falls within the bounds of an alert limit and generate an alert and queue said alert for transmission to said HWS in the event said alert limit is within said bounds;
(4) determine if a patient interaction has been staged by said PHP and initiate a patient interaction involving a query/response or audio/video interaction if said patient interaction has been staged; and
(5) determine if a patient interaction alert has been triggered and generate a patient interaction alert for queued transmission to said HWS if said patient interaction alert has been triggered.

18. The healthcare delivery system of claim 1 wherein said MUD is configured to:
(1) determine if said HWS has a PHP update ready for installation and then authenticate and synchronize the installation of said PUP update to a local copy of the patient PHP if said PHP update is ready for installation; and
(2) determine if patient data/alerts are queued for transmission to said HWS and transmit said patient data/alerts to said HWS if said patient data/alerts are queued for transmission.

19. A healthcare delivery method comprising:
(1) establishing communications between a healthcare web server (HWS) and a hospital information system (HIS) via a computer communication network (CCN);
(2) with said HIS, extracting real-time data associated with a hospital in-patent from patent data sources in said hospital;
(3) with said HIS, transmitting said real-time hospital in-patient data to said HWS;
(4) associating a mobile user device (MUD) with said in-patient after said in-patient discharged from said hospital and said in-patient becomes an out-patient;
(5) with said HWS, communicating with said MUD via said CCN;
(6) with said MUD, accepting user inputs from said out-patient;
(7) with a medical instrumentation device (MID), physically interacting with the body of said out-patient and collect real-time biometric data associated with the physical condition of said out-patient;
(8) with said MID, detecting medical events associated with said out-patient;
(9) with said MID, detecting medical conditions associated with said out-patient;
(10) with said MID, transmitting information on said medical events to said MUD;
(11) with said MID, transmitting information on said medical conditions to said MUD;
(12) with said MID, transmitting said real-time biometric data to said MUD;
(13) with said HWS, permitting definition of a patient healthcare plan (PHP) that controls the delivery of healthcare to said out-patient by a healthcare professional;
(14) with said HWS, transferring said PHP to said MUD via said CCN;
(15) with said MUD, executing said PHP to control presentation of audio/video information to said out-patient;
(16) with said MUD, executing said PHP to control acceptance of said user inputs from said out-patient;
(17) with said MUD, executing said PHP to control detection of medical events associated with said out-patient via operation of said MID;
(18) with said MUD, executing said PHP to control detection of medical conditions associated with said out-patient via operation of said MID;
(19) with said HWS, allowing an authorized healthcare professional access via a web browser interface to real-time status information retrieved from said MUD on said out-patient under the care of said authorized healthcare professional;
(20) with said HWS, continuously performing a risk stratification analysis (RSA) of said real-time hospital in-patient data, said real-time biometric data, and said alerts and display said RSA to a status dashboard via a web browser interface;
(21) with said HWS, allowing said authorized healthcare professional to edit said PHP via said HWS in response to the display of said RSA on said status dashboard to generate an updated PHP;
(22) with said HIS, automatically transferring said updated PHP to said MUD via said CCN;
(23) with said MUD, executing said updated PHP autonomously upon receipt of said updated PHP from said HWS; and
(24) with said MUD, transmitting said medical events, said medical conditions, and said real-time biometric data retrieved from said MID to said HWS for display to said authorized healthcare professional;
wherein
said PHP comprises definitions of alerts that are associated with time triggers;
said PHP comprises definitions of alerts that are associated with detected medical events for said out-patient;
said PHP comprises triggers to execute presentation of audio/visual educational materials based on said medical events to said out-patient via said MUD;
said PHP comprises triggers to execute presentation of audio/visual educational materials based on said medical conditions to said out-patient via said MUD;
said PHP comprises a hierarchical decision tree incorporating alert conditions triggered based on the failure of said out-patient to execute a manual biometric measurement from said MID; and
said real-time status information comprises said real-time biometric data, said real-time data on said hospital in-patient, said real-time data on said out-patient, said user inputs, said time triggers, said medical events, and said medical conditions.

20. The healthcare delivery method of claim 19 wherein said CCN comprises the Internet.

21. The healthcare delivery method of claim 19 wherein said MID is selected from a group consisting of: weight scale; pulse oximeter; blood pressure meter; and blood glucose meter.

22. The healthcare delivery method of claim 19 wherein said PHP comprises a hierarchical decision tree incorporating alert conditions triggered based on upper and lower range values associated with measurements from said MID.

23. The healthcare delivery method of claim 19 wherein said PHP comprises a hierarchical decision tree incorporating a plurality of risk stratification alert conditions triggered based on multiple upper/lower range values associated with measurements from said MID.

24. The healthcare delivery method of claim 19 wherein said PHP comprises a hierarchical decision tree incorporating alert conditions triggered based on differential delta values associated with multiple measurements from said MID.

25. The healthcare delivery method of claim 19 wherein said PHP comprises a hierarchical decision tree incorporating alert conditions triggered based on the entry of multiple manual biometric measurement entries from said out-patient.

26. The healthcare delivery method of claim 19 wherein said PHP is configured to trigger biometric measurements from said MID on a demand basis.

27. The healthcare delivery method of claim 19 wherein said PHP is configured to trigger biometric measurements from said MID on a periodic basis.

* * * * *